(12) United States Patent
Shirude et al.

(10) Patent No.: US 11,117,861 B2
(45) Date of Patent: *Sep. 14, 2021

(54) PHENYLPYRROLIDINONE FORMYL PEPTIDE 2 RECEPTOR AGONISTS

(71) Applicant: BRISTOL-MYERS SQUIBB COMPANY, Princeton, NJ (US)

(72) Inventors: Pravin Sudhakar Shirude, Bangalore (IN); Vishweshwaraiah Baligar, Bangalore (IN); Balaji Seshadri, Hosur (IN); Amit Kumar Chattopadhyay, Bangalore (IN); Nicholas R. Wurtz, Pennington, NJ (US); Ellen K. Kick, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/858,319

(22) Filed: Apr. 24, 2020

(65) Prior Publication Data

US 2020/0255375 A1  Aug. 13, 2020

Related U.S. Application Data

(63) Continuation of application No. 16/291,209, filed on Mar. 4, 2019, now Pat. No. 10,676,431.

(60) Provisional application No. 62/638,556, filed on Mar. 5, 2018.

(51) Int. Cl.

| A61K 31/4015 | (2006.01) |
| A61K 31/4439 | (2006.01) |
| A61K 31/497 | (2006.01) |
| A61K 31/675 | (2006.01) |
| C07D 207/14 | (2006.01) |
| C07D 403/10 | (2006.01) |
| C07D 401/10 | (2006.01) |
| C07D 401/12 | (2006.01) |
| A61P 9/10 | (2006.01) |
| C07D 413/10 | (2006.01) |
| C07D 409/12 | (2006.01) |
| A61P 9/04 | (2006.01) |
| C07D 403/12 | (2006.01) |
| C07F 9/6558 | (2006.01) |
| C07D 405/10 | (2006.01) |
| C07F 9/572 | (2006.01) |
| A61P 9/00 | (2006.01) |
| C07D 417/10 | (2006.01) |
| C07D 413/14 | (2006.01) |

(52) U.S. Cl.
CPC ........ *C07D 207/14* (2013.01); *A61K 31/4015* (2013.01); *A61K 31/4439* (2013.01); *A61K 31/497* (2013.01); *A61K 31/675* (2013.01); *A61P 9/00* (2018.01); *A61P 9/04* (2018.01); *A61P 9/10* (2018.01); *C07D 401/10* (2013.01); *C07D 401/12* (2013.01); *C07D 403/10* (2013.01); *C07D 403/12* (2013.01); *C07D 405/10* (2013.01); *C07D 409/12* (2013.01); *C07D 413/10* (2013.01); *C07D 413/14* (2013.01); *C07D 417/10* (2013.01); *C07F 9/572* (2013.01); *C07F 9/5728* (2013.01); *C07F 9/65583* (2013.01); *C07F 9/65586* (2013.01)

(58) Field of Classification Search
None
See application file for complete search history.

(56) References Cited

U.S. PATENT DOCUMENTS

| 9,822,069 B2 | 11/2017 | Takahashi et al. |
| 10,676,431 B2 | 6/2020 | Shirude et al. |
| 2009/0163545 A1 | 6/2009 | Goldfarb |

FOREIGN PATENT DOCUMENTS

| WO | WO1992010476 A1 | 6/1992 |
| WO | WO199533719 A1 | 12/1995 |
| WO | WO2004071460 A2 | 8/2004 |
| WO | WO2005021500 A1 | 3/2005 |
| WO | WO2005047899 A2 | 5/2005 |
| WO | WO2006063113 A2 | 6/2006 |
| WO | WO2006063293 A2 | 6/2006 |
| WO | WO2006127396 A1 | 11/2006 |

(Continued)

OTHER PUBLICATIONS

Krishnamoorthy et al., "Resolvin D1 binds human phagocytes with evidence for proresolving receptors", PNAS, vol. 107(4), pp. 1660-1665 (2010).

(Continued)

*Primary Examiner* — Joseph R Kosack
(74) *Attorney, Agent, or Firm* — Hong Liu

(57) ABSTRACT

The disclosure relates to compounds of Formulae (I)-(IX), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, chronic obstructive pulmonary disease (COPD), and related diseases.

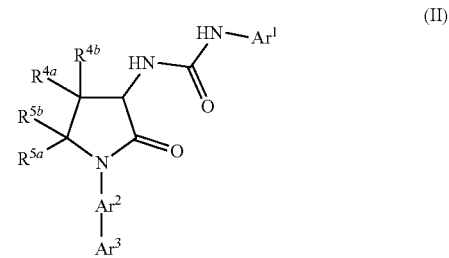

15 Claims, No Drawings

(56) References Cited

FOREIGN PATENT DOCUMENTS

| | | |
|---|---|---|
| WO | WO2007005668 A2 | 1/2007 |
| WO | WO2008076754 A2 | 6/2008 |
| WO | WO2009077954 A1 | 6/2009 |
| WO | WO2009077990 A1 | 6/2009 |
| WO | WO2010032856 A1 | 3/2010 |
| WO | WO2010094678 A1 | 8/2010 |
| WO | WO2010142801 A1 | 12/2010 |
| WO | WO2010143158 A1 | 12/2010 |
| WO | WO2011163502 A1 | 12/2011 |
| WO | WO2012066488 A2 | 5/2012 |
| WO | WO2012074785 A1 | 6/2012 |
| WO | WO2012077049 A1 | 6/2012 |
| WO | WO2012077051 A1 | 6/2012 |
| WO | WO2012109544 A1 | 8/2012 |
| WO | WO2012125305 A1 | 9/2012 |
| WO | WO2012158413 A2 | 11/2012 |
| WO | WO2013062947 A1 | 5/2013 |
| WO | WO2013070600 A1 | 5/2013 |
| WO | WO2013071203 A1 | 5/2013 |
| WO | WO2013158597 A1 | 10/2013 |
| WO | WO2014078323 A1 | 5/2014 |
| WO | WO2014078372 A1 | 5/2014 |
| WO | WO2014078378 A1 | 5/2014 |
| WO | WO2015009545 A1 | 1/2015 |
| WO | WO2015019325 A1 | 2/2015 |
| WO | WO2015084796 A1 | 6/2015 |
| WO | WO2015175788 A1 | 11/2015 |
| WO | WO2016116900 A1 | 7/2016 |
| WO | WO2016189876 A1 | 12/2016 |
| WO | WO2016189877 A1 | 12/2016 |
| WO | WO2017091496 A1 | 6/2017 |
| WO | WO2017100390 A1 | 6/2017 |
| WO | WO2017212423 A1 | 12/2017 |
| WO | WO2018227058 A9 | 12/2018 |
| WO | WO2018227061 A1 | 12/2018 |
| WO | WO2018227065 A1 | 12/2018 |
| WO | WO2018227067 A1 | 12/2018 |

OTHER PUBLICATIONS

Murphy et al., "A Structural Homologue of the N-Formyl Peptide Receptor", The Journal of Biological Chemistry, vol. 267(11), pp. 7637-7643 (1992).
Burli et al., "Potent hFPRLI (ALXR) agonists as potential anti-inflammatory agents", Bioorganic & Medicinal Chemistry Letters, vol. 16(14), pp. 3713-3718 (2006).
Cattaneo et al., "Distinct Signaling Cascades Elicited by Different Formyl Peptide Receptor 2 (FPR2) Agonists" Int. J. Mol. Sci., vol. 14, pp. 7193-7230 (2013).
Cilibrizzi et al., "6-Methyl-2,4-Disubstituted Pyridazin-3(2H)-ones: A Novel Class of Small-Molecule Agonists for Formyl Peptide Receptors" Journal of Medical Chemistry, vol. 52(16), pp. 5044-5057 (2009).
Dufton et al., "Anti- Inflammatory Role of the Murine Formyl-Peptide Receptor 2: Ligand~Spectic Effects on Leukocyte Responses and Experimental Inflammation", Journal of Immunology, vol. 184(5), pp. 2611-2619 (2010).
Frohn et al., "New 'chemical probes' to examine the role of the hFPRLI(or ALXR) receptor in inflammation", Bioorganic & Medicinal Chemistry Letters, vol. 17(23), pp. 6633-6637 (2007).
Gardell et al., "Identification and Characterization of Novel Small-Molecule Protease-Activated Receptor 2 Agonists", J. Pharmacol. Exp. Ther., vol. 327, pp. 799-808 (2008).
Gavins, Felicity N.E., "Are formyl peptide receptors novel targets for therapeutic intervention ischaemia-reperfusion injury?" Trends in Pharmacological Sciences, vol. 31(6), pp. 266-276 (2010).
He et al., "Characterization of Quin-C1 for its anti-inflammatoryproperty in a mouse model of bleomycin-induced lung injury" Acta Pharmacol. Sinica, vol. 32(5), pp. 601-610 (2011).
Khlebikov et al., "Computational Structure-activity Relationship Analysis of Small-Molecule Agonists for Human Formyl Peptide Receptors", Eur. J. Med. Chem., vol. 45, pp. 5406-5419 (2010).
Kim et al., "A WKYMVm-Containing Combination Elicits Potent AntiTumor Activity in Heterotopic Cancer Animal Model", PLos One, vol. 7(1), pp. e30522 (2012).
Kim et al., "The Agonists of Formyl Peptide Receptors Prevent Development of Severe Sepsis after Microbial Infection", The Journal of Immunology, vol. 185(7), pp. 4302-4310 (2010).
Kim et al., "The immune-stimulating peptide WKYMVm has therapeutic effects against ulcerative colitis", Experimental & Molecular Medicine, vol. 45, pp. e40, (2013).
Kirpotina et al., "Identification of Novel Small-Molecule Agonists for Human Formyl Peptide Receptors and Pharmacophore Models ofTheir Recognition", Molecular Pharmacology, vol. 77(2), pp. 159-170 (2010).
Knobler et al., "Cyclization reactions of N-carbamoyl and N-acyl derivatives of DL-homoserine", Tetrahedron, vol. 23 (3), 1557-63 (1967).
Le, et al., "Formyl-peptide receptors revisited", Trends in Immunology, vol. 23(11), pp. 541-548 (2002).
Li et al., "The synthetic peptide WKYVm attenuates the function of the chemokine receptors CCR5 and CXCR4 through activation of formyl peptide receptor-like 1", Blood, vol. 97(10), pp. 2941-2947 (2001).
Nanomori et al., "A Novel Nonpeptide Ligand for Formyl Peptide Receptor-Like 1", Molecular Pharmacology, vol. 66(5), pp. 1213-1222 (2004).
Schepetkin et al., "3-(1 H-Indol-3-yl)-2[3-(4-nitrophenyl)ureido]propanamide Enantiomers With Human Formyl-Peptide Receptor Agonist Activity: Molecular Modeling of Chiral Recognition by FPR2", Biochem. Pharmacol. vol. 85, pp. 404-416 (2013).
Schepetkin et al.,"Gastrin-Releasing Peptide/Neuromedin B Receptor Antagonists PD176252, PD168368, and Related Analogs Are PotentAgonists of Human Formyl-Peptide Receptors", Molecular Pharmacology, vol. 79(1), pp. 77-90 (2011).
Seitzberg et al., "Discovery of Potent and Selective Small-Molecule PAR-2 Agonists", Journal Medicinal Chemistry, vol. 51, pp. 5490-5493 (2008).
Sogawa et al., "Inhibition of neutrophil migration in mice by mouse formyl peptide receptors 1 and 2 dual agonist: indication ofcross-desensitization in vivo", Immunology, vol. 132(3), pp. 441-450 (2011).
Stepniewski et al., "Non-peptide ligand binding to the formyl peptide receptor FPR2-A comparison to peptide ligand binding modes", Bioorg Med Chem., vol. 23, pp. 4072-4081 (2015).
Summers et al., "Neutrophil kinetics in health and disease", Trends in Immunology, vol. 31(8), pp. 318-324 (2010).
Tae et al., "Airway Activation of Formyl Peptide Receptors Inhibits Th1and Th17 Cell Responses via Inhibition of Mediator Release from Immune and Inflammatory Cells and Maturation of Dendritic Cells", Journal of Immunology, vol. 188(4), pp. 1799-1808 (2012).
Wang et al., "Discovery of novel CDK8 inhibitors using multiple crystal structures indocking-based virtual screening", European Journal of Medicinal Chemistry, vol. 129, pp. 275-286 (2017).
Wong et al., "Pharmacokinetic Optimization of Class-Selective Histone Deacetylase Inhibitors and Identification of Associated Candidate Predictive Biomarkers of Hepatocellular Carcinoma Tumor Response", J. Med. Chem., vol. 55, pp. 8903-8925 (2012).

PHENYLPYRROLIDINONE FORMYL PEPTIDE 2 RECEPTOR AGONISTS

CROSS REFERENCE TO RELATED APPLICATIONS

This application is a continuation of U.S. patent application Ser. No. 16/291,209, filed Mar. 4, 2019, now allowed, which is entitled to priority pursuant to 35 U.S.C. § 119(e) to U.S. provisional patent application No. 62/638,556, filed Mar. 5, 2018, which is incorporated herein in its entirety.

BACKGROUND OF THE INVENTION

The present invention relates to novel pyrrolidinone compounds, which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to a small group of seven-transmembrane domain, G protein-coupled receptors that are expressed in multiple human tissues including immune cells and are known to be important in host defense and inflammation. FPR2 shares significant sequence homology with FPR1 and FPR3 (Journal of Autoimmunity 85, 2017, 64-77). Collectively, these receptors bind a number of structurally diverse agonists, including N-formyl and nonformyl peptides which act as chemo attractants and activate phagocytes. The endogenous peptide Annexin A1 and its N-terminal fragments are examples of ligands that bind human FPR1 and FPR2. Fatty acids such as eicosanoid, lipoxin A4, which belongs to a class of small pro-resolution mediators (SPMs), has also been identified as an agonist for FPR2 (Ye R D., et al., Pharmacol. Rev., 2009, 61, 119-61).

Endogenous FPR2 pro-resolution ligands, such as lipoxin A4 and Annexin A1, have been reported to trigger a wide array of cytoplasmatic cascades such as Gi coupling, $Ca^{2+}$ mobilization and β-arrestin recruitment. (Int J Mol Sci. 2013 April; 14(4): 7193-7230). FPR2 regulates both innate and adaptive immune systems including neutrophils, macrophages, T-, and B-cells. In neutrophils, FPR2 ligands modulate movement, cytotoxicity and life span. In macrophages, agonism of FPR2 prevents apoptosis and enhances efferocytosis. (Chandrasekharan J A, Sharma-Walia N, J. Inflamm. Res., 2015, 8, 181-92). The initiation of resolution of inflammation by FPR2 agonism is responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive loss of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 receptor with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, inflammatory bowel syndrome, Crohn's disease, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

SUMMARY OF THE INVENTION

The present invention provides novel pyrrolidinone, and their analogues thereof, which are useful as FPR2 agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in therapy.

The compounds of the invention may be used in the treatment and/or prophylaxis of multiple diseases or disorders associated with FPR2, such as inflammatory diseases, heart diseases, chronic airway diseases, cancers, septicemia, allergic symptoms, HIV retrovirus infection, circulatory disorders, neuroinflammation, nervous disorders, pains, prion diseases, amyloidosis, and immune disorders. The heart diseases are selected from the group consisting of angina pectoris, unstable angina, myocardial infarction, acute coronary disease, cardiac iatrogenic damage, and heart failure including, but not limited to, acute heart failure, chronic heart failure of ischemic and non-ischemic origin, systolic heart failure, diastolic heart failure, heart failure with reduced ejection fraction ($HF_REF$), and heart failure with preserved ejection fraction ($HF_PEF$).

The compounds of the invention can be used alone, in combination with other compounds of the present invention, or in combination with one or more other agent(s).

Other features and advantages of the invention will be apparent from the following detailed description and claims.

DESCRIPTION OF THE INVENTION

The invention encompasses compounds of Formula (I), which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of Formula (I):

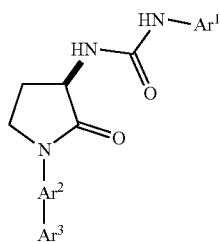

wherein:

$Ar^1$ is phenyl, pyridinyl, or pyridazinyl and is substituted with 1 halo, haloalkyl or haloalkoxy substituent in the 4-position and 0-2 additional halo or haloalkyl substituents;

$Ar^2$ is phenyl or pyridinyl substituted with 0-2 substituents selected from cyano, fluoro, alkyl, haloalkyl, cycloalkyl, alkoxy, and haloalkoxy;

$Ar^3$ is phenyl or pyridinyl and is substituted with 0-2 substituents selected from cyano, halo, hydroxyalkyl, alkoxyalkyl, $(R^1R^2N)$alkyl, $(alkyl)_2(O)P$, $(alkyl)(O)(NR^1)S$, alkylSO$_2$, and alkylSO$_2$NH;

$R^1$ is hydrogen or alkyl; and $R^2$ is hydrogen or alkyl; or $(R^1)(R^2)N$ taken together is azetidinyl, pyrrolidinyl, piperidinyl, piperazinyl, or morpholinyl and is substituted with 0-3 substituents selected from fluoro and alkyl; or a pharmaceutically acceptable salt thereof.

Another aspect of the invention is a compound of Formula (I) where $Ar^1$ is phenyl substituted with 1 halo, haloalkyl or haloalkoxy substituent in the 4-position and 0-2 additional halo or haloalkyl substituents.

Another aspect of the invention is a compound of Formula (I) where $Ar^2$ is phenyl substituted with 0 substituents, 1 alkyl or cycloalkyl substituent, or 2 fluoro substituents.

Another aspect of the invention is a compound of Formula (I) where $Ar^2$ is phenyl substituted with 0 substituents or 2 fluoro substituents.

Another aspect of the invention is a compound of Formula (I) where $Ar^3$ is phenyl substituted with 1-2 substituents selected from cyano, halo, hydroxyalkyl, alkoxyalkyl, $(R^1R^2N)$alkyl, $(alkyl)_2(O)P$, $(alkyl)(O)(NR^1)S$, alkylSO$_2$, and alkylSO$_2$NH.

Another aspect of the invention is a compound of Formula (I) where $R^1$ is hydrogen and $R^2$ is hydrogen.

Another aspect of the invention is a compound of Formula (II):

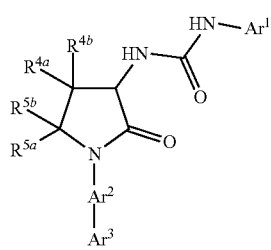

or a pharmaceutically acceptable salt thereof, wherein:

$Ar^1$ is aryl substituted with 1-2 $R^{1a}$ and 1-2 $R^{1b}$ or monocyclic heteroaryl with 1-3 heteroatoms selected from nitrogen, oxygen, and sulfur, and substituted with 1-2 $R^{1a}$ and 1-2 $R^{1b}$;

$Ar^2$ is aryl substituted with 1-4 $R^{2a}$ or 6-membered heteroaryl with 1-2 nitrogen atoms, and substituted with 1-4 $R^{2a}$;

$Ar^3$ is aryl substituted with 1-4 $R^{3a}$ or monocyclic heteroaryl with 1-3 heteroatoms selected from nitrogen, oxygen, and sulfur, and substituted with 1-4 $R^{3a}$;

$R^{1a}$ is hydrogen or halo;

$R^{1b}$ is halo, haloalkyl, alkoxy, or haloalkoxy;

$R^{2a}$ is hydrogen, cyano, halo, alkyl, hydroxyalkyl, haloalkyl, cycloalkyl, alkoxy, or haloalkoxy; alternatively, two adjacent $R^{2a}$ groups are taken together with the carbon atoms to which they are attached to form a heterocycle with 1-4 heteroatoms selected from nitrogen, oxygen, and sulfur;

$R^{3a}$ is cyano, halo, alkyl, alkoxy, hydroxyalkyl, alkoxyalkyl, haloalkyl, $(R^1R^2N)$alkyl, $R^1R^2N$, alkylC(O)(R$^2$)Nalkyl, $(alkyl)_2(O)P$, $(alkoxy)_2(O)P$, $(alkoxy)(alkyl)(O)P$, $(alkyl)(O)(NR^1)S$, alkylSO$_2$, or alkylSO$_2$NH; alternatively, two adjacent $R^{3a}$ groups are taken together with the carbon atoms to which they are attached to form a heterocycle with 1-4 heteroatoms selected from nitrogen, oxygen, and sulfur;

$R^{4a}$ or $R^{4b}$ is independently hydrogen, alkyl, alkoxy, hydroxylalkyl, alkoxyalkyl, or haloalkoxy; alternatively, $R^{4a}$ and $R^{4b}$ together with the carbon atom they are both attached to form a $C_{3-6}$ cycloalkyl;

$R^{5a}$ or $R^{5b}$ is independently hydrogen, alkyl, hydroxylalkyl, alkoxyalkyl or haloalkoxyl;

$R^1$ is hydrogen or alkyl; and $R^2$ is hydrogen or alkyl; or $R^1R^2N$ taken together is azetidinyl, oxazolyl pyrrolidinyl, piperidinyl, piperazinyl, or morpholinyl, and is substituted with 0-3 substituents selected from halo, alkyl, and oxo.

Another aspect of the invention is a compound of Formula (III):

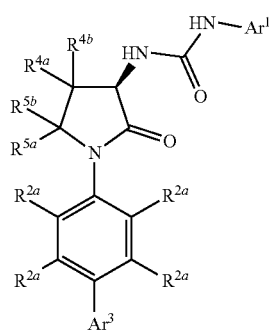

or a pharmaceutically acceptable salt thereof, wherein:

$Ar^1$ is phenyl substituted with 1-2 $R^{1a}$ and 1-2 $R^{1b}$ or 6-membered heteroaryl with 1-3 nitrogen atoms and substituted with 1$R^{1a}$ and 1-2 $R^{1b}$;

$Ar^3$ is phenyl substituted with 1-3 $R^{3a}$ or 5- to 6-membered heteroaryl with 1-3 nitrogen atoms and substituted with 1-3 $R^{3a}$;

$R^{1a}$ is hydrogen or halo;

$R^{1b}$ is halo, $C_{1-4}$ haloalkyl, $C_{1-4}$ alkoxy, or $C_{1-4}$ haloalkoxy;

$R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy;

$R^{3a}$ is cyano, halo, $C_{1-4}$ alkyl, $C_{1-4}$ hydroxyalkyl, $C_{1-4}$ alkoxyalkyl, $C_{1-4}$ haloalkyl, $(R^1R^2N)C_{1-4}$ alkyl, $R^1R^2N$, $C_{1-4}$ alkylC(O)($R^2$)N$C_{1-4}$ alkyl, $(C_{1-4}$ alkyl$)_2$(O)P, $(C_{1-4}$ alkoxy$)_2$(O)P, $(C_{1-4}$ alkoxy)($C_{1-4}$ alkyl)(O)P, $C_{1-4}$ alkylSO$_2$, or $C_{1-4}$ alkylSO$_2$NH;

$R^1R^2N$ taken together is oxazolyl or pyrrolidinyl and is substituted with 0-3 substituents selected from halo, alkyl, and oxo;

$R^{4a}$ or $R^{4b}$ is independently hydrogen, $C_{1-4}$ alkyl, or $C_{1-4}$ hydroxyalkyl; alternatively, $R^{4a}$ and $R^{4b}$ together with the carbon atom they are both attached to form a $C_{3-6}$ cycloalkyl; and $R^{5a}$ or $R^{5b}$ is independently hydrogen, $C_{1-4}$ alkyl, $C_{1-4}$ hydroxylalkyl, or $C_{1-4}$ alkoxyalkyl.

Another aspect of the invention is a compound of Formula (II) or (III), or a pharmaceutically acceptable salt thereof, wherein:

$Ar^1$ is phenyl substituted with 1-2 $R^{1a}$ and 1-2 $R^{1b}$, pyridinyl substituted with 1 $R^{1a}$ and 1-2 $R^{1b}$, or pyrazinyl substituted with 1$R^{1a}$ and 1-2 $R^{1b}$; and $Ar^3$ is phenyl substituted with 1-3 $R^{3a}$, pyrazolyl substituted with 1-3 $R^{3a}$, pyridinyl substituted with 1-3 $R^{3a}$, or pyrimidinyl substituted with 1-3 $R^{3a}$.

Another aspect of the invention is a compound of Formula (IV):

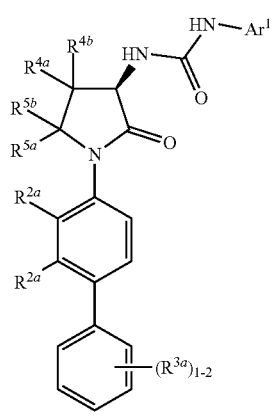

(IV)

or a pharmaceutically acceptable salt thereof, wherein:

$Ar^1$ is phenyl substituted with 1-2 $R^{1a}$ and 1-2 $R^{1b}$, pyridinyl substituted with 1 $R^{1a}$ and 1-2 $R^{1b}$, or pyrazinyl substituted with 1 $R^{1a}$ and 1-2 $R^{1b}$;

$R^{1a}$ is hydrogen or halo;

$R^{1b}$ is halo, $C_{1-4}$ haloalkyl, $C_{1-4}$ alkoxy, or $C_{1-4}$ haloalkoxy;

$R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy;

$R^{3a}$ is cyano, halo, $C_{1-3}$ alkyl, $C_{1-3}$ hydroxyalkyl, $C_{1-3}$ alkoxyalkyl, $C_{1-3}$ haloalkyl, $R^1R^2N$, $(C_{1-3}$ alkyl$)_2$(O)P, $(C_{1-3}$ alkoxy$)_2$(O)P, $(C_{1-3}$ alkoxy)($C_{1-3}$ alkyl)(O)P, $C_{1-3}$ alkylSO$_2$, or $C_{1-3}$ alkylSO$_2$NH;

$R^{4a}$ or $R^{4b}$ is independently hydrogen, $C_{1-3}$ alkyl, or $C_{1-3}$ hydroxylalkyl; alternatively, $R^{4a}$ and $R^{4b}$ together with the carbon atom they are both attached to form a $C_{3-6}$ cycloalkyl; and $R^{5a}$ or $R^{5b}$ is independently hydrogen, $C_{1-3}$ alkyl, $C_{1-3}$ hydroxylalkyl, or $C_{1-3}$ alkoxyalkyl.

Another aspect of the invention is a compound of Formula (V):

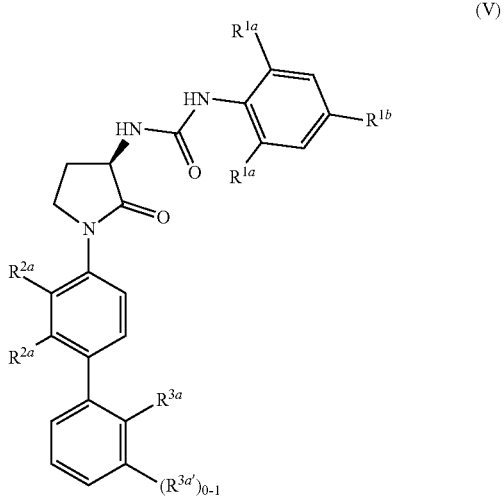

(V)

or a pharmaceutically acceptable salt thereof, wherein:

$R^{1a}$ is hydrogen or F;

$R^{1b}$ is halo, $C_{1-2}$ haloalkyl, or $C_{1-2}$ alkoxy;

$R^{2a}$ is hydrogen, halo, $C_{1-3}$ alkyl, $C_{1-3}$ haloalkyl, or $C_{3-6}$ cycloalkyl;

$R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)($C_{1-2}$ alkyl)(O)P, $C_{1-2}$ alkylSO$_2$, or $C_{1-2}$ alkylSO$_2$NH; and $R^{3a'}$ is halo.

Another aspect of the invention is a compound of Formula (V), or a pharmaceutically acceptable salt thereof, wherein:

$R^{1a}$ is hydrogen or F;

$R^{1b}$ is F, Cl, or CF$_3$;

$R^{2a}$ is hydrogen, F, Cl, isopropyl, CF$_3$, or cyclopropyl;

$R^{3a}$ is $(CH_3)_2$(O)P, $(CH_3CH_2)_2$(O)P, $(CH_3CH_2O)(CH_3)$(O)P, $CH_3SO_2$, or $CH_3SO_2NH$; and $R^{3a'}$ is F.

Another aspect of the invention is a compound of Formula (VI):

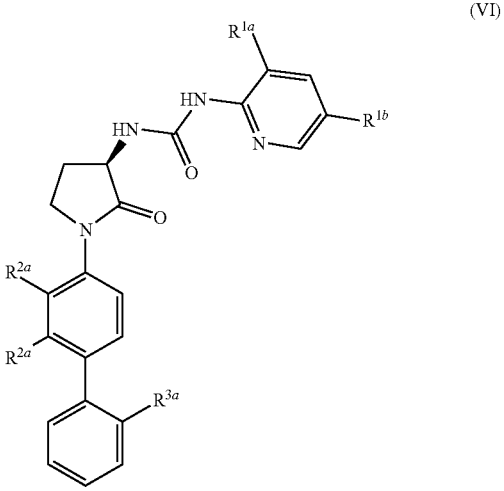

(VI)

or a pharmaceutically acceptable salt thereof, wherein:
$R^{1a}$ is hydrogen or halo;
$R^{1b}$ is halo, $C_{1-2}$ haloalkyl, or $C_{1-2}$ alkoxy;
$R^{2a}$ is hydrogen, halo, $C_{1-3}$ alkyl, or $C_{3-6}$ cycloalkyl;
$R^{3a}$ is $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

Another aspect of the invention is a compound of Formula (VII):

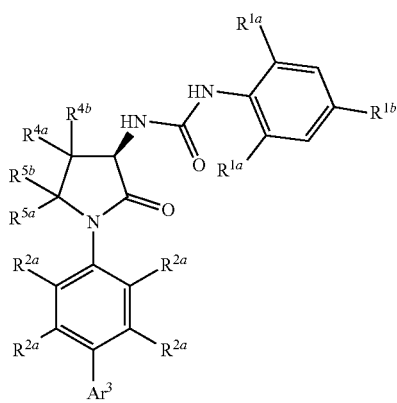

(VII)

or a pharmaceutically acceptable salt thereof, wherein:
Ar$^3$ is pyrazolyl substituted with 1-3 $R^{3a}$, pyridinyl substituted with 1-3 $R^{3a}$, or pyrimidinyl substituted with 1-3 $R^{3a}$;
$R^{1a}$ is hydrogen or halo;
$R^{1b}$ is halo, $C_{1-4}$ haloalkyl, $C_{1-4}$ alkoxy, or $C_{1-4}$ haloalkoxy;
$R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy;
$R^{3a}$ is cyano, halo, $C_{1-4}$ alkyl, $C_{1-4}$ hydroxyalkyl, $C_{1-4}$ alkoxyalkyl, $(R^1R^2N)C_{1-4}$ alkyl, $R^1R^2N$—, $(C_{1-4}$ alkyl$)_2$(O)P, $(C_{1-4}$ alkoxy$)_2$(O)P, $(C_{1-4}$ alkoxy)$(C_{1-4}$ alkyl)(O)P, $C_{1-4}$ alkylSO$_2$, or $C_{1-4}$ alkylSO$_2$NH;
$R^1$ is hydrogen or alkyl;
$R^2$ is hydrogen or alkyl; or $R^1R^2N$ taken together is oxazolyl or pyrrolidinyl, and is substituted with 0-3 substituents selected from halo, alkyl, or oxo;
$R^{4a}$ or $R^{4b}$ is independently hydrogen, $C_{1-4}$ alkyl, $C_{1-4}$ alkoxy, $C_{1-4}$ alkoxyalkyl, or $C_{1-4}$ haloalkoxy; $R^{4a}$ and $R^{4b}$ together with the carbon atom to which they are both attached form a $C_{3-6}$ cycloalkyl; and
$R^{5a}$ or $R^{5b}$ is independently hydrogen, $C_{1-4}$ alkyl, $C_{1-4}$ alkoxy, $C_{1-4}$ alkoxyalkyl, or $C_{1-4}$ haloalkoxy.

Another aspect of the invention is a compound of Formula (VIII):

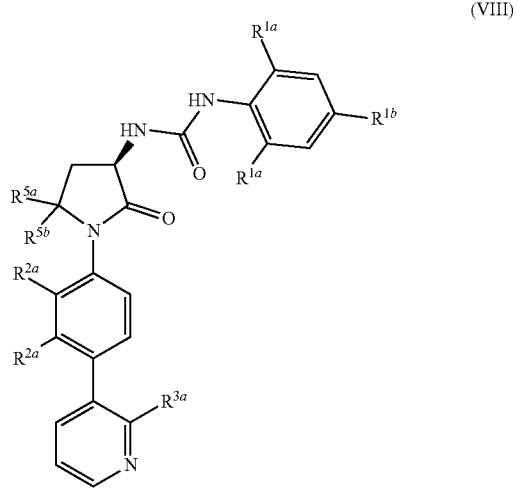

(VIII)

or a pharmaceutically acceptable salt thereof, wherein:
$R^{1a}$ is hydrogen or halo;
$R^{1b}$ is halo, $C_{1-2}$ haloalkyl, or $C_{1-2}$ alkoxy;
$R^{2a}$ is hydrogen, halo, $C_{1-3}$ alkyl, or $C_{3-6}$ cycloalkyl;
$R^{3a}$ is $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH; and
$R^{5a}$ or $R^{5b}$ is independently hydrogen or $C_{1-2}$ alkyl.

Another aspect of the invention is a compound of Formula (IX):

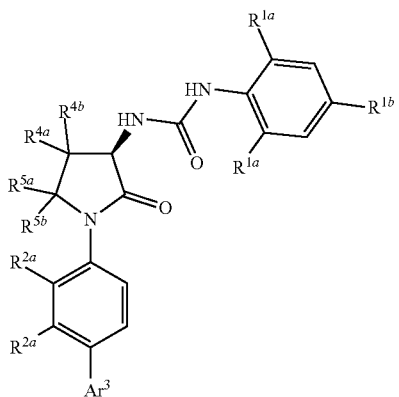

(IX)

or a pharmaceutically acceptable salt thereof, wherein:
$R^{1a}$ is hydrogen or halo;
$R^{1b}$ is halo, $C_{1-2}$ haloalkyl, or $C_{1-2}$ alkoxy;
$R^{2a}$ is hydrogen, halo, $C_{1-2}$ haloalkyl, $C_{1-3}$ alkyl, or $C_{3-6}$ cycloalkyl;
Ar$^3$ is

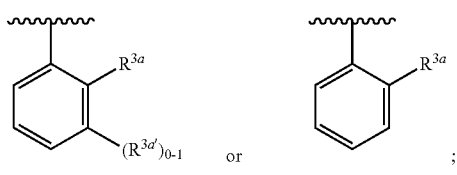

$R^{3a}$ is $(C_{1-2}$ alkyl$)_2$(O)P, $(C_{1-2}$ alkoxy)$(C_{1-2}$ alkyl)(O)P, or $C_{1-2}$ alkylSO$_2$NH;

$R^{3a'}$ is halo;

$R^{4a}$ or $R^{4b}$ is independently hydrogen, $C_{1-2}$ alkyl, or $C_{1-2}$ hydroxyalkyl; or $R^{4a}$ and $R^{4b}$ together with the carbon atom to which they are both attached form a $C_{3-6}$ cycloalkyl; and $R^{5a}$ or $R^{5b}$ is independently hydrogen, $C_{1-2}$ alkyl, $C_{1-2}$ hydroxyalkyl, or $C_{1-2}$ alkoxyalkyl.

Another aspect of the invention is a compound of Formula (II), (III), (IV), (VII), or (IX), or a pharmaceutically acceptable salt thereof, wherein:

$R^{4a}$ is hydrogen;

$R^{4b}$ is hydrogen;

$R^{5a}$ is $C_{1-2}$ alkyl, $C_{1-2}$ hydroxylalkyl, or $C_{1-2}$ alkoxyalkyl; and $R^{5b}$ is hydrogen.

Another aspect of the invention is a compound of formula (II), (III), (IV), (VII), or (IX), or a pharmaceutically acceptable salt thereof, wherein:

$R^{4a}$ is $C_{1-2}$ alkyl;

$R^{4b}$ is $C_{1-2}$ alkyl; or $R^{4a}$ and $R^{4b}$ are taken together to form a cyclopropyl;

$R^{5a}$ is hydrogen; and $R^{5b}$ is hydrogen.

Another aspect of the invention is a compound selected from the group consisting of

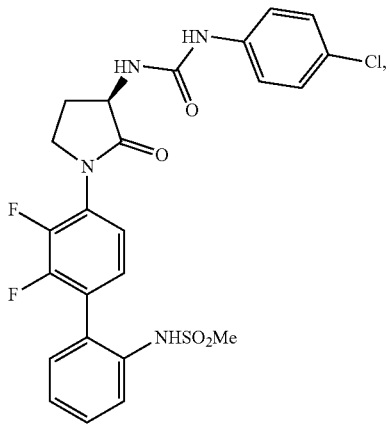

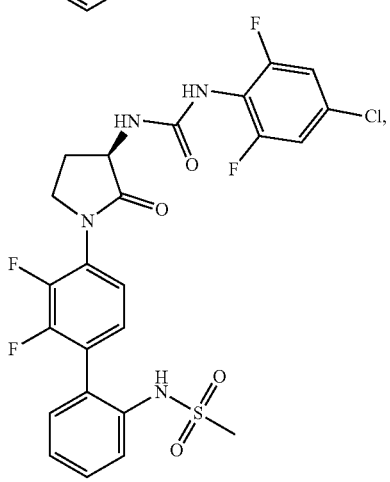

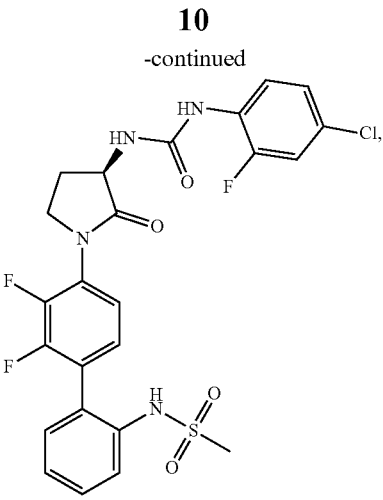

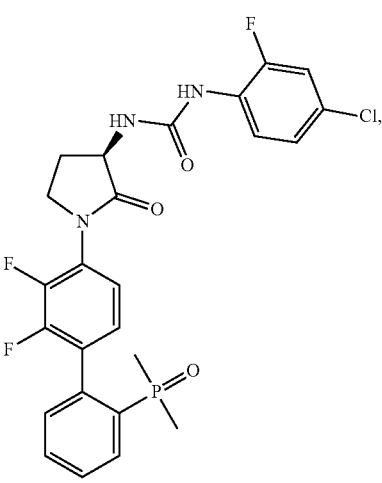

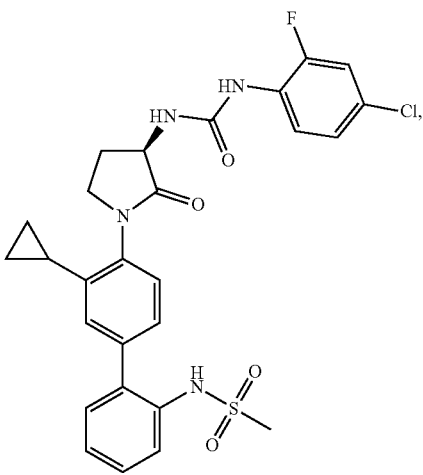

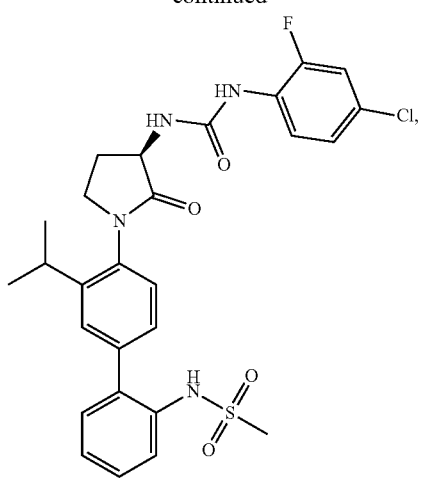
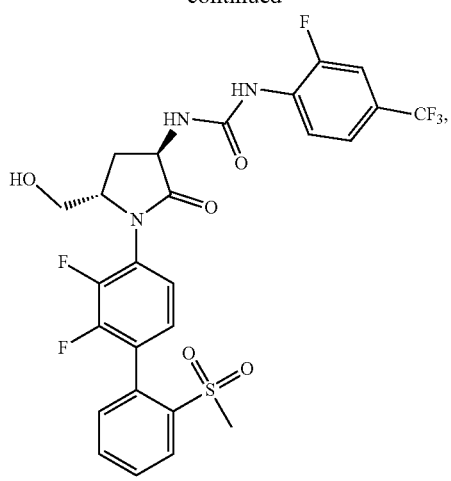
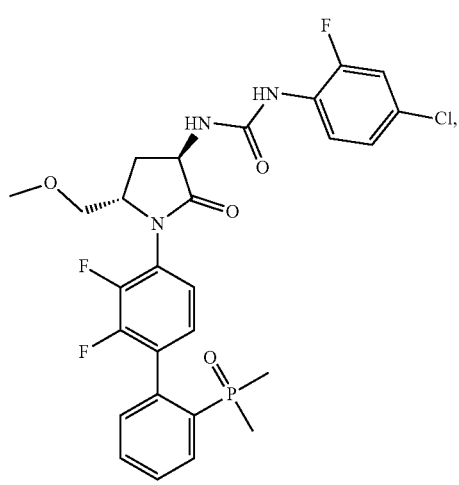
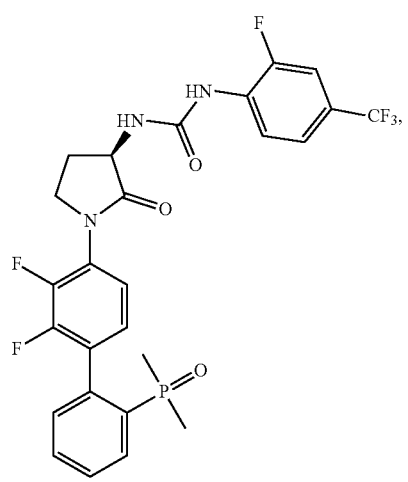
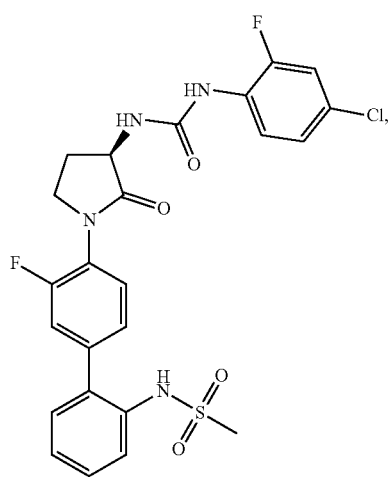
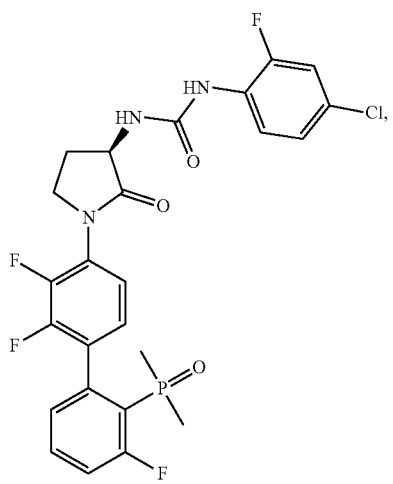

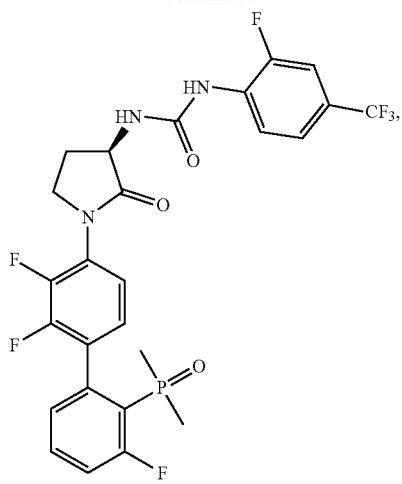
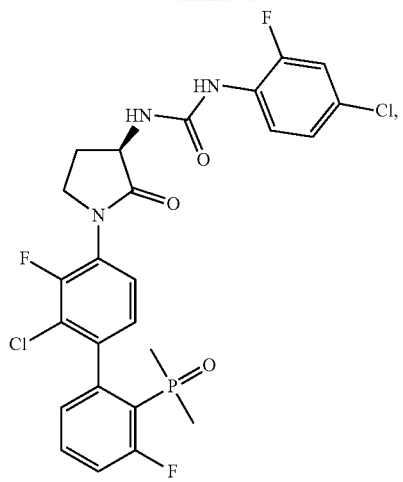
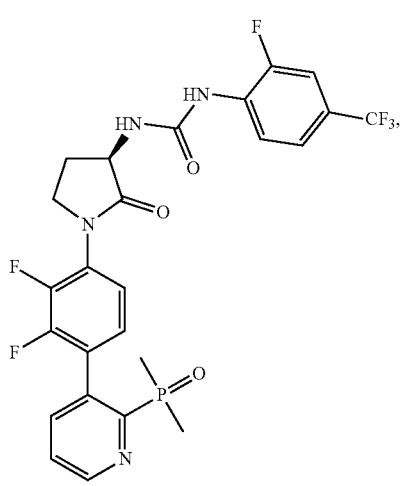
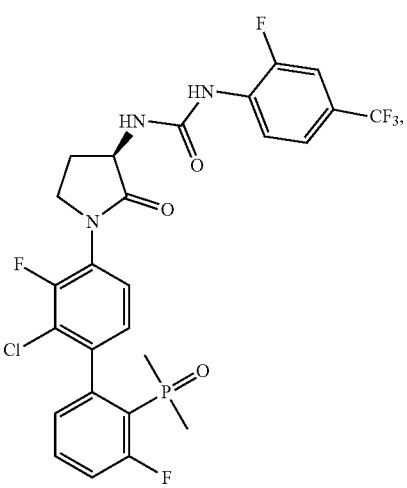
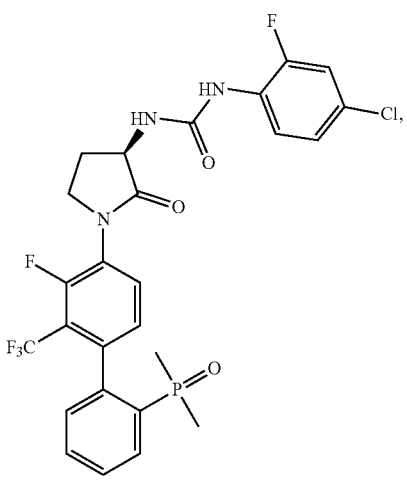
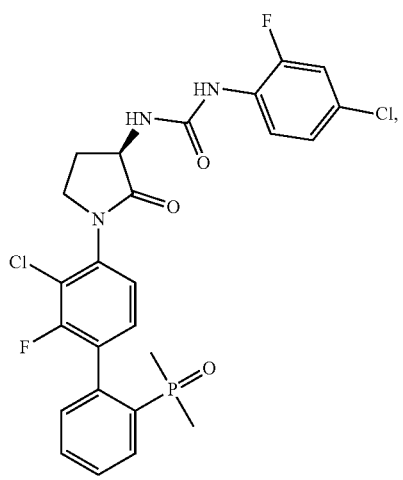

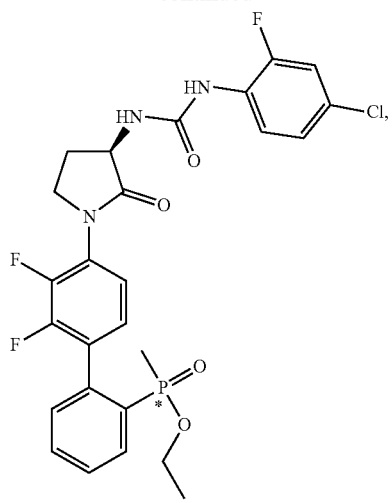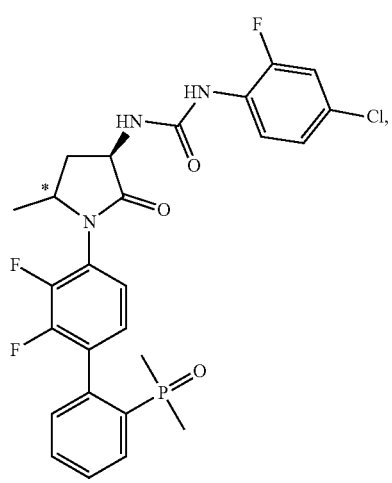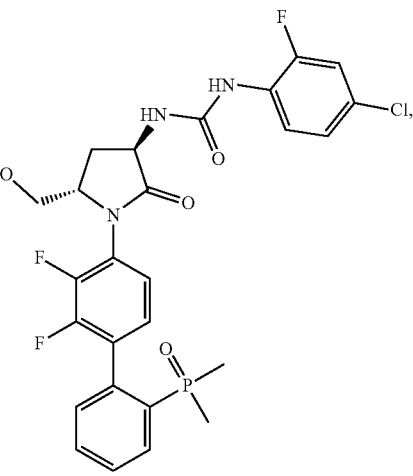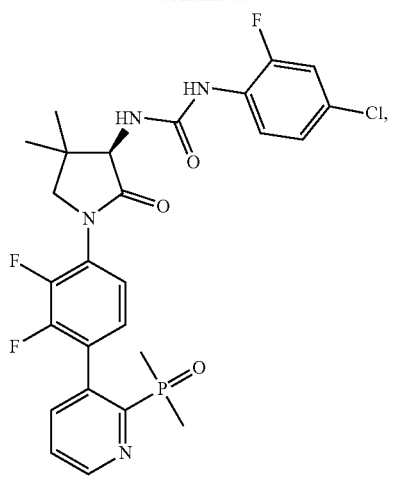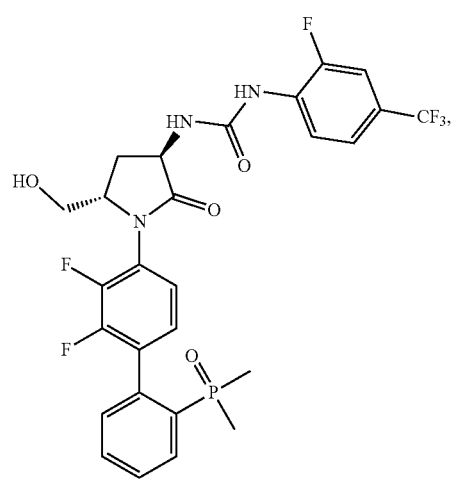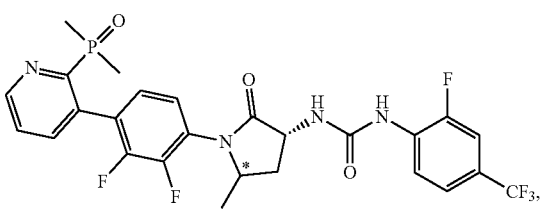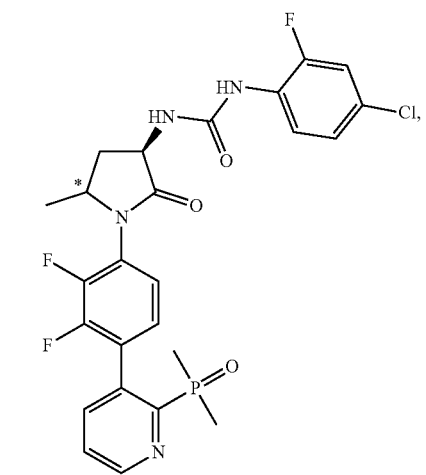

-continued

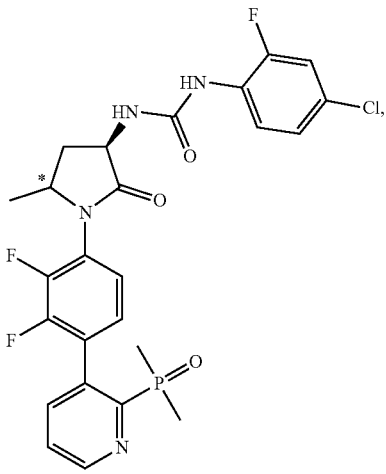

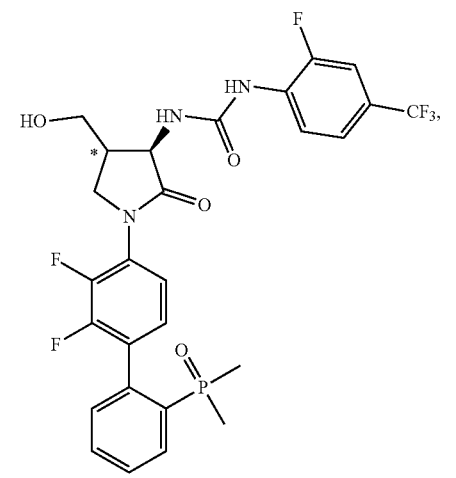

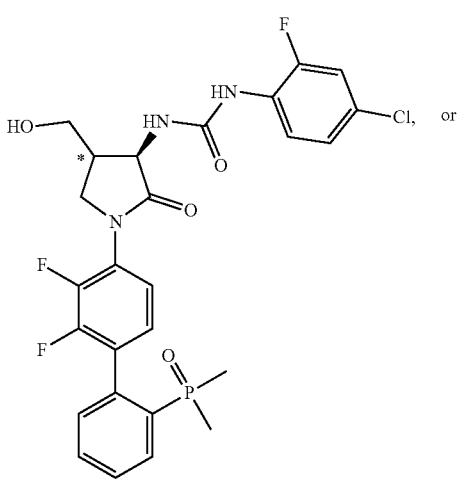

-continued

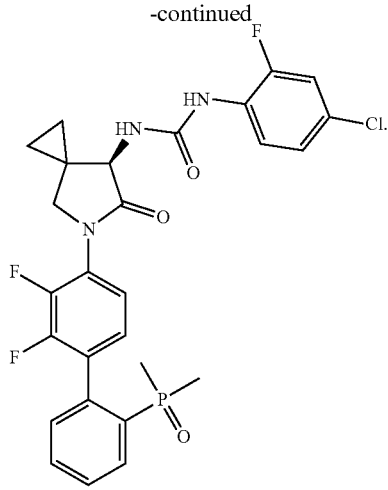

For a compound of Formula (I), (II), (III), (IV), (V), (VI), (VII), (VIII), or (IX), the scope of any instance of a variable substituent, including $Ar^1$, $Ar^2$, $Ar^3$, $R^{1a}$, $R^{1b}$, $R^{2a}$, $R^{3a}$, $R^{4a}$, $R^{4b}$, $R^{5a}$, $R^{5b}$, $R^1$, $R^2$ can be used independently with the scope of any other instance of a variable substituent. As such, the invention includes combinations of the different aspects.

In one non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is phenyl, pyridinyl, or pyrazinyl, each substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is phenyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is phenyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is phenyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$, $R^{4b}$, $R^{5a}$, $R^{5b}$ are all hydrogen; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In one non-limiting embodiment, for a compound of Formula (II), (III), (IV), (VII), or (IX), $R^{4a}$ is methyl, $R^{4b}$ is methyl; or $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is phenyl, pyridinyl, or pyrazinyl, each substituted with 1$R^{1a}$ and 1-2 $R^{1b}$; $R^{a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; or $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is phenyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is phenyl substituted with 1$R^{1a}$ and 1-2 $R^{1b}$; $R^{1a}$ is hydrogen or halo; $R^{b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy$)(C_{1-2}$ alkyl$)$(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is phenyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyridinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyridinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyridinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyridinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyrazinyl substituted with $1R^{1a}$ and 1-2 $R^b$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyrazinyl substituted with $1R^{1a}$ and 1-2 $R^{1b}$; $R^{1a}$ is hydrogen or halo; $R^b$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyrazinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ is methyl, $R^{4b}$ is methyl; $R^{4a}$ is hydrogen, $R^{4b}$ is hydroxymethyl; or $R^{4a}$ and $R^{4b}$ are taken together to form a cyclopropyl; $R^{5a}$ and $R^{5b}$ are all hydrogen; $Ar^1$ is pyrazinyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In one non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is phenyl, pyridinyl, or pyrazinyl, each substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2(O)P$, $(C_{1-2}$ alkoxy$)_2(O)P$, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is phenyl substituted with $1R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is phenyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is phenyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl, pyrazolyl, pyridinyl, or pyrimidinyl, each substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyridinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is phenyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrazolyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyridinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In another non-limiting embodiment, for a compound of Formula (II), (III), (IV), (VII), or (IX), $R^{4a}$ and $R^{4b}$ are all hydrogen; $R^{5a}$ is hydrogen, $R^{5b}$ is methyl or hydroxymethyl; $Ar^1$ is pyrazinyl substituted with 1$R^{1a}$ and 1-2 $R^{1b}$; $R^{1a}$ is hydrogen or halo; $R^{1b}$ is halo, $C_{1-2}$ haloalkyl, or $C_{1-2}$ alkoxy; $Ar^2$ is phenyl substituted with 1-4 $R^{2a}$; $R^{2a}$ is hydrogen, halo, $C_{1-4}$ alkyl, $C_{1-4}$ hydroxyalkyl, $C_{1-4}$ haloalkyl, $C_{3-6}$ cycloalkyl, $C_{1-4}$ alkoxy, or $C_{1-4}$ haloalkoxy; $Ar^3$ is pyrimidinyl substituted with 1-4 $R^{3a}$; $R^{3a}$ is halo, hydroxyalkyl, alkoxyalkyl, $(C_{1-2}$ alkyl$)_2$(O)P, $(C_{1-2}$ alkoxy$)_2$(O)P, $(C_{1-2}$ alkoxy)$(C_{1-2}$ alkyl)(O)P, $C_{1-2}$ alkylSO$_2$, or $C_{1-2}$ alkylSO$_2$NH.

In one preferred embodiment, for a compound of Formula (II), (III), (IV), or (VII), or (IX), $R^{4a}$ is methyl; $R^{4b}$ is methyl; $R^{4a}$ is hydrogen; $R^{4b}$ is hydroxymethyl; or $R^{4a}$ and $R^{4b}$ are taken together to form a cyclopropyl; $R^{5a}$ is hydrogen, $R^{5b}$ is methyl or hydroxymethyl; $R^{5a}$ is hydrogen; $R^{5b}$ is hydrogen; or $R^{4a}$, $R^{4b}$, $R^{5a}$, $R^{5b}$ are all hydrogen; $Ar^1$ is phenyl substituted with 1$R^{1a}$ and 1-2 $R^{1b}$; $R^{1a}$ is hydrogen, or F; $R^{1b}$ is F, Cl, or CF$_3$; $Ar^2$ is phenyl substituted with 1-2 $R^{2a}$; $R^{2a}$ is hydrogen, F, Cl, isopropyl, CF$_3$CF$_3$, cyclopropyl; $Ar^3$ is phenyl or pyridinyl, each substituted with 1-2 $R^{3a}$; $R^{3a}$ is F, (CH$_3$)$_2$(O)P, (CH$_3$CH$_2$)$_2$(O)P, (CH$_3$CH$_2$O)(CH$_3$)(O)P, CH$_3$SO$_2$, or CH$_3$SO$_2$NH.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms including the structure below with the indicated carbon. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemoattractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, $Ca^{2+}$ mobilization and transcription. The family interacts with a diverse set of ligands that includes proteins, polypeptides and fatty acid metabolites which activate both pro-inflammatory and pro-resolution downstream responses. FPR2 and FPR1 Cyclic Adenosine Monophosphate (cAMP) Assays were used to measure the activity of the compounds in this patent.

FPR2 and FPR1 Cyclic Adenosine Monophosphate (cAMP) Assays. A mixture of forskolin (5 µM final for FPR2 or 10 µM final for FPR1) and IBMX (200 µM final) were added to 384-well Proxiplates (Perkin-Elmer) pre-dotted with test compounds in DMSO (1% final) at final concentrations in the range of 0.020 nM to 100 µM. Chinese Hamster Ovary cells (CHO) overexpressing human FPR1 or human FPR2 receptors were cultured in F-12 (Ham's) medium supplemented with 10% qualified FBS, 250 µg/ml zeocin and 300 µg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 µM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. Table 1 below lists $EC_{50}$ values in the FPR2 and FPR1 cAMP assays measured for the following examples.

TABLE 1

| Example | hFPR2 cAMP2 EC$_{50}$ (μM) | hFPR1 cAMP EC$_{50}$ (μM) |
| --- | --- | --- |
| 1 | 0.00043 | 0.20 |
| 2 | 0.0042 | 0.36 |
| 3 | 0.0011 | 0.22 |
| 4 | 0.00093 | 1.7 |
| 5 | 0.00068 | 0.23 |
| 6 | 0.0010 | 0.19 |
| 7 | 0.0021 | 0.14 |
| 8 | 0.0020 | 0.061 |
| 9 | 0.0021 | 0.031 |
| 10 | 0.0022 | 0.13 |
| 11 | 0.0026 | 0.29 |
| 12 | 0.0025 | 0.45 |
| 13 | 0.0065 | 2.5 |
| 14 | 0.0072 | 0.60 |
| 15 | 0.010 | 1.5 |
| 16 | 0.012 | 0.12 |
| 17 | 0.016 | 4.1 |
| 18 | 0.020 | 2.1 |
| 19 | 0.022 | 0.078 |
| 20 | 0.024 | >10 |
| 21 | 0.031 | 0.39 |
| 22 | 0.033 | 1.5 |
| 23 | 0.0082 | 0.70 |
| 24 | 0.022 | 1.4 |
| 25 | 0.00053 | 0.26 |
| 26 | 0.00055 | 0.047 |
| 27 | 0.00050 | 0.11 |
| 28 | 0.0098 | 0.55 |
| 29 | 0.0070 | 0.19 |
| 30 | 0.00022 | 0.083 |
| 31 | 0.0040 | 0.43 |
| 32 | 0.00091 | 0.25 |
| 33 | 0.0011 | 0.47 |
| 34 | 0.0041 | 0.026 |
| 35 | 0.0086 | 0.052 |
| 36 | 0.0047 | 0.069 |
| 37 | 0.00140 | 0.17 |
| 38 | 0.0035 | 0.042 |
| 39 | 0.00058 | 0.057 |
| 40 | 0.0046 | 0.050 |
| 41 | 0.0036 | 0.50 |
| 42 | 0.0010 | 0.22 |
| 43 | 0.0033 | 0.12 |
| 44 | 0.043 | 0.45 |
| 45 | 0.0030 | 0.14 |
| 46 | 0.0048 | 0.093 |
| 47 | 0.0028 | 0.064 |
| 48 | 0.0037 | 0.11 |
| 49 | 0.0056 | 3.4 |
| 50 | 0.014 | 0.64 |
| 51 | 0.0082 | 1.3 |
| 52 | 0.010 | 1.1 |
| 53 | 0.0078 | 2.7 |
| 54 | 0.0055 | 0.90 |
| 55 | 0.022 | >10 |
| 56 | 0.0075 | 7.7 |
| 57 | 0.00095 | 1.0 |
| 58 | 0.0063 | 0.61 |
| 59 | 0.0017 | 0.14 |
| 60 | 0.0037 | 0.12 |
| 61 | 0.023 | 0.37 |
| 62 | 0.031 | 0.72 |
| 63 | 0.00567 | 4.4 |
| 64 | 0.0088 | 2.9 |
| 65 | 0.0012 | 2.6 |
| 66 | 0.0049 | 0.58 |
| 67 | 0.00248 | 1.3 |
| 68 | 0.00053 | 0.15 |
| 69 | 0.022 | 5.0 |
| 70 | 0.000077 | 0.020 |
| 71 | 0.0021 | 1.28 |
| 72 | 0.00061 | 0.054 |
| 73 | 0.00089 | 0.17 |
| 74 | 0.0022 | 0.14 |
| 75 | 0.0034 | 1.18 |
| 76 | 0.0041 | 2.1 |
| 77 | 0.0012 | 0.079 |
| 78 | 0.0012 | 0.045 |
| 79 | 0.039 | >10 |
| 80 | 0.0014 | 0.086 |
| 81 | 0.00052 | 0.027 |
| 82 | 0.0025 | 0.78 |
| 83 | 0.00041 | 0.00099 |
| 84 | 0.0060 | 0.28 |
| 85 | 0.00062 | 0.0051 |
| 86 | 0.00085 | 0.021 |
| 87 | 0.0016 | 0.0012 |
| 88 | 0.0053 | 0.0049 |
| 89 | 0.0044 | 0.025 |
| 90 | 0.0051 | 1.4 |
| 91 | 0.0057 | 0.20 |
| 92 | 0.0083 | 0.22 |
| 93 | 0.012 | 0.78 |
| 94 | 0.0018 | 0.012 |
| 95 | 0.032 | 0.20 |
| 96 | 0.0029 | 0.075 |
| 97 | 0.0072 | 0.11 |
| 98 | 0.0029 | 0.27 |
| 99 | 0.00079 | 0.24 |
| 100 | 0.0020 | 0.092 |
| 101 | 0.00066 | 0.0011 |
| 102 | 0.0017 | 0.57 |
| 103 | 0.00057 | 0.35 |
| 104 | 0.0052 | 0.049 |
| 105 | 0.0069 | 0.071 |
| 106 | 0.0031 | 0.0035 |
| 107 | 0.011 | 0.0058 |
| 108 | 0.0014 | 0.053 |
| 109 | 0.00044 | 0.39 |
| 110 | 0.0011 | 0.64 |
| 111 | 0.030 | 0.54 |
| 112 | 0.00027 | 0.39 |
| 113 | 0.00039 | 0.59 |
| 114 | 0.00086 | 0.27 |
| 115 | 0.0012 | 0.055 |
| 116 | 0.00121 | 0.89 |
| 117 | 0.013 | 0.084 |
| 118 | 0.017 | 0.32 |
| 119 | 0.014 | 0.19 |
| 120 | 0.00078 | 0.16 |
| 121 | 0.00030 | 0.0050 |
| 122 | 0.00081 | 0.61 |
| 123 | 0.0015 | 0.24 |
| 124 | 0.00079 | 0.76 |
| 125 | 0.00099 | 0.18 |
| 126 | 0.012 | >10 |
| 127 | 0.018 | 0.92 |
| 128 | 0.0010 | 0.024 |
| 129 | 0.0024 | 0.019 |
| 130 | 0.0057 | 3.0 |
| 131 | 0.0012 | 0.061 |
| 132 | 0.00048 | 0.028 |
| 133 | 0.15 | >5 |
| 134 | 0.0025 | 1500 |
| 135 | 0.0029 | 720 |

Pharmaceutical Compositions and Methods of Use

The compounds of the present invention may be administered to mammals, preferably humans, for the treatment of a variety of conditions and disorders associated with the FPR2 receptor such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, heart failure, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic fibrosis, kidney fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, rhinitis, atherosclerosis, neuroinflammatory diseases including multiple sclerosis, stroke, sepsis, and the like.

Unless otherwise specified, the following terms have the stated meanings. The term "subject" refers to any human or other mammalian species that could potentially benefit from treatment with a FPR2 and/or FPR1 agonist as understood by practitioners in this field. Some subjects include human beings of any age with risk factors for cardiovascular disease. Common risk factors include age, sex, weight, family history, sleep apnea, alcohol or tobacco use, physical inactivity arrthymia or signs of insulin resistance such as *Acanthosis nigricans*, hypertension, dyslipidemia, or polycystic ovary syndrome (PCOS). The term "patient" means a person suitable for therapy as determined by practitioners in the field. "Treating" or "treatment" cover the treatment of a patient or subject as understood by practitioners in this field. "Preventing" or "prevention" cover the preventive treatment (i.e., prophylaxis and/or risk reduction) of a subclinical disease-state in a patient or subject aimed at reducing the probability of the occurrence of a clinical disease-state as understood by practitioners in this field. Patients are selected for preventative therapy based on factors that are known to increase risk of suffering a clinical disease state compared to the general population. "Therapeutically effective amount" means an amount of a compound that is effective as understood by practitioners in this field.

Another aspect of the invention are pharmaceutical compositions comprising a therapeutically effective amount of a compound of Formulae (I)-(IX) in combination with a pharmaceutical carrier.

Another aspect of the invention are pharmaceutical compositions comprising a therapeutically effective amount of a compound of Formulae (I)-(IX) in combination with at least one other therapeutic agent and a pharmaceutical carrier.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Another aspect of the invention is a method for treating heart disease comprising administering a therapeutically effective amount of a compound of Formula (I) to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

It will be understood that treatment or prophylaxis of heart failure may involve treatment or prophylaxis of a cardiovascular event as well. Treatment or prophylaxis as referred to herein may refer to treatment or prophylaxis of certain negative symptoms or conditions associated with or arising as a result of a cardiovascular event. By way of example, treatment or prophylaxis may involve reducing or preventing negative changes in fractional shortening, heart weight, lung weight, myocyte cross sectional area, pressure overload induced cardiac fibrosis, stress induced cellular senescence, and/or cardiac hypertrophy properties, or any combination thereof, associated with or arising as a result of a cardiovascular event. Treatment may be administered in preparation for or in response to a cardiovascular event to alleviate negative effects. Prevention may involve a pro-active or prophylactic type of treatment to prevent the cardiovascular event or to reduce the onset of negative effects of a cardiovascular event.

In one embodiment, the present invention provides the use of compounds of Formulae (I)-(IX) or a pharmaceutically acceptable salt thereof for the preparation of a pharmaceutical composition for the treatment or prophylaxis of heart failure, for example, heart failure results from hypertension, an ischemic heart disease, a non-ischemic heart disease, exposure to a cardiotoxic compound, myocarditis, Kawasaki's disease, Type I and Type II diabetes, thyroid disease, viral infection, gingivitis, drug abuse, alcohol abuse, pericarditis, atherosclerosis, vascular disease, hypertrophic cardiomyopathy, dilated cardiomyopathy, myocardial infarction, atrial fibrosis, left ventricular systolic dysfunction, left ventricular diastolic dysfunction, coronary bypass surgery, pacemaker implantation surgery, starvation, an eating disorder, muscular dystrophies, and a genetic defect. Preferably, the heart failure to be treated is diastolic heart failure, heart failure with reduced ejection fraction ($HF_REF$), heart failure with preserved ejection fraction ($HF_PEF$), acute heart failure, and chronic heart failure of ischemic and non-ischemic origin.

In one embodiment, the present invention provides the use of compounds of Formulae (I)-(IX) to treat systolic and/or diastolic dysfunction, wherein the compound is administered in a therapeutically effective amount to increase the ability of the cardiac muscle cells to contract and relax thereby increasing the filling and emptying of both the right and left ventricles, preferably, the left ventricle.

In another embodiment, the present invention provides the use of compounds of Formulae (I)-(IX) to treat heart failure wherein the compound is administered in a therapeutically effective amount to increase ejection fraction in the left ventricle.

In still another embodiment, the present invention provides the use of compounds of Formulae (I)-(IX) to treat heart failure wherein the compound is administered in a therapeutically effective amount to reduce fibrosis in heart tissue.

Another aspect of the invention is a method for treating heart disease wherein the treatment is post myocardial infarction.

Another aspect of the invention is a method for treating dermatological diseases including, but not limited to, rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritis, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema, dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, other disorders of pigmentation, and alopecia (scarring and non-scarring forms). The compounds below would be expected to have therapeutic effects in many different types of skin disease, but have been exemplified by demonstrating accelerated wound healing activity.

Another aspect of the invention is a method for treating heart disease comprising administering a therapeutically effective amount of a compound of Formula (I) to a patient in conjunction with other therapeutic agents.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with at least one of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention may be employed in combination with at least one of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination at least one of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The compounds of the invention may be used in combination with at least one of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with at least one of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries. The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product. The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached. The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemistry Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "wave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | acetic |
| AcOH | acetic acid |
| Acn (or MeCN) | acetonitrile |
| BINAP | 2,2'-bis(diphenylphosphino)-1,1'-binaphthyl |
| BISPIN | ais(pinacolato)diboron |
| Bn | benzyl |
| Boc | tert-butyl carbonyl |

-continued

| | |
|---|---|
| Boc$_2$O | di-tert-butyl dicarbonate |
| Bu | butyl |
| dba as in (Pd$_2$(dba)$_3$) | dibenzylideneacetone |
| DCM | dichloromethane |
| DEAD | diethyl azodicarboxylate |
| DIAD | diisopropyl azodicarboxylate |
| DIEA | diisopropylethylamine |
| DMAP | 4-dimethylaminopyridine |
| DME | dimethoxyethane |
| DMF | dimethylformamide |
| DMSO | dimethyl sulfoxide |
| dppf | 1,1'-bis(diphenylphosphino)ferrocene |
| Et | ethyl |
| EtOH | ethanol |
| EtOAc | ethyl acetate |
| HATU | 2-(7-Aza-1H-benzotriazole-1-yl)-1,1,3,3-tetramethyl-uronium hexafluorophosphate |
| HBTU | 2-(1H-Benzotriazole-1-yl)-1,1,3,3-tetramethyluronium hexafluorophosphate |
| i-Bu | isobutyl |
| i-Pr | isopropyl |
| LAH | lithium aluminum hydride |
| Me | methyl |
| MeOH | methanol |
| NBS | N-bromosuccinimide |
| NMM | N-methylmorpholine |
| NMP | N-Methylpyrrolidone |
| Pet | petroleum |
| Ph | phenyl |
| Pr | propyl |
| rt | room temperature |
| t-Bu | tert-butyl |
| TBDMS-Cl | t-butyldimethylchlorosilane |
| TEA | triethylamine |
| TFA | trifluoroacetic acid |
| THF | tetrahydrofuran |
| Ts | tosyl |
| Xantphos | 4,5-Bis(diphenylphosphino)-9,9-dimethylxanthene |

The disclosed compounds can be made by various methods known in the art including those of the following schemes and in the specific embodiments section. The structure numbering and variable numbering shown in the synthetic schemes are distinct from and should not be confused with the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

A consideration in the planning of any synthetic route in this field is the choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)).

Compounds having the general Formula (I): wherein A, B, C, $R^x$, $R^y$, and $R^z$ are defined above as $Ar^1$, $Ar^2$ and $Ar^3$, $(R^{2a})_{1-4}$, $(R^{3a})_{1-4}$, and $(R^{1a})_{1-2}$, $(R^{1b})_{1-2}$, respectively, can be prepared by the following one or more of the synthetic Schemes.

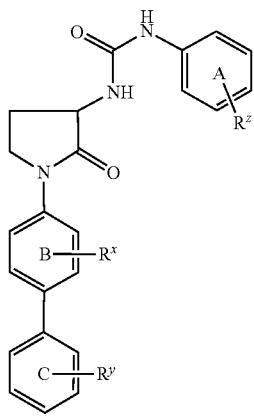

1-Arylpyrrolidinone compounds of this invention wherein rings A, B and C are substituted phenyl rings can be prepared by the general route shown in Scheme 1, starting from a suitably protected 3-aminopyrrolidin-2-one 1a, where PG is a protecting group such as Boc or Cbz. 1a can be prepared with methods known to one skilled in the art. Copper or Pd-catalyzed coupling of 1a to a substituted iodobenzene or bromobenzene 1b or other suitable halo aryl or heteroaryl compound in a suitable solvent such as butanol or dioxane or toluene, in the presence of a base such as potassium carbonate or cesium carbonate and a suitable ligand such as N,N'-dimethylethylenediamine, or xanthphos can afford 1-phenylpyrrolidinones 1c. Additional methods for this transformation include other variations of Ullmann, Goldberg, and Buchwald copper-catalyzed amidation or Buchwald Pd-catalyzed amidation depending on the nature of ring B, using methods known to one skilled in the art for these types of couplings (see for example Yin & Buchwald *Organic Lett.* 2000, 2, 1101; Klapers et al. *JACS,* 2001, 123, 7727; Klapars et al. *JACS,* 2002, 124, 7421; Yin & Buchwald *JACS.* 2002, 124, 6043; Kiyomor, Madoux & Buchwald, *Tet. Lett.,* 1999, 40, 2657). Subsequent palladium-catalyzed coupling of 1c to a suitably substituted phenyl boronic acid 1d, or analogous boronate or trifluoroborate reagent, can provide the biaryl compound 1e. Removal of the Boc or Cbz protecting group from 1e, followed by condensation of the resulting free amine with a suitably substituted phenyl isocyanate, 1g or phenylcarbamate 1h can provide ureas 1f. Suitable isocyanates or 4-nitrophenylcarbamates are either commercially available or can be readily obtained from the corresponding aniline by methods known to one skilled in the art. Alternately, the ureas 1f can be obtained by treatment of the deprotected 3-aminopyrrolidinone intermediate with 4-nitrophenylchloroformate to form the carbamate, followed by condensation with an appropriately substituted aniline 1j. It will also be recognized by one skilled in the art that additional compounds of this invention wherein rings A, B or C are heteroaryl rings, such as pyridine, pyrimidine, thiazole, etc., can also be prepared using the methods outlined in Scheme 1 by substituting the appropriate heteroaryl iodide or bromide for 1b, heteroarylboronic acid or boronate for 1d and heteroaryl amine, isocyanate or p-nitrophenylcarbamate for 1e. Racemic compounds were separated using either chiral HPLC or SFC to provide single enantiomers.

Scheme 1

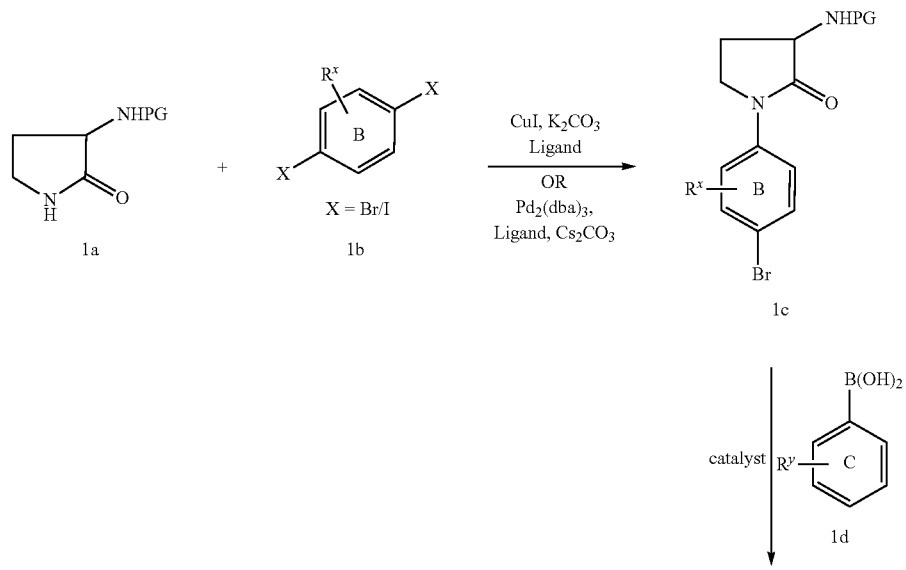

-continued

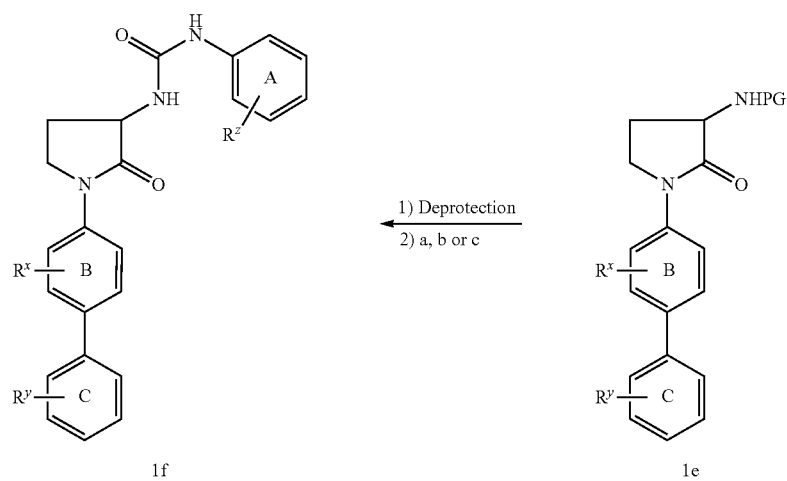

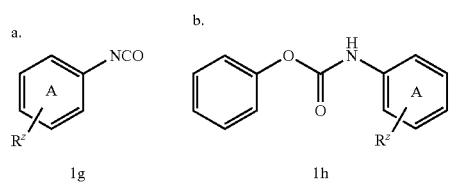

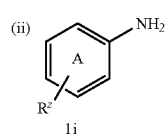

Alternatively as described in Scheme 2, compounds of this invention can be prepared from intermediate 1c by first deprotecting the amine and forming the urea linkage to ring A using the conditions described above for the conversion of 1e to 1f to provide compounds 2a. Compound 2a can then be coupled with an appropriate boronic acid or boronate under Pd-catalysis conditions as shown in Scheme 1 for the transformation of 1c to 1e. Racemic compounds can be separated using either chiral HPLC or SFC to provide single enantiomers.

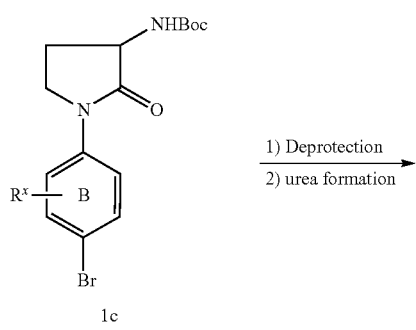

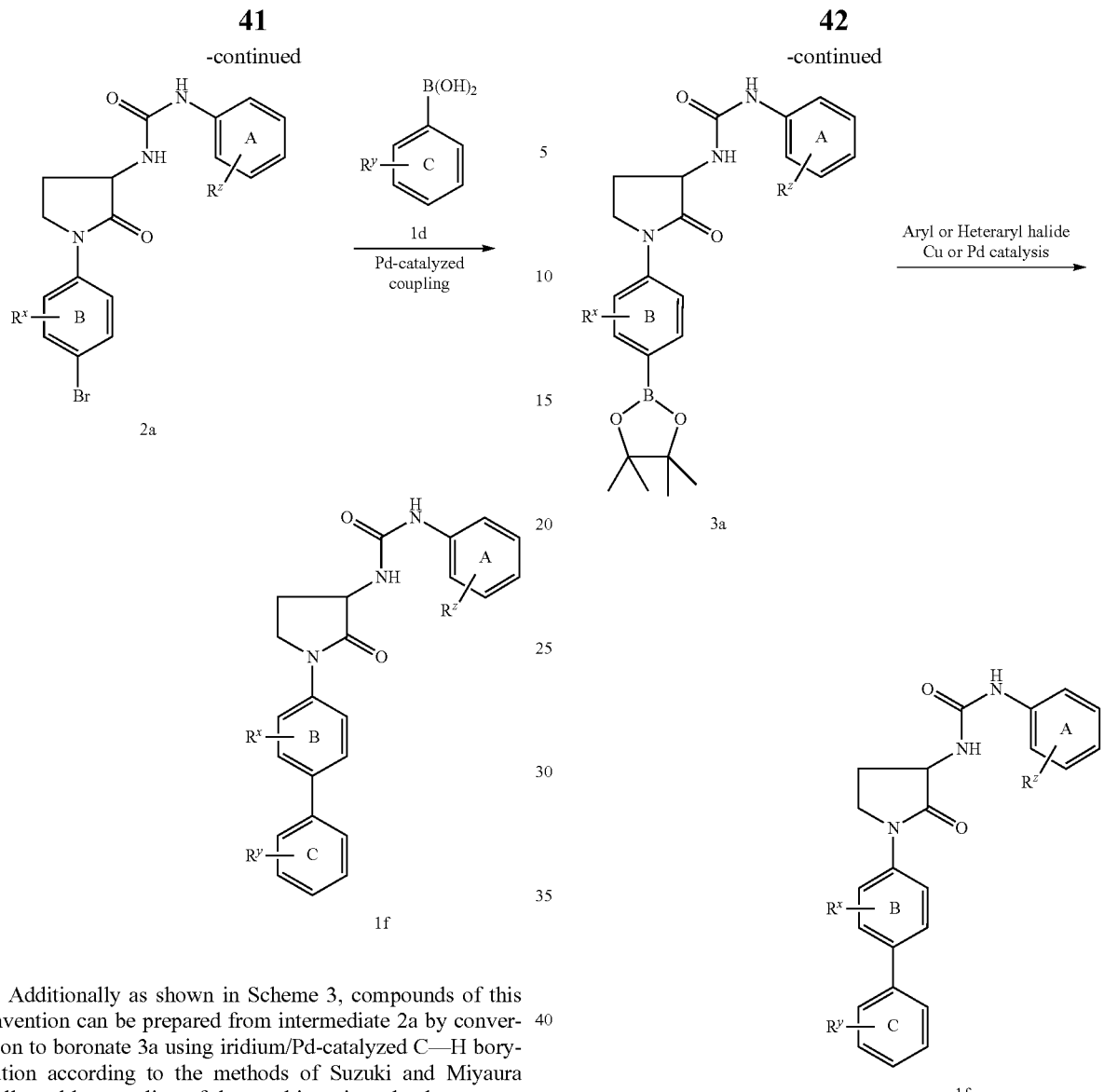

Additionally as shown in Scheme 3, compounds of this invention can be prepared from intermediate 2a by conversion to boronate 3a using iridium/Pd-catalyzed C—H borylation according to the methods of Suzuki and Miyaura followed by coupling of the resulting pinacolatoboron species with aryl or heteroaryl halides using palladium or copper catalyzed processes to provide compounds 1f. Racemic compounds can be separated using either chiral HPLC or SFC to provide single enantiomers.

Scheme 3

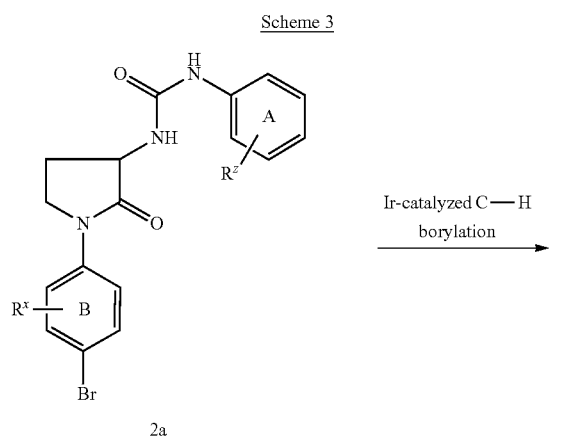

Alternatively as described in Scheme 4, compounds of this invention can be prepared by brominating amine 4a to give intermediate 4b. Subsequent amide coupling with 2,4-dibromo-butyryl chloride under basic conditions such as potassium phosphate in acetonitrile, followed by aqueous ammonia mediated ring closure can give lactam 1c. Intermediate 1c can be converted into final products using the reactions shown in Schemes 1-3. Racemic compounds can be separated using either chiral HPLC or SFC to provide single enantiomers.

Scheme 4

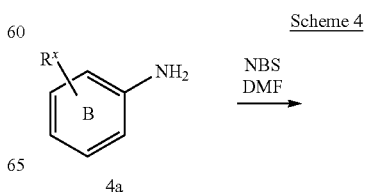

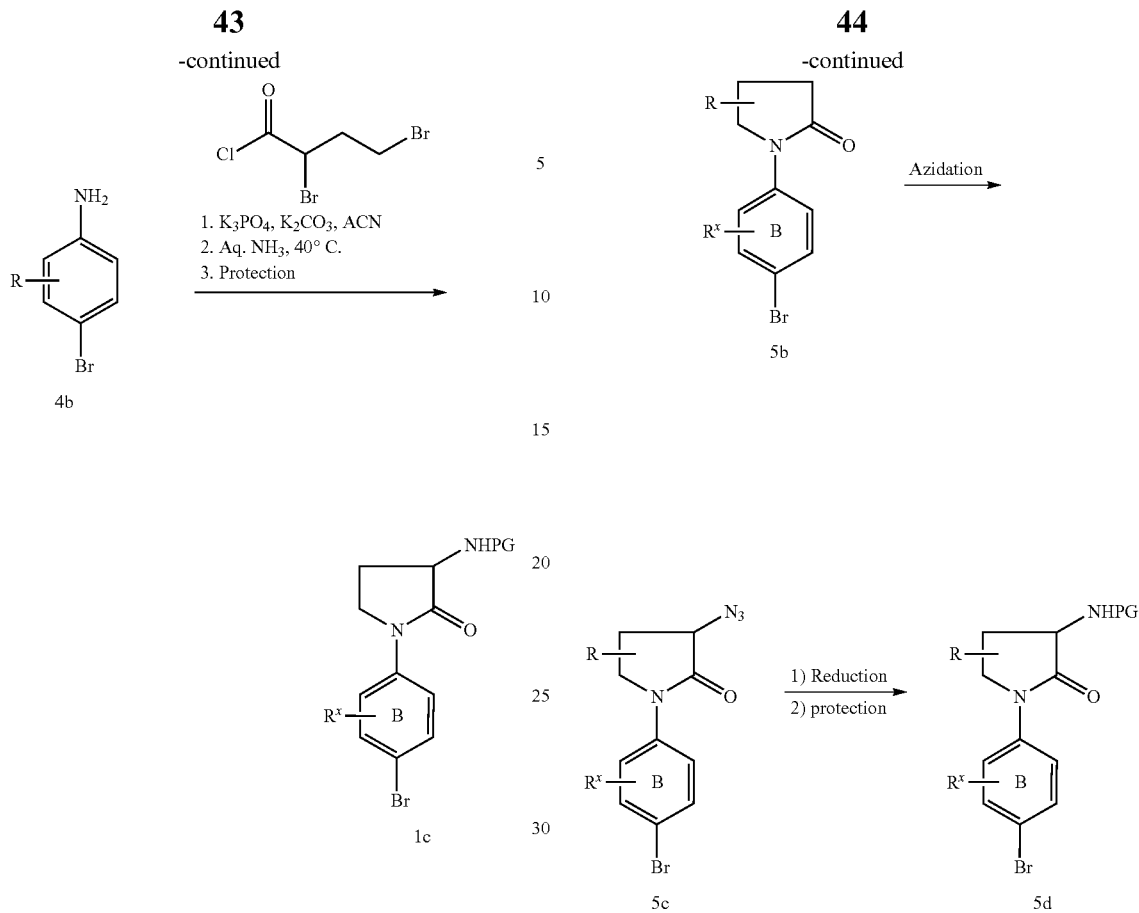

As described in Scheme 5, compounds of this invention with substituted lactams can be prepared from intermediate 5a. Copper or Pd-catalyzed coupling of 5a to a substituted iodobenzene or bromobenzene 1b or other suitable halo aryl or heteroaryl compound in a suitable solvent such as butanol or dioxane or toluene, in the presence of a base such as potassium carbonate or cesium carbonate and a suitable ligand such as N,N'-dimethylethylenediamine, or Xanthphos can afford 1-phenylpyrrolidinones 5b. Additional methods for this transformation include other variations of Ullmann, and Buchwald copper-catalyzed amidation or Buchwald Pd-catalyzed amidation depending on the nature of ring B, using methods known to one skilled in the art for these types of couplings. Subsequent preparation of a lithium lactam enolate and treatment with an azide such as trisyl azide can yield intermediate 5c (see for example *J. Org. Chem.* 2003, 68, 7219-7233). Reduction of azide to amine followed by protection of amine can give intermediate 5d. Chemistry described in previous schemes can used to convert this intermediate into compounds claimed in this patent. Racemic compounds can be separated using either chiral HPLC or SFC to provide single enantiomers.

Compounds of the invention can also be synthesized using the route shown in Scheme 6. Palladium catalyzed borylation of intermediate 1c gives intermediate 6a. Palladium mediated coupling of a suitably substituted aryl halides such as 6b can give biaryl lactam 1e. Chemistry described in previous schemes can used to convert this intermediate into compounds claimed in this patent. Racemic compounds can be separated using either chiral HPLC or SFC to provide single enantiomers.

Scheme 5

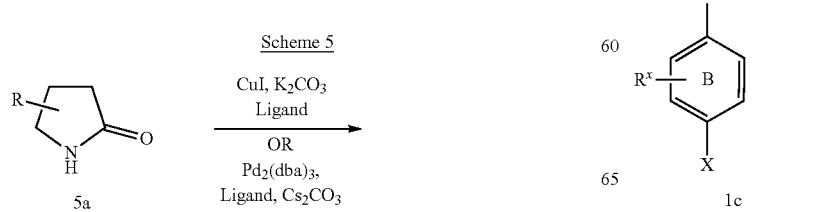

Scheme 6

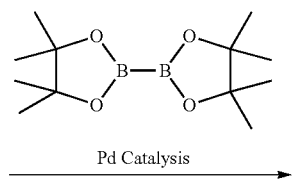

-continued

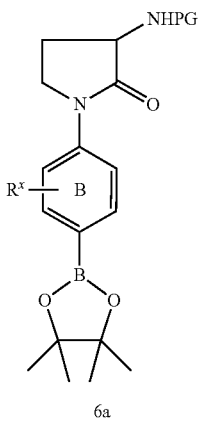

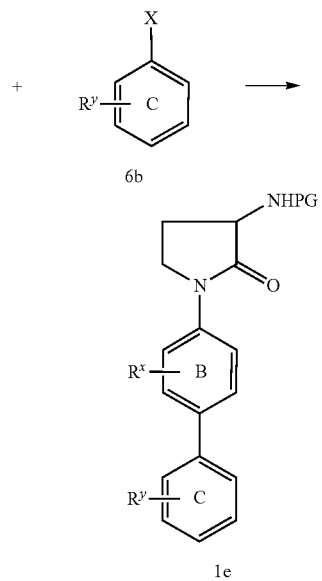

Other features of the invention will become apparent in the course of the following descriptions of exemplary embodiments that are given for illustration of the invention and are not intended to be limiting thereof.

The following methods were used in the exemplified Examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% Acn, 0.1% TFA) and Solvent B (5% water, 95% ACN, 0.1% TFA) or with gradients of Solvent A (95% water, 2% Acn, 0.1% HCOOH) and Solvent B (98% Acn, 2% water, 0.1% HCOOH) or with gradients of Solvent A (95% water, 5% Acn, 10 mM $NH_4OAc$) and Solvent B (98% ACN, 2% water, 10 mM $NH_4OAc$) or with gradients of Solvent A (98% water, 2% Acn, 0.1% $NH_4OH$) and Solvent B (98% Acn, 2% water, 0.1% $NH_4OH$).

LC/MS Methods Employed in Characterization of Examples. Reverse phase analytical HPLC/MS was performed on a Waters Acquity system coupled with a Waters MICROMASS® ZQ Mass Spectrometer.

Method A: Linear gradient of 0 to 100% B over 3 min, with 0.75 min hold time at 100% B;
 UV visualization at 220 nm
 Column: Waters BEH C18 2.1×50 mm
 Flow rate: 1.0 mL/min
 Solvent A: 0.1% TFA, 95% water, 5% Acn
 Solvent B: 0.1% TFA, 5% water, 95% Acn
Method B: Linear gradient of 0 to 100% B over 3 min, with 0.75 min hold time at 100% B;
 UV visualization at 220 nm
 Column: Waters BEH C18 2.1×50 mm
 Flow rate: 1.0 mL/min
 Solvent A: 10 mM ammonium acetate, 95% water, 5% Acn
 Solvent B: 10 mM ammonium acetate, 5% water, 95% Acn Analytical HPLC: Methods Employed in Characterization of Examples Method C: Ascentis Express C18, 2.1×50 mm, 2.7-μm particles; Solvent A: 95% water, 5% Acn, 0.05% TFA; Solvent B: 95% Acn, 5% water, 0.1% TFA; Temperature: 50° C.; Gradient: 0-100% B over 3 minutes, then a 1-minute hold at 100% B; Flow: 1.1 mL/min.

Method D: Ascentis Express C18, 2.1×50 mm, 2.7-μm particles; Solvent A: 95% water, 5% Acn with 10 mM ammonium acetate; Solvent B: 95% Acn, 5% water with 10 mM ammonium acetate; Temperature: 50° C.; Gradient: 0-100% B over 3 minutes, then a 1-minute hold at 100% B; Flow: 1.1 mL/min.

Method E: Column-Kinetex C18, 75×3 mm, 2.6-μm particles; Solvent A: 98% water, 2% Acn with 10 mM ammonium acetate; Solvent B: 98% Acn, 2% water with 10 mM ammonium acetate; Temperature: 25° C.; Gradient: 20-100% B over 4 minutes, then a 0.6-minute hold at 100% B; Flow: 1.0 mL/min; then, Gradient: 100-20% B over 0.4 minutes; Flow: 1.5 mL/min, UV 220 nm.

SFC and Chiral Purity Methods

Method I: Chiralpak AD-H, 250×4.6 mm, 5.0-μm particles; % CO2: 60%, % Co solvent: 40% {0.2% DEA IN IPA:Acn (1:1)}, Total Flow: 4.0 g/min, Back Pressure: 100 bars, Temperature: 25° C., UV: 218 nm.

Method II: Chiralpak OD-H, 250×4.6 mm, 5.0-μm particles; % CO2: 60%, % Co solvent: 40% {0.2% DEA IN IPA:Acn (1:1)}, Total Flow: 4.0 g/min, Back Pressure: 104 bars, Temperature: 24.9° C., UV: 287 nm.

Method III: Chiralpak OJ-H, 250×4.6 mm, 5.0-μm particles; % CO2: 60%, % Co solvent: 30%(0.3% DEA in Methanol), Total Flow: 4.0 g/min, Back Pressure: 101 bars, Temperature: 23.6° C., UV: 272 nm.

Method IV: Chiralpak AS-H, 250×4.6 mm, 5.0-μm particles; % CO2: 60%, % Co solvent: 40%(0.3% DEA in Methanol), Total Flow: 4.0 g/min, Back Pressure: 102 bars, Temperature: 25.4° C., UV: 272 nm.

Method V: Chiralcel OJ-H, 250×4.6 mm, 5.0-μm particles; % CO2: 60%, % Co solvent: 40%(0.2% DEA in Methanol), Total Flow: 4.0 g/min, Back Pressure: 102 bars, Temperature: 24.6° C., UV: 272 nm.

Method VI: Luxcellulose-2, 250×4.6 mm, 5.0-μm particles; % CO2: 60%, % Co solvent: 35%(0.2% DEA in Methanol), Total Flow: 3.0 g/min, Back Pressure: 101 bars, Temperature: 23.6° C., UV: 260 nm.

Method VII: Chiralcel AS-H, 250×4.6 mm, 5.0-μm particles; % CO2: 60%, % Co solvent: 40%(0.2% DEA in Methanol), Total Flow: 4.0 g/min, Back Pressure: 101 bars, Temperature: 24.4° C., UV: 270 nm.

Method VIII: Chiralpak IC, 250×4.6 mm, 5.0-μm particles; % CO2: 60%, % Co solvent: 40%(0.2% DEA in Methanol), Total Flow: 4.0 g/min, Back Pressure: 101 bars, Temperature: 24.4° C., UV: 270 nm.

Method IX: Column: chiralpak IF (250×4.6 mm), 5 micron, mobile phase: 0.2% DEA in ethanol, FLOW: 1.0 ml\min.

Method X: Column: LUX AMYLOSE 2 (250×4.6 mm), 5 micron, mobile phase: 0.2% DEA in n-hexane:ethanol:5:95, FLOW: 1.0 ml\min.

Method XI: Column: CHIRALCEL OD-H (250×4.6 mm), 5 micron, mobile phase: 0.2% DEA in n-hexane:ethanol: 70:30, FLOW: 1.0 ml\min.

Method XII: Column: CHIRAL PAK ID 250×4.6 mm), 5 micron, mobile phase: 0.1% DEA in Methanol, FLOW: 1.0 ml/min.

NMR Employed in Characterization of Examples. $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Intermediate 1: 3-Aminopyrrolidin-2-one

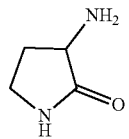

To a stirred solution of hexamethyldisilazane (11 mL, 523 mmol) in $CH_3CN$ (100 mL) at rt was added a solution of DL-2,4-diaminobutyric acid dihydrochloride (10 g, 52 mmol) in Acn (100 mL). The resulting reaction mixture was heated to reflux for 40 h. Then, the crude reaction mixture was poured into ice cold MeOH (400 mL), stirred at rt for 30 min and evaporated under reduced pressure. The resulting solid was dissolved in $CH_2Cl_2$ (700 mL), and the insoluble residue was removed by filtration under vacuum. Then, the filtrate was concentrated under reduced pressure to give 3-aminopyrrolidin-2-one (4.1 g, 41 mmol, 78% yield) as a yellow solid. $^1$H NMR (400 MHz, DMSO-$d_6$): δ 7.59 (br. s., 2H), 3.23-3.10 (m, 1H), 3.09-3.03 (m, 2H), 2.23-2.22 (m, 1H), 1.70-1.57 (m, 1H).

Intermediate 2: tert-Butyl (2-oxopyrrolidin-3-yl)carbamate

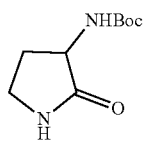 [SMILES: CC(C)(C)OC(=O)NC1CCNC1=O]

To a stirred solution of 3-aminopyrrolidin-2-one (4.0 g, 40 mmol) in methanol-triethylamine (130 mL, 9:1) under argon atmosphere at rt, was added Boc-anhydride (9.6 mL, 41 mmol). The reaction mixture was stirred at rt overnight followed by heating to reflux for two hours. Then, the reaction mixture was cooled to rt and concentrated under reduced pressure. Ether (50 mL) was added to the crude residue and the solid was filtered through Buchner funnel to yield Intermediate 2 (4.0 g, 20 mmol, 50% yield) as brown solid. $^1$H NMR (400 MHz, DMSO-$d_6$): δ 7.69 (br. s., 1H), 6.99 (d, J=8.0 Hz, 1H), 4.06-3.96 (m, 1H), 3.19-3.10 (m, 2H), 2.29-2.19 (m, 1H), 1.89-1.76 (m, 1H), 1.35 (s, 9H).

Intermediate 3: tert-Butyl (1-(4-bromo-2,3-difluorophenyl)-2-oxopyrrolidin-3-yl)carbamate

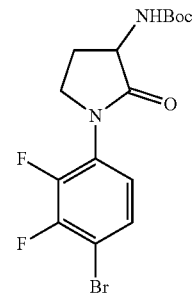 [SMILES: CC(C)(C)OC(=O)NC1CCN(c2ccc(Br)c(F)c2F)C1=O]

To a stirred solution of Intermediate 2 (1.0 g, 5.0 mmol) in 1,4-dioxane (10 mL), were added 1,4-dibromo-2,3-difluorobenzene (1.6 g, 6.0 mmol), and $Cs_2CO_3$ (3.3 g, 10 mmol). The reaction mixture was purged with nitrogen for 5 min and charged with Xantphos (0.29 g, 0.50 mmol) and $Pd_2(dba)_3$ (0.23 g, 0.25 mmol). The reaction mixture was again purged with nitrogen for 3 min and heated at 120° C. for 16 h. The reaction mixture was cooled, filtered through a Celite pad, and the filtrate was concentrated under reduced pressure. The crude product was purified using column chromatography (pet. ether-EtOAc) to yield Intermediate 3 (1.1 g, 2.8 mmol, 47% yield) as brown solid. MS(ESI) m/z: 391.2 (M+H)$^+$. $^1$H NMR (400 MHz, DMSO-$d_6$) δ 7.61-7.59 (m, 1H), 7.35-7.28 (m, 2H), 4.39-4.28 (m, 1H), 3.82-3.64 (m, 2H), 2.42-2.31 (m, 1H), 2.10-1.97 (m, 1H), 1.40 (s, 9H).

Intermediate 4: tert-Butyl (1-(2,3-difluoro-2'-(methylsulfonamido)-[1,1'-biphenyl]-4-yl)-2-oxopyrrolidin-3-yl)carbamate

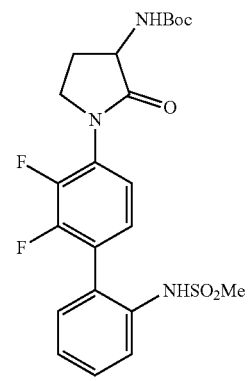

To a solution of Intermediate 3 (1.1 g, 2.1 mmol) in 1,4-dioxane-water (11 mL, 10:1) at rt, were added (2-(methylsulfonamido)phenyl)boronic acid (0.45 g, 2.1 mmol), and potassium phosphate, tribasic (0.74 g, 4.2 mmol). The reaction mixture was purged with nitrogen for 5 min and charged with PdCl₂(dppf)-CH₂Cl₂ (0.17 g, 0.21 mmol). The reaction mixture was again purged with nitrogen for 3 min and heated at 80° C. for 16 h. The reaction mixture was cooled and filtered through a Celite pad, and the filtrate was concentrated under reduced pressure. The crude product was purified via column chromatography (pet. ether-EtOAc) to give Intermediate 4 (0.44 g, 0.91 mmol, 43% yield) as brown solid. MS(ESI) m/z: 482.2 [M+H]⁺; ¹H NMR (400 MHz, DMSO-d₆) δ 9.13 (s, 1H), 7.53-7.44 (m, 2H), 7.38-7.29 (m, 4H), 7.24-7.17 (m, 1H), 4.36-4.31 (m, 1H), 3.86-3.69 (m, 2H), 2.90 (s, 3H), 2.41-2.37 (m, 1H), 2.10-2.02 (m, 1H), 1.41 (s, 9H).

Intermediate 5: N-(4'-(3-Amino-2-oxopyrrolidin-1-yl)-2',3'-difluoro-[1,1'-biphenyl]-2-yl)methanesulfonamide hydrochloride

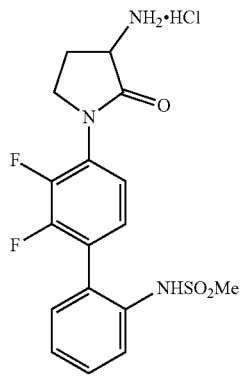

To an ice cooled solution of Intermediate 4 (440 mg, 0.91 mmol) in 1,4-dioxane (1 mL), was added 4 N HCl in 1,4-dioxane (4.6 mL, 1 mmol), and the reaction mixture was stirred at rt for 2 h. The solvent was evaporated under reduced pressure. The gummy solid was triturated with diethyl ether (20 mL×2) and dried to yield Intermediate 5 (350 mg, 0.84 mmol, 92% yield) as a brown solid.

MS(ESI) m/z: 418.2 [M+H]⁺; ¹H NMR (400 MHz, DMSO-d₆) δ 9.18 (s, 1H), 8.71 (br. s., 3H), 7.55-7.47 (m, 2H), 7.45-7.24 (m, 4H), 4.33-4.25 (m, 1H), 3.97-3.85 (m, 2H), 2.89 (s, 3H), 2.64-2.54 (m, 1H), 2.30-2.17 (m, 1H).

Intermediate 6: tert-butyl (R)-(2-oxopyrrolidin-3-yl)carbamate

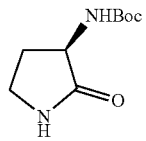 [SMILES: CC(C)(C)OC(=O)N[C@@H]1CCNC1=O]

1-Propanephosphonic anhydride (50% in EtOAc, 210 mL, 340 mmol) was added to a solution of Boc-D-2,4-diaminobutyric acid (50 g, 230 mmol) and TEA (96 mL, 690 mmol) in DCM (1500 mL) at 0° C. The reaction mixture was stirred at rt overnight under nitrogen. The reaction mixture was concentrated in vacuo, and the crude product was purified by column chromatography (MeOH/DCM). The product was recrystallized with EtOAc/pet. ether to obtain Intermediate 6 (32 g, 70 mmol, 70% yield) as a white solid. MS(ESI) m/z: 201.2 (M+H)⁺. ¹H NMR (400 MHz, DMSO-d₆) δ=7.69 (s, 1H), 6.99 (br. d., J=9.0 Hz, 1H), 4.01 (q, J=9.0 Hz, 1H), 3.17-3.09 (m, 2H), 2.28-2.19 (m, 1H), 1.90-1.75 (m, 1H), 1.39 (s, 9H).

Intermediate 7: tert-butyl (R)-(1-(2,3-difluoro-4-bromophenyl)-2-oxopyrrolidin-3-yl)carbamate

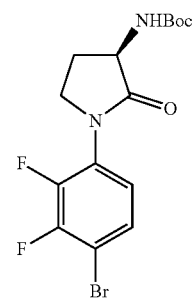 [SMILES: CC(C)(C)OC(=O)N[C@@H]1CCN(c2ccc(Br)c(F)c2F)C1=O]

A reaction mixture of Intermediate 6 (20 g, 100 mmol), 2,3-difluoro-1,4-dibromobenzene (14 g, 110 mmol), potassium phosphate tribasic (32 g, 150 mmol), and cuprous iodide (7.6 g, 40 mmol) in 1,4-dioxane (250 mL) was purged with nitrogen for 5 min. N,N'-Dimethylethylenediamine (5.5 mL, 50 mmol) was added, and the reaction mixture was heated in a pressure tube at 65° C. for 12 h. The reaction mixture was diluted with EtOAc, filtered through Celite, and concentrated under reduced pressure. The crude product was purified by column chromatography (35% EtOAc in pet ether) and recrystallized (EtOAc/pet ether) to obtain Intermediate 7 (18 g, 39 mmol, 39% yield) as a white solid. MS(ESI) m/z: 439.0 (M+H)⁺. ¹H NMR (400 MHz, CDCl₃) δ=7.54 (ddd, J=8.5, 6.3, 2.3 Hz, 1H), 7.09 (ddd, J=8.5, 6.3, 2.3 Hz, 1H), 5.16 (br. s., 1H), 4.41-4.30 (m, 1H), 3.87 (m, 1H), 3.79-3.69 (m, 1H), 2.85-2.73 (m, 1H), 2.17-2.05 (m, 1H), 1.48 (m, 9H).

Intermediate 8: (2-bromophenyl)dimethylphosphine oxide

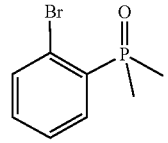

In a pressure tube, a reaction mixture of 1-bromo-2-iodobenzene (2.3 mL, 18 mmol), potassium phosphate tribasic (5.6 g, 27 mmol) and Xantphos (0.61 g, 1.1 mmol) in DMF (40 mL) was degassed with argon for 3 min. Dimethylphosphine oxide (1.7 g, 21 mmol), and PdOAc₂ (0.20 g, 0.88 mmol) were added. The mixture was degassed with argon, sealed and heated for 16 h at 110° C. The reaction mixture was cooled to rt, filtered through Celite and concentrated under reduced pressure. The crude product was purified by column chromatography (CHCl₃/MeOH) to give Intermediate 8 (2.1 g, 9.0 mmol, 51% yield). MS(ESI) m/z: 233.0 (M+H)⁺. ¹H NMR (300 MHz, DMSO-d₆) δ=7.97 (ddd, J=11.9, 7.8, 2.0 Hz, 1H), 7.76 (ddd, J=7.8, 3.9, 1.2 Hz, 1H), 7.65-7.44 (m, 2H), 1.83 (d, J=13.5 Hz, 6H).

Intermediate 9: tert-butyl (R)-(1-(2'-(dimethylphosphoryl)-2,3-difluoro-[1,1'-biphenyl]-4-yl)-2-oxopyrrolidin-3-yl)carbamate

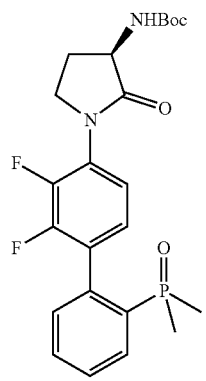

A reaction mixture of Intermediate 7 (15 g, 38 mmol), Intermediate 8 (11 g, 46 mmol), bispin (24 g, 96 mmol), and K$_3$PO$_4$ (24 g, 115 mmol) in 1,4-dioxane (250 mL) was purged with argon for 5 min. PdCl$_2$(dppf)-CH$_2$Cl$_2$ adduct (3.1 g, 3.8 mmol) was added and the mixture was again purged with argon and then stirred in a pressure tube at 105° C. for 24 h. The reaction mixture was diluted with EtOAc, filtered through Celite, and concentrated under reduced pressure. The crude product was purified via column chromatography (5% MeOH in CHCl$_3$) to give Intermediate 9 (9.0 g, 19 mmol, 51% yield). MS(ESI) m/z: 465.4 (M+H)$^+$. $^1$H NMR (400 MHz, DMSO-d$_6$) δ=7.92 (ddd, J=12.8, 7.6, 1.3 Hz, 1H), 7.70-7.49 (m, 2H), 7.41-7.23 (m, 4H), 4.54-4.23 (m, 1H), 3.87-3.70 (m, 2H), 2.44-2.37 (m, 1H), 2.21-2.00 (m, 1H), 1.51 (br. d., J=13.1 Hz, 6H), 1.42 (s, 9H).

Intermediate 10: (R)-3-amino-1-(2'-(dimethylphosphoryl)-2,3-difluoro-[1,1'-biphenyl]-4-yl)pyrrolidin-2-one hydrochloride

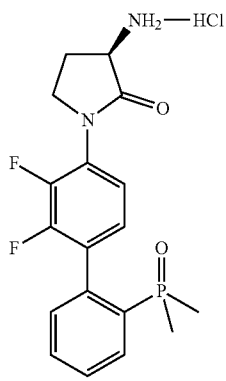 [SMILES: CP(C)(=O)c1ccccc1-c1ccc(N2CC[C@@H](NCl)C2=O)c(F)c1F]

HCl (4 M in 1,4-dioxane, 200 mL, 800 mmol) was added to a stirred solution of Intermediate 9 (34 g, 73 mmol) in 1,4-dioxane (500 mL) at rt. The reaction mixture was stirred for 3 h and concentrated under reduced pressure to yield Intermediate 10 (28 g, 70 mmol, 95% yield), which was used in the next synthetic step without further purification. MS(ESI) m/z: 365.2 (M+H)$^+$. $^1$H NMR (400 MHz, DMSO-d6) δ=8.62 (br. s., 3H), 7.95-7.81 (m, 1H), 7.68-7.57 (m, 2H), 7.39-7.32 (m, 2H), 7.31-7.24 (m, 1H), 4.33-4.19 (m, 1H), 3.94-3.84 (m, 2H), 2.61-2.53 (m, 1H), 2.25-2.15 (m, 1H), 1.53 (d, J=13.1 Hz, 6H).

Intermediate 11: phenyl (4-chloro-2-fluorophenyl)carbamate

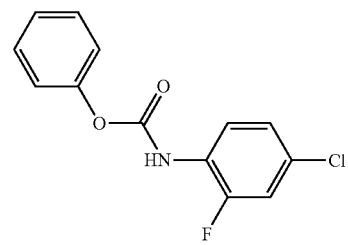 [SMILES: O=C(Nc1ccc(Cl)cc1F)Oc1ccccc1]

Phenyl chloroformate (20 mL, 160 mmol) was added slowly to a solution of 4-chloro-2-fluoroaniline (19 mL, 170 mmol) and pyridine (35 mL, 430 mmol) in DCM (250 mL) at 0° C. The reaction mixture was gradually warmed to rt and stirred for 12 h. The reaction mixture was quenched with water. The mixture was extracted with DCM (3×200 mL). The combined organic layers were washed with 0.5 N HCl and 10% sodium bicarbonate, dried over sodium sulfate, and concentrated in vacuo. The solid was stirred in pet ether (100 mL) for 15 min, filtered and dried to get Intermediate 11 (36 g, 40 mmol, 78% yield). $^1$H NMR (300 MHz, CHLOROFORM-d) δ=10.22-9.99 (m, 1H), 7.73 (br. t., J=8.7 Hz, 1H), 7.52 (dd, J=10.7, 2.1 Hz, 1H), 7.47-7.38 (m, 2H), 7.34-7.18 (m, 4H).

Intermediate 12: phenyl (2-fluoro-4-(trifluoromethyl)phenyl)carbamate

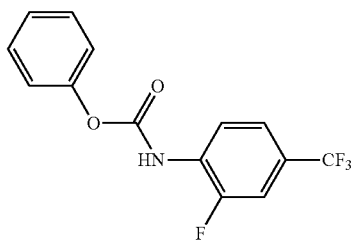 [SMILES: O=C(Nc1ccc(C(F)(F)F)cc1F)Oc1ccccc1]

Phenyl chloroformate (4.5 mL, 36 mmol) was added slowly to a solution of 2-fluoro-4-(trifluoromethyl) aniline (8.0 g, 45 mmol) and pyridine (9.0 mL, 110 mmol) in DCM (80 mL) at 0° C. The reaction mixture was gradually warmed to rt and stirred for 3 h. The reaction mixture was quenched with water and the mixture was extracted with DCM (3×200 mL). The combined organic layers were washed with 0.5 N HCl and 10% sodium bicarbonate, dried over sodium sulfate, and concentrated in vacuo. The solid was stirred in pet. ether (100 mL) for 15 min, filtered and dried to give Intermediate 11 (9.0 g, 30 mmol, 67% yield). MS(ESI) m/z: 317.2 (M+NH$_4$)$^+$. $^1$H NMR (300 MHz, CHLOROFORM-d) δ=10.43 (s, 1H), 8.04 (br. t., J=8.1 Hz, 1H), 7.75 (br. d., J=10.9 Hz, 1H), 7.60 (br. d., J=8.6 Hz, 1H), 7.52-7.38 (m, 2H), 7.36-7.21 (m, 3H).

Intermediate 13: (R)-1-(1-(4-bromo-2,3-difluorophenyl)-2-oxopyrrolidin-3-yl)-3-(2-fluoro-4-(trifluoromethyl)phenyl) urea

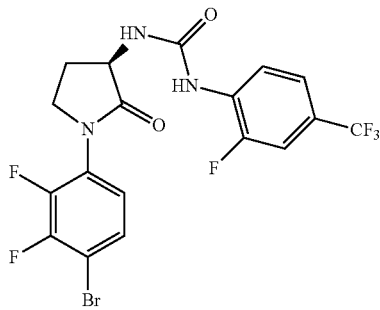 [SMILES: O=C(Nc1ccc(C(F)(F)F)cc1F)N[C@@H]1CCN(c2ccc(Br)c(F)c2F)C1=O]

HCl (4 M in dioxane, 32 mL, 130 mmol) was added dropwise to a solution of Intermediate 7 (10 g, 26 mmol) in DCE (300 mL) at 0° C. The reaction mixture was stirred for 2 h at rt and concentrated under reduced pressure. The crude intermediate was dissolved in 1,4-dioxane (300 mL) and cooled to 0° C. DIEA (22 mL, 130 mmol) was added dropwise over a period of 10 min, Intermediate 12 (6.9 g, 23 mmol) was added, and the mixture was stirred for 12 h at rt. The reaction mixture was filtered through Celite, and the filter plug was washed with EtOAc. The filtrate was dried over sodium sulfate and concentrated under reduced pressure. The crude product was purified by column chromatography (2% MeOH:DCM) to yield Intermediate 13(12 g, 24 mmol, 95% yield). MS(ESI) m/z: 496.0 (M+H)$^+$.

Intermediate 14: (R)-1-(1-(2,3-difluoro-4-(4,4,5,5-tetramethyl-1,3,2-dioxaborolan-2-yl)phenyl)-2-oxopyrrolidin-3-yl)-3-(2-fluoro-4-(trifluoromethyl)phenyl)urea

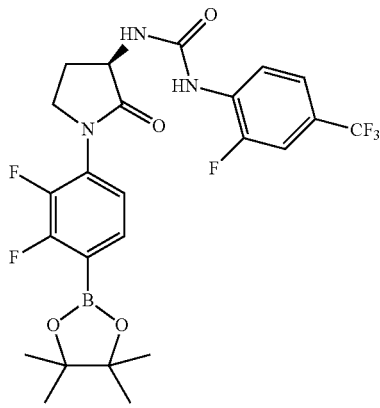 [SMILES: CC1(C)OB(c2ccc(N3CC[C@@H](NC(=O)Nc4ccc(C(F)(F)F)cc4F)C3=O)c(F)c2F)OC1(C)C]

A solution of Intermediate 13 (12 g, 24 mmol) and bispin (18 g, 73 mmol) in 1,4-dioxane (120 mL) was degassed with argon for 5 min. PdCl$_2$(dppf)-CH$_2$Cl$_2$ (4.0 g, 4.8 mmol) was added, and the reaction mixture was slowly heated to 110° C. and stirred for 16 h. The mixture was filtered through Celite, and the plug was washed with EtOAc. The filtrate was dried over sodium sulfate and concentrated under reduced pressure to give Intermediate 14 (13 g, 24 mmol, 99% yield). MS(ESI) m/z: 544.2 (M+H)$^+$.

Intermediate 15: (3-bromopyridin-2-yl)dimethylphosphine oxide

To a stirred solution of 3-bromo-2-iodopyridine (5.0 g, 18 mmol) in DMF (5 mL), were added dimethylphosphine oxide (1.7 g, 21 mmol), and K$_3$PO$_4$ (4.1 g, 19 mmol). The reaction mixture was purged with nitrogen for 5 min and charged with Xantphos (1.0 g, 1.8 mmol) and Pd(OAc)$_2$ (0.20 g, 0.88 mmol). The reaction mixture was again purged with nitrogen for 3 min and heated at 100° C. for 9 hours. The reaction mixture was filtered through Celite and concentrated under reduced pressure. The crude material was purified by column chromatography (5% MeOH—CHCl$_3$) to give Intermediate 15 (2.7 g, 12 mmol, 66% yield) as a brown liquid. MS(ESI) m/z: 234.1 [M+H]$^+$. $^1$H NMR (400 MHz, DMSO-d$_6$) δ=8.72 (d, J=4.8 Hz, 1H), 8.23-8.20 (m, 1H), 7.53-7.49 (m, 1H), 1.66 (d, J=13.6 Hz, 6H).

Intermediate 16: (2-Bromo-6-fluorophenyl)dimethylphosphine oxide

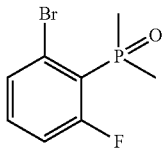

To a stirred solution of 1-bromo-3-fluoro-2-iodobenzene (2.0 g, 6.7 mmol) in 1,4-dioxane (15 mL), were added dimethylphosphine oxide (0.62 g, 8.0 mmol), and K$_3$PO$_4$ (1.6 g, 7.3 mmol). The reaction mixture was purged with nitrogen for 5 min and charged with Xantphos (0.39 g, 0.67 mmol) and Pd$_2$(dba)$_3$ (0.30 g, 0.33 mmol). The reaction mixture was again purged with nitrogen for 3 min and heated at 100° C. for 9 h. The reaction mixture was filtered through Celite and concentrated under reduced pressure. The crude material was purified by column chromatography (0-100% EtOAc-Hexane, followed by 3% MeOH—CHCl$_3$) to give Intermediate 16 (0.33 g, 1.3 mmol, 20% yield) as a yellow solid. MS(ESI) m/z: 250.9 [M+H]$^+$. $^1$H NMR (400 MHz, DMSO-d$_6$) δ=7.63 (d, J=8.0 Hz, 1H), 7.52 (td, J=8.0, 6.0 Hz, 1H), 7.43-7.28 (m, 1H), 1.87 (d, J=16.6 Hz, 3H), 1.86 (d, J=16.6 Hz, 3H).

Intermediate 17: diethylphosphine oxide

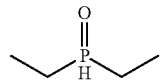

To a stirred solution of 2M ethylmagnesium bromide (330 mL, 650 mmol) in THF at rt, was added diethyl phosphonate (30 g, 220 mmol) and the mixture was stirred for additional 2 hours. Then, a cold solution of K₂CO₃ (90 g, 650 mmol) in water (120 mL) was added and the reaction mixture was filtered through a Celite pad. The filtrate was concentrated under reduced pressure and azeotroped with toluene (20 mL×3). The crude material was diluted with DCM (100 mL), filtered through a cotton bed and concentrated under reduced pressure to give Intermediate 17 (12 g, 110 mmol, 52% yield) as a yellowish liquid. MS(ESI) m/z: 107.2 [M+H]⁺.

Intermediate 18: (2-Bromophenyl)diethylphosphine oxide

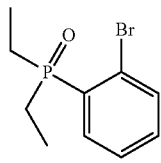

To a stirred solution of 1-bromo-2-iodobenzene (10 g, 35.3 mmol) in DMF (50 mL), were added diethylphosphine oxide (4.5 g, 42 mmol), and K₃PO₄ (15 g, 71 mmol). The reaction mixture was purged with nitrogen for 5 min and charged with Xantphos (1.0 g, 1.8 mmol) and palladium (II) acetate (0.40 g, 1.8 mmol). The reaction mixture was again purged with nitrogen for 3 min, heated to 100° C. and stirred for 16 h. The reaction mixture was cooled, filtered through a Celite pad, and the filtrate was concentrated under reduced pressure. The crude product was purified by column chromatography (MeOH-EtOAc) to yield the Intermediate 18 (3.2 g, 12 mmol, 35% yield) as a yellowish liquid. MS(ESI) m/z: 263.2 [M+H]⁺. ¹H NMR (400 MHz, DMSO-d₆) δ=8.05-7.94 (m, 1H), 7.79-7.68 (m, 2H), 7.64-7.48 (m, 1H), 2.26-2.03 (m, 4H), 0.93 (td, J=17.4, 7.7 Hz, 6H).

Intermediate 19: Dimethyl (2-bromophenyl)phosphonate

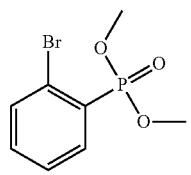

To a stirred solution of 2-bromophenyl trifluoromethanesulfonate (2.0 g, 6.6 mmol) in toluene (100 mL), were added dimethyl phosphonate (1.1 g, 9.8 mmol), and DIEA (1.7 mL, 9.8 mmol). The reaction mixture was purged with nitrogen for 5 min and charged with 1,3-bis(diphenylphosphino)propane (0.14 g, 0.33 mmol) and palladium (II) acetate (0.04 g, 0.17 mmol). The reaction mixture was again purged with nitrogen for 3 min and heated at 110° C. for 16 h. The reaction mixture was cooled and filtered through a Celite pad, and the filtrate was concentrated under reduced pressure. The product was purified by flash chromatography (5-10% MeOH in chloroform) to yield Intermediate 19 (1.2 g, 3.6 mmol, 55% yield) as a colorless liquid. MS(ESI) m/z: 267.1 [M+H]⁺. ¹H NMR (400 MHz, CDCl₃) δ=8.02-8.00 (m, 1H) 7.70-7.69 (m, 1H) 7.43-7.41 (m, 2H) 3.83-3.73 (m, 6H).

Intermediate 20: Ethyl (2-bromophenyl)(methyl)phosphinate

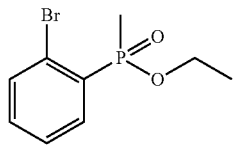

To a stirred solution of 1-bromo-2-iodobenzene (1.0 g, 3.5 mmol) in DMF (5 mL), were added diethyl methylphosphonite (0.58 g, 4.2 mmol), and K₃PO₄ (2.3 g, 11 mmol). The reaction mixture was purged with nitrogen for 5 min and charged with Xantphos (0.21 g, 0.35 mmol) and palladium (II) acetate (0.040 g, 0.18 mmol). The reaction mixture was again purged with nitrogen for 3 min and heated at 110° C. for 16 h. The reaction mixture was cooled, filtered through Celite pad and the filtrate was concentrated under reduced pressure. The crude product was purified by flash chromatography (pet. ether-EtOAc) to yield the Intermediate 20 (0.35 g, 1.3 mmol, 38% yield) as a brown liquid. MS(ESI) m/z: 263.1 [M+H]⁺. ¹H NMR (400 MHz, CDCl₃) δ=8.18-8.13 (m, 1H) 7.67-7.65 (m, 1H) 7.64-7.38 (m, 2H) 4.07-4.03 (m, 1H) 3.85-3.80 (m, 1H) 1.86 (d, J=15.0 Hz, 3H), 1.32 (t, J=7.2 Hz, 3H).

Intermediate 21: 4-Bromo-3-cyclopropyl-2-fluoroaniline

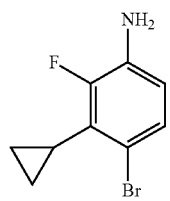 [SMILES: Nc1ccc(Br)c(C2CC2)c1F]

To an ice cooled solution of 3-cyclopropyl-2-fluoroaniline (0.85 g, 5.6 mmol) in DMF (11 mL) under argon atmosphere at rt, was added NBS (1.0 g, 5.6 mmol). The reaction mixture was gradually warmed to rt over 3 h and quenched with aqueous Na₂S₂O₃ (10 mL). The biphasic mixture was extracted with EtOAc (30 mL×2). The combined organic layer was washed with brine (15 mL×2), dried over Na₂SO₄, concentrated under reduced pressure and purified through flash column chromatography (25% EtOAc-Pet.ether) to yield Intermediate 21 (1.2 g, 5.0 mmol, 89% yield) as an orange liquid. ¹H NMR (400 MHz, CDCl₃) δ=7.11 (d, J=8.5 Hz, 1H), 6.51 (t, J=8.8 Hz, 1H), 3.67 (br s, 2H), 1.80 (tt, J=8.6, 5.7 Hz, 1H), 1.07-0.82 (m, 4H).

Intermediate 22: tert-Butyl (1-(4-bromo-3-cyclopropyl-2-fluorophenyl)-2-oxopyrrolidin-3-yl)carbamate

Intermediate 23: tert-Butyl(1-(2-cyclopropyl-2'-(dimethylphosphoryl)-3-fluoro-[1,1'-biphenyl]-4-yl)-2-oxopyrrolidin-3-yl)carbamate

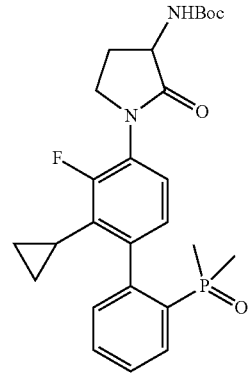 [SMILES: CC(C)(C)OC(=O)NC1CCN(c2ccc(-c3ccccc3P(C)(C)=O)c(C3CC3)c2F)C1=O]

To a solution of Intermediate 22 (0.50 g, 1.2 mmol) in 1,4-dioxane (10 mL) at rt, were added (2-bromophenyl)dimethylphosphine oxide (0.42 g, 1.8 mmol), 4,4,4',4',5,5,5',5'-octamethyl-2,2'-bi(1,3,2-dioxaborolane) (0.92 g, 3.6 mmol), and $K_2CO_3$ (0.42 g, 3.0 mmol). The reaction mixture was purged with nitrogen for 5 min and then charged with $PdCl_2(dppf) \cdot DCM$ (0.090 g, 0.12 mmol). The reaction mixture was again purged with nitrogen for 3 min and heated at 100° C. for 16 h. The reaction mixture was cooled and filtered through a Celite pad, and the filtrate was concentrated under reduced pressure. The crude intermediate was purified by flash chromatography (MeOH—$CHCl_3$) to yield Intermediate 23 (0.30 g, 0.62 mmol, 51% yield) as an orange solid. MS(ESI) m/z: 487.1 [M+H]$^+$. $^1$H NMR (400 MHz, $CDCl_3$) δ=8.25-8.10 (m, 1H), 7.62-7.48 (m, 2H), 7.33-7.21 (m, 2H), 7.07-6.95 (m, 1H), 5.26-5.10 (m, 1H), 4.48-4.27 (m, 1H), 3.93-3.79 (m, 1H), 3.79-3.67 (m, 1H), 2.88-2.74 (m, 1H), 2.20-2.01 (m, 1H), 1.54-1.37 (m, 16H), 1.04-0.85 (m, 2H), 0.73-0.68 (m, 2H).

Intermediate 24: 3-Amino-1-(2-cyclopropyl-2'-(dimethylphosphoryl)-3-fluoro-[1,1'-biphenyl]-4-yl)pyrrolidin-2-one hydrochloride

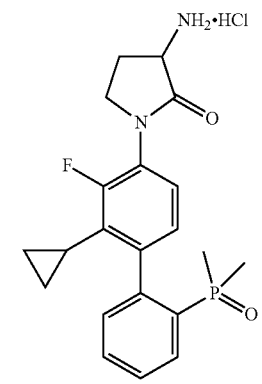

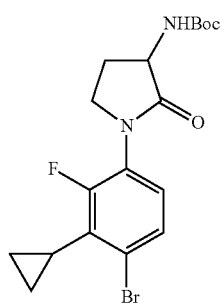

To a stirred solution of Intermediate 21 (1.1 g, 4.8 mmol) in Acn (10 mL) at 0° C. under nitrogen was added $K_3PO_4$ (1.0 g, 4.8 mmol). The resulting mixture was treated with 2,4-dibromobutanoyl chloride (0.60 mL, 4.5 mmol) and stirred for 2 h. Then, $K_2CO_3$ (2.0 g, 14 mmol) was added, and the mixture was stirred for 16 h. The solid was filtered through a Celite pad and the pad was washed with Acn (15 mL×2). The filtrate was partially evaporated, ammonia (aq, 10 mL, 460 mmol) was added, and the mixture was stirred at 40° C. for 16 h. The mixture was extracted with EtOAc (20 mL×3) and washed with brine (20 mL). The combined organics were dried over $Na_2SO_4$ and evaporated to give crude 3-amino-1-(4-bromo-3-cyclopropyl-2-fluorophenyl)pyrrolidin-2-one (1.0 g, 3.2 mmol, 67% yield), which was used in next step without further purification.

To a stirred solution of 3-amino-1-(4-bromo-3-cyclopropyl-2-fluorophenyl)pyrrolidin-2-one in DCM (15 mL) under argon atmosphere at rt, were added TEA (0.98 mL, 7.0 mmol) and $(Boc)_2O$ (0.90 mL, 3.9 mmol). The reaction mixture was stirred at rt for 6 hours. Then, the reaction mixture was quenched with aqueous saturated $NH_4Cl$ (20 mL) and extracted with EtOAc (20 mL×3). The combined organic layers were washed with brine (20 mL), dried over $Na_2SO_4$, concentrated under reduced pressure and purified via flash chromatography (20% EtOAc-pet. ether) to give Intermediate 22 (1.0 g, 2.4 mmol, 69% yield) as a yellowish gummy solid. MS(ESI) m/z: 413.1 [M+H]$^+$. $^1$H NMR (400 MHz, $CDCl_3$) δ=7.38 (dd, J=8.5, 1.5 Hz, 1H), 7.14-7.09 (m, 1H), 5.18 (br. s., 1H), 4.37-4.33 (m, 1H), 3.86-3.74 (m, 1H), 3.69-3.62 (m, 1H), 2.79-2.75 (m, 1H), 2.15-2.01 (m, 1H), 1.80 (tt, J=8.6, 5.7 Hz, 1H), 1.48 (s, 9H), 1.14-1.01 (m, 2H), 0.91-0.84 (m, 2H).

To an ice cooled solution of Intermediate 23 (0.33 g, 0.68 mmol) in 1,4-dioxane (1 mL) under argon atmosphere at rt, was added 4M HCl in 1,4-dioxane (3.0 ml, 12 mmol) and the mixture was stirred at rt for 2 h. The solvent was evaporated under reduced pressure to obtain a gummy solid. The crude product was triturated with pet. ether (10 mL×2) and dried to give Intermediate 24 (0.26 mg, 0.67 mmol, 99% yield) as a brown gummy solid. MS(ESI) m/z: 387.1 [M+H]$^+$.

Intermediate 25: tert-Butyl (1-(4-bromo-3-fluoro-2-(trifluoromethyl)phenyl)-2-oxopyrrolidin-3-yl) carbamate

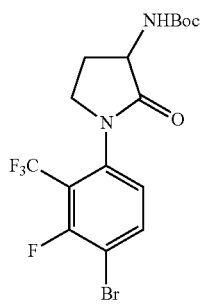 [SMILES: CC(C)(C)OC(=O)NC1CCN(c2ccc(Br)c(F)c2C(F)(F)F)C1=O]

To a stirred solution of 4-bromo-2-fluoro-3-(trifluoromethyl)aniline (0.70 g, 2.7 mmol) in Acn (10 mL) at 0° C. under nitrogen was added K$_3$PO$_4$ (0.58 g, 2.7 mmol). The resulting mixture was treated with 2,4-dibromobutanoyl chloride (0.29 mL, 2.2 mmol) and stirred for 2 h. Then, K$_2$CO$_3$ (1.1 g, 8.1 mmol) was added, and the reaction mixture was stirred for 16 h. The mixture was filtered through a Celite pad, and the pad was washed with Acn (15 mL×2). The filtrate was partially evaporated and ammonia (aq) (10 mL, 462 mmol) was added. The mixture was stirred at 40° C. for 16 h and then extracted with EtOAc (20 mL×3). The combined organics were washed with brine (20 mL), dried over Na$_2$SO$_4$ and evaporated to give crude 3-amino-1-(4-bromo-2-fluoro-3-(trifluoromethyl)phenyl)pyrrolidin-2-one (0.88 g, 2.6 mmol, 95% yield), which was used in the next step without any further purification.

To a stirred solution of crude 3-amino-1-(4-bromo-3-fluoro-2-(trifluoromethyl)phenyl)pyrrolidin-2-one in DCM (15 mL) under argon atmosphere at rt, were added TEA (3.7 mL, 26 mmol) and (Boc)$_2$O (3.4 mL, 15 mmol). The reaction mixture was stirred at rt for 6 hours and then quenched with aqueous saturated NH$_4$Cl (20 mL) and extracted with EtOAc (20 mL×3). The combined organic layers were washed with brine (20 mL), dried over Na$_2$SO$_4$, concentrated under reduced pressure and purified via column chromatography (30% EtOAc-pet. ether) to yield Intermediate 25 (4.8 g, 11 mmol, 82% yield) as a yellowish gummy solid. MS(ESI) m/z: 442.8 [M+H]$^+$. $^1$H NMR (300 MHz, CDCl$_3$) δ=7.82 (t, J=7.8 Hz, 1H), 7.02 (br. d., J=8.7 Hz, 1H), 5.23-5.05 (m, 1H), 4.43-4.23 (m, 1H), 3.80-3.53 (m, 2H), 2.89-2.68 (m, 1H), 2.21-2.03 (m, 1H), 1.47 (s, 9H).

Intermediate 26: tert-Butyl (1-(2'-(dimethylphosphoryl)-2-fluoro-3-(trifluoromethyl)-[1,1'-biphenyl]-4-yl)-2-oxopyrrolidin-3-yl)carbamate

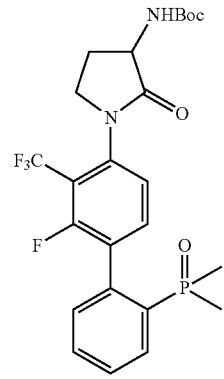 [SMILES: CC(C)(C)OC(=O)NC1CCN(c2ccc(-c3ccccc3P(C)(C)=O)c(F)c2C(F)(F)F)C1=O]

To a solution of Intermediate 25 (0.60 g, 1.4 mmol) in 1,4-dioxane (10 mL) at rt, were added (2-bromophenyl)dimethylphosphine oxide (0.41 mg, 1.8 mmol), 4,4,4',4',5,5,5',5'-octamethyl-2,2'-bi(1,3,2-dioxaborolane) (0.52 g, 2.0 mmol), and, K$_2$CO$_3$ (0.56 mg, 4.1 mmol). The reaction mixture was purged with nitrogen for 5 min and then charged with PdCl$_2$(dppf).DCM (56 mg, 0.070 mmol). The reaction mixture was again purged with nitrogen for 3 min and heated at 100° C. for 16 h. The reaction mixture was cooled, filtered through a Celite pad and the filtrate was concentrated under reduced pressure. The crude product was purified by column chromatography (EtOAc/Pet. Ether) to give the Intermediate 26 (0.30 g, 0.58 mmol, 43% yield) as an orange solid. MS(ESI) m/z: 515.1

Intermediate 27: 3-Amino-1-(2'-(dimethylphosphoryl)-2-fluoro-3-(trifluoromethyl)-[1,1'-biphenyl]-4-yl)pyrrolidin-2-one hydrochloride

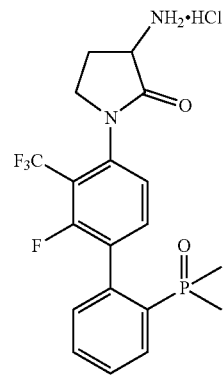

To an ice cooled solution of Intermediate 26 (0.30 g, 0.58 mmol) in 1,4-dioxane (5 mL) under argon atmosphere at rt, was added 4M HCl in 1,4-dioxane (5 mL) and stirred at rt for 2 h. The solvent was evaporated under reduced pressure. The solid was triturated with pet. ether (10 ml×2) and dried to give the Intermediate 27 (0.20 g, 0.48 mmol, 83% yield) as a brown gummy solid. MS(ESI) m/z: 415.1 [M+H]$^+$.

Intermediate 28: (S)-1-(4-Bromo-2,3-difluorophenyl)-5-(hydroxymethyl)pyrrolidin-2-one

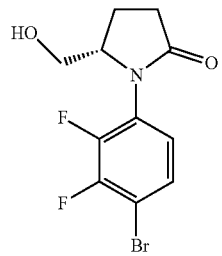

To a solution of (S)-5-(hydroxymethyl)pyrrolidin-2-one (1.0 g, 8.7 mmol) in 1,4-dioxane (15 mL) at rt, were added 1,4-dibromo-2,3-difluorobenzene (2.4 g, 8.7 mmol), $K_3PO_4$ (3.7 g, 17 mmol) and, N,N'-dimethylethylenediamine (0.15 g, 1.7 mmol). The reaction mixture was purged with nitrogen for 5 min and then charged with copper (I) iodide (0.17 g, 0.87 mmol). The reaction mixture was again purged with nitrogen for 3 min and heated at 95° C. for 12 h. The reaction mixture was cooled, filtered through a Celite pad and the filtrate was concentrated under reduced pressure. The crude compound was purified by column chromatography (3% MeOH—$CHCl_3$) to yield Intermediate 28 (0.80 g, 2.6 mmol, 30% yield) as a yellowish solid. MS(ESI) m/z: 305.9 $[M+H]^+$. $^1H$ NMR (400 MHz, DMSO-$d_6$) δ=7.59 (ddd, J=8.8, 7.0, 2.3 Hz, 1H), 7.24 (ddd, J=9.0, 7.0, 2.0 Hz, 1H), 4.80 (t, J=5.0 Hz, 1H), 4.20-4.04 (m, 1H), 3.37 (dd, J=5.0, 4.0 Hz, 2H), 2.56-2.45 (m, 1H), 2.43-2.35 (m, 1H), 2.25-2.18 (m, 1H), 2.07-1.95 (m, 1H).

Intermediate 29: (S)-1-(4-Bromo-2,3-difluorophenyl)-5-(((tert-butyldimethylsilyl)oxy)methyl)pyrrolidin-2-one

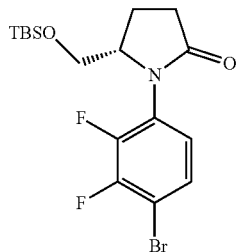 [SMILES: CC(C)(C)[Si](C)(C)OC[C@@H]1CCC(=O)N1c1ccc(Br)c(F)c1F]

To a stirred solution of Intermediate 28 (0.80 g, 2.6 mmol) in DCM (10 mL) under argon atmosphere at rt, were added TEA (0.55 mL, 3.9 mmol) and tert-butyldimethylsilyl chloride (0.43 g, 2.9 mmol). The reaction mixture was stirred at rt for 16 h. The reaction mixture was quenched with aqueous saturated $NH_4Cl$ (20 mL) and extracted with DCM (20 mL×2). The combined organic layers were washed with brine (20 mL), dried over $Na_2SO_4$, concentrated under reduced pressure. The crude product was purified via column chromatography (15% EtOAc-Pet. ether) to give Intermediate 29 (0.85 g, 2.0 mmol, 77% yield) as a white solid. MS(ESI) m/z: 420.2 $[M+H]^+$. $^1H$ NMR (400 MHz, $CDCl_3$) δ=7.35 (m, 1H), 7.15-7.05 (m, 1H), 4.24-4.17 (m, 1H), 3.62-3.49 (m, 2H), 2.69-2.63 (m, 1H), 2.54-2.50 (m, 1H), 2.41-2.26 (m, 1H), 2.14-2.03 (m, 1H), 0.84 (s, 9H), −0.02 (s, 3H), −0.05 (s, 3H).

Intermediate 30: (3R,5S)-3-azido-1-(4-bromo-2,3-difluorophenyl-5-(((tert-butyldimethylsilyl)oxy)methyl)pyrrolidin-2-one

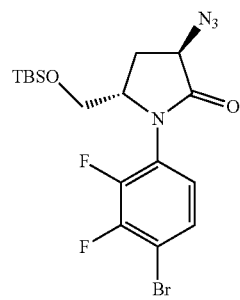 [SMILES: CC(C)(C)[Si](C)(C)OC[C@@H]1C[C@@H](N=[N+]=[N-])C(=O)N1c1ccc(Br)c(F)c1F]

To a stirred solution of Intermediate 29 (1.0 g, 2.4 mmol) in THF (20 mL) at −78° C., lithium diisopropylamide (1.8 mL, 3.6 mmol) was added and stirring was continued for 30 min. Then, a solution of 2,4,6-triisopropylbenzenesulfonyl azide (1.0 g, 3.3 mmol) in THF (5 mL) was cannulated into the mixture and the mixture was stirred for 4 h. Then, the reaction mixture was quenched with saturated aqueous $NaHCO_3$ (2 mL) and gradually warmed to rt. The reaction mixture was diluted with EtOAc (40 mL), washed with $H_2O$ (10 mL×2) and brine (20 mL), dried over $Na_2SO_4$, and concentrated under reduced pressure. The crude residue was purified by column chromatography (15% EtOAc-Pet ether, 40 g column) to yield Intermediate 30 (0.85 g, 1.8 mmol, 77% yield) as an orange solid. MS(ESI) m/z: 461.1 $[M+H]^+$. $^1H$ NMR (400 MHz, DMSO-$d_6$) δ=7.65 (ddd, J=9.0, 7.0, 2.0 Hz, 1H), 7.36-7.28 (m, 1H), 4.72-4.64 (m, 1H), 4.33-4.24 (m, 1H), 3.63-3.52 (m, 2H), 2.48-2.28 (m, 1H), 2.14 (dt, J=13.3, 8.7 Hz, 1H), 0.91-0.66 (m, 9H), −0.06 (s, 3H), −0.08 (s, 3H).

Intermediate 31: tert-Butyl ((3R,5S)-1-(4-bromo-2,3-difluorophenyl)-5-(((tert-butyldimethylsilyl)oxy)methyl)-2-oxopyrrolidin-3-yl)carbamate

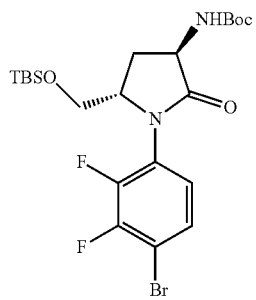 [SMILES: CC(C)(C)OC(=O)N[C@@H]1C[C@@H](CO[Si](C)(C)C(C)(C)C)N(c2ccc(Br)c(F)c2F)C1=O]

To a stirred solution Intermediate 30 (0.85 g, 1.8 mmol) in THF (8 mL) were added triphenylphosphine (0.73 g, 2.8 mmol) and $H_2O$ (0.8 mL). The reaction mixture was stirred at rt for 3 h and heated at 65° C. for 6 h. The solvent was evaporated under reduced pressure and used for the next step without further purification. To a stirred solution of crude (5S)-3-amino-1-(4-bromo-2,3-difluorophenyl)-5-(((tert-butyldimethylsilyl)oxy)methyl)pyrrolidin-2-one in DCM (5 mL) under argon atmosphere at rt, were added Boc-anhydride (0.84 mL, 3.6 mmol) and TEA (0.75 mL, 5.4 mmol. The reaction mixture was stirred at rt for 2 h. Then, the reaction mixture was quenched with aqueous saturated NH₄Cl (15 mL) and extracted with CHCl₃ (20 mL×2). The combined organic layers were washed with brine (15 mL), dried over Na₂SO₄, concentrated under reduced pressure. The crude product was purified via column chromatography (15% EtOAc-Pet. ether) to give Intermediate 31 (0.80 g, 1.5 mmol, 83% yield) as a white solid. MS(ESI) m/z: 535.2 [M+H]⁺. ¹H NMR (400 MHz, CDCl₃) δ=7.41-7.32 (m, 1H), 7.15-7.01 (m, 1H), 5.02-5.22 (m, 1H), 4.73-4.61 (m, 1H), 4.52-4.43 (m, 1H), 4.21-4.10 (m, 1H), 3.61-3.52 (m, 1H), 2.63-2.51 (m, 1H), 2.35-2.31 (m, 1H), 1.43 (s, 9H), 0.84 (s, 9H), −0.06 (s, 3H), −0.08 (s, 3H).

Intermediate 32: tert-Butyl ((3R,5S)-5-(((tert-butyldimethylsilyl)oxy)methyl)-1-(2'-(dimethylphosphoryl)-2,3-difluoro-[1,1'-biphenyl]-4-yl)-2-oxopyrrolidin-3-yl)carbamate

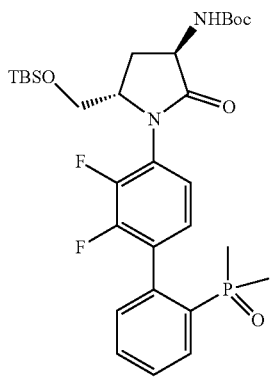 [SMILES: CC(C)(C)OC(=O)N[C@@H]1C[C@@H](CO[Si](C)(C)C(C)(C)C)N(c2ccc(-c3ccccc3P(C)(C)=O)c(F)c2F)C1=O]

To a stirred solution of Intermediate 31 (0.80 g, 1.49 mmol) in 1,4-dioxane (10 mL), were added (2-bromophenyl)dimethylphosphine oxide (0.52 g, 2.2 mmol), bis(pinacolato)diboron (1.1 g, 4.5 mmol), and K₂CO₃ (0.42 mg, 3.0 mmol). The reaction mixture was purged with argon for 5 min and charged with PdCl₂(dppf)-CH₂Cl₂ adduct (0.13 mg, 0.15 mmol). The reaction mixture was again purged with nitrogen for 3 min and heated at 100° C. for 12 h. The reaction mixture was cooled, filtered through a Celite pad and the filtrate was concentrated under reduced pressure. The crude product was purified by column chromatography (MeOH/CHCl₃) to yield Intermediate 32 (0.40 g, 0.66 mmol, 44% yield) as a brown solid MS(ESI) m/z: 609.3 [M+H]⁺. ¹H NMR (400 MHz, DMSO-d₆) δ=8.01-7.97 (m, 1H), 7.85-7.81 (m, 1H), 7.80-7.64 (m, 2H), 7.59-7.27 (m, 3H), 4.66-4.56 (m, 1H), 4.42-4.33 (m, 1H), 3.76-3.55 (m, 2H), 2.46-2.28 (m, 2H), 1.54-1.39 (m, 15H), 0.84 (s, 9H), 0.06 (s, 3H), −0.08 (s, 3H).

Intermediate 33: (3R,5S)-3-amino-1-(2'-(dimethylphosphoryl)-2,3-difluoro-[1,1'-biphenyl]-4-yl)-5-(hydroxymethyl)pyrrolidin-2-one hydrochloride

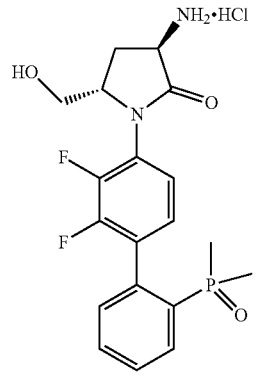

To an ice cooled solution of Intermediate 32 (0.40 g, 0.66 mmol) in 1,4-dioxane (1 mL) under argon atmosphere at rt, was added 4M HCl in 1,4-dioxane (2.5 mL, 10 mmol) and stirred at rt for two h. The solvent was evaporated under reduced pressure and the gummy solid was further triturated with EtOAc (10 ml×2) and dried to give Intermediate 33 (0.22 g, 0.56 mmol, 85% yield) as a brown solid. MS(ESI) m/z: 395.1 [M+H]⁺. ¹H NMR (400 MHz, DMSO-d₆) δ=7.97-7.88 (m, 1H), 7.82-7.72 (m, 1H), 7.69-7.47 (m, 2H), 7.43-7.25 (m, 2H), 4.35-4.29 (m, 2H), 4.11-3.86 (m, 4H), 3.55-3.34 (m, 2H), 2.48-2.27 (m, 2H), 1.52 (br d, J=13.1 Hz, 6H).

Intermediate 34: 1-(4-Bromo-2,3-difluorophenyl)-5-methylpyrrolidin-2-one

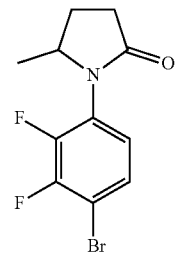 [SMILES: CC1CCC(=O)N1c1ccc(Br)c(F)c1F]

To a solution of racemic 5-methylpyrrolidin-2-one (1.0 g, 10 mmol) in 1,4-dioxane (10 mL) at rt, were added 1,4-dibromo-2,3-difluorobenzene (3.3 g, 12 mmol), K₃PO₄ (4.3 g, 20 mmol) and N,N-dimethylethylenediamine (0.18 g, 2.0 mmol). The reaction mixture was purged with nitrogen for 5 min and then charged with copper (I) iodide (0.19 g, 1.0 mmol). The reaction mixture was again purged with nitrogen for 3 min and heated at 80° C. for 6 h. The reaction mixture was cooled, filtered through a Celite pad and the filtrate was concentrated under reduced pressure. The crude product was purified by column chromatography (pet. ether-EtOAc) to give Intermediate 34 (0.90 g, 3.1 mmol, 31% yield) as brown liquid. MS(ESI) m/z: 291.0 [M+H]⁺. ¹H NMR (400 MHz, CDCl₃) δ=7.38-7.01 (m, 1H), 6.99-6.96 (m, 1H), 4.24-4.20 (m, 1H), 2.62-2.51 (m, 2H), 2.50-2.38 (m, 1H), 1.81-1.76 (m, 1H), 1.17 (d, J=6.4 Hz, 3H).

Intermediate 35: 3-Azido-1-(4-bromo-2,3-difluorophenyl)-5-methylpyrrolidin-2-one

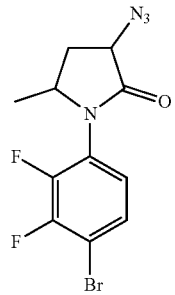 [SMILES: CC1CC(N=[N+]=[N-])C(=O)N1c1ccc(Br)c(F)c1F]

To a stirred solution of Intermediate 34 (0.20 g, 0.69 mmol) in THF (3 mL) at −78° C., lithium diisopropylamide (0.69 mL, 1.4 mmol) was added and stirring was continued for 40 min. Then, a solution of 2,4,6-triisopropylbenzenesulfonyl azide (0.26 g, 0.83 mmol) in THF (2 mL) was cannulated into the mixture and the mixture was stirred for 4 h. The mixture was then quenched with saturated aqueous NH$_4$Cl (10 mL), gradually warmed to rt and extracted with EtOAc (20 mL×2). The combined organic layers were washed with brine (15 mL), dried over Na$_2$SO$_4$, and concentrated under reduced pressure. The crude residue was purified by column chromatography (12% EtOAc-Pet ether) to yield Intermediate 35 (0.10 g, 0.21 mmol, 31% yield) as an orange solid. MS(ESI) m/z: 331.1 [M+H]$^+$. $^1$H NMR (400 MHz, CDCl$_3$) δ=7.40-7.36 (m, 1H), 7.04-6.98 (m, 1H), 4.36-4.31 (m, 1H), 4.26-4.21 (m, 1H), 2.32-2.26 (m, 1H), 2.14-2.043 (m, 1H), 1.16 (d, J=6.4 Hz, 3H).

Intermediate 36: tert-Butyl (1-(4-bromo-2,3-difluorophenyl)-5-methyl-2-oxopyrrolidin-3-yl)carbamate

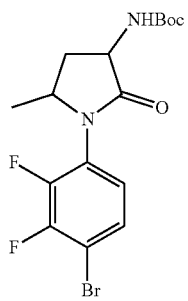

To a stirred solution 3-azido-1-(4-bromo-2,3-difluorophenyl)-5-methylpyrrolidin-2-one (1.5 g, 4.5 mmol) in THF (21 mL) were added triphenylphosphine (2.4 g, 9.1 mmol) and water (3 mL). The reaction mixture was stirred at rt for 30 min and heated to 65° C. for 6 h. The solvent was evaporated under reduced pressure and the crude product used for the next step without further purification.

To a stirred solution of crude 3-amino-1-(4-bromo-2,3-difluorophenyl)-5-methylpyrrolidin-2-one in DCM (20 mL) under argon atmosphere at rt, were added TEA (0.82 mL, 5.9 mmol) and Boc-anhydride (1.4 mL, 5.9 mmol). The reaction mixture was stirred at rt for 2 h. Then, the reaction mixture was quenched with aqueous saturated NH$_4$Cl (25 mL) and extracted with CHCl$_3$ (30 mL×2). The combined organic layers were washed with brine (25 mL), dried over Na$_2$SO$_4$, and concentrated under reduced pressure. The crude product was purified via column chromatography (50% EtOAc-Pet. ether) to give Intermediate 36 (1.3 g, 3.2 mmol, 82% yield) as a brown solid. MS(ESI) m/z: 405.2 [M+H]$^+$. $^1$H NMR (400 MHz, CDCl$_3$) δ=7.39-7.26 (m, 1H), 7.0-6.99 (m, 1 H), 5.29-5.07 (m, 1H), 4.58-4.31 (m, 1H), 4.30-4.13 (m, 1H), 2.51-2.04 (m, 1H), 1.81-1.76 (m, 1H), 1.45 (s, 9H), 1.30-1.15 (m, 3H). (Mixture of diastereomers)

Intermediate 37: tert-Butyl (1-(2'-(dimethylphosphoryl)-2,3-difluoro-[1,1'-biphenyl]-4-yl)-5-methyl-2-oxopyrrolidin-3-yl)carbamate

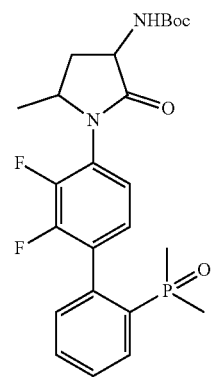

To a stirred solution of Intermediate 36 (1.0 g, 2.5 mmol) in 1,4-dioxane (15 mL), were added (2-bromophenyl)dimethylphosphine oxide (0.58 g, 2.5 mmol), bis(pinacolato)diboron (1.9 g, 7.4 mmol) and K$_2$CO$_3$ (1.0 g, 7.4 mmol). The reaction mixture was purged with nitrogen for 5 min and charged with PdCl$_2$(dppf).CH$_2$Cl$_2$ adduct (0.20 g, 0.25 mmol). The reaction mixture was again purged with nitrogen for 3 min and heated at 110° C. for 15 h. The mixture was cooled, filtered through a Celite pad and the filtrate was concentrated under reduced pressure. The crude compound was purified by flash chromatography (MeOH/CDCl$_3$) to give Intermediate 37 (0.70 g, 1.5 mmol, 59% yield) as a brown solid. MS(ESI) m/z: 479.2 [M+H]$^+$. $^1$H NMR (400 MHz, CDCl$_3$) δ=7.78-7.73 (m, 1H), 7.62-7.51 (m, 3H), 7.37-7.28 (m, 1H), 7.23-7.18 (m, 1H), 5.31-5.11 (m, 1H), 4.59-4.24 (m, 2H), 2.58-2.32 (m, 1H), 1.77-1.74 (m, 3H), 1.65-1.49 (m, 13H), 1.30-1.23 (m, 3H). (Mixture of diastereomers)

Intermediate 38: 3-Amino-1-(2'-(dimethylphosphoryl)-2,3-difluoro-[1,1'-biphenyl]-4-yl)-5-methylpyrrolidin-2-one hydrochloride

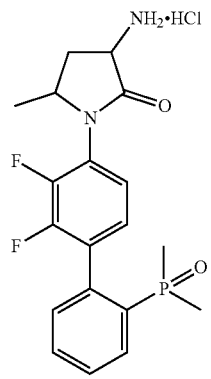

To an ice cooled solution of Intermediate 37 (0.70 g, 1.5 mmol) in 1,4-dioxane (5 mL) under argon atmosphere, was added 4M HCl (7.3 mL, 29 mmol) in 1,4-dioxane and stirred at rt for 2 h. The solvent was evaporated under reduced pressure to give Intermediate 38 (0.50 g, 1.2 mmol, 82% yield) as brown liquid. MS(ESI) m/z: 379.2 [M+H]$^+$. $^1$H NMR (400 MHz, CDCl$_3$) δ=7.78-7.73 (m, 1H), 7.62-7.51 (m, 3H), 7.37-7.28 (m, 1H), 7.23-7.18 (m, 1H), 5.38-4.98 (m, 3H), 4.59-4.42 (m, 2H), 2.58-2.29 (m, 1H), 1.71-1.63 (m, 3H), 1.55-1.49 (m, 4H), 1.30-1.23 (m, 3H).

Example 1: (R)—N-(4'-(3-(3-(4-Chlorophenyl)ureido)-2-oxopyrrolidin-1-yl)-2',3'-difluoro-[1,1'-biphenyl]-2-yl)methanesulfonamide

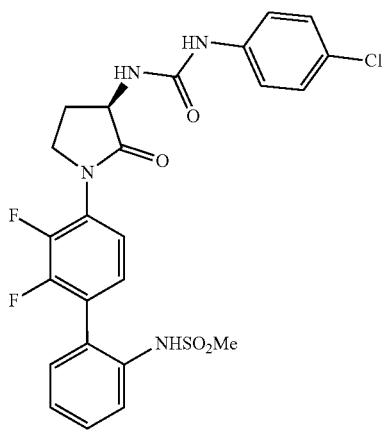

To a stirred solution of Intermediate 5 (50 mg, 0.12 mmol), in DCE (2 mL) under nitrogen at rt, DIPEA (0.084 mL, 0.48 mmol), and 1-chloro-4-isocyanatobenzene (22.0 mg, 0.144 mmol) were added sequentially. The resulting reaction mixture was stirred at rt for 4 h. The reaction mixture was quenched with water and extracted with EtOAc. The organic layer was washed with ice cold water, brine, dried over Na$_2$SO$_4$, and concentrated under reduced pressure. The crude compound was purified by reverse phase chromatography followed by chiral HPLC to Example 1 (16 mg, 0.028 mmol, 24%). RT=1.732 min, 94.2%, (Method C); MS(ESI) m/z: 535.1 [M+H]$^+$; $^1$H NMR (400 MHz, DMSO-d$_6$): δ 9.17 (s, 1H), 8.87 (s, 1H), 7.96 (s, 1H), 7.58-7.29 (m, 10H), 4.64-4.48 (m, 1H), 3.96-3.82 (m, 1H), 3.81-3.66 (m, 1H), 2.74 (s, 3H), 2.59-2.55 (m, 1H), 2.20-2.07 (m, 1H).

Example 25: (R)-1-(4-chloro-2-fluorophenyl)-3-(1-(2'-(dimethylphosphoryl)-2,3-difluoro-[1,1'-biphenyl]-4-yl)-2-oxopyrrolidin-3-yl)urea

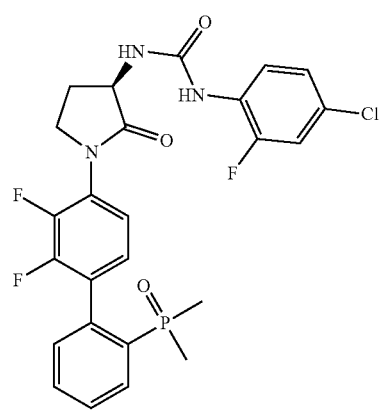 [SMILES: CP(C)(=O)c1ccccc1-c1ccc(N2CC[C@@H](NC(=O)Nc3ccc(Cl)cc3F)C2=O)c(F)c1F]

DIEA (61 mL, 350 mmol) was added to a solution of Intermediate 10 (28 g, 70 mmol) in DCE (560 mL) slowly at 0° C. After stirring for 2 min, Intermediate 11 (17 g, 63 mmol) was added, and the reaction mixture was slowly heated to 50° C. and stirred for 12 h. The reaction mixture was concentrated under reduced pressure, and the crude product was purified via column chromatography (5% MeOH in DCM). The product was purified by prep HPLC, washed with water, and dried to obtain Example 25 (29 g, 54 mmol, 78% yield) as a white solid.

Example 57: (R)-1-(1-(2'-(dimethylphosphoryl)-2,3-difluoro-[1,1'-biphenyl]-4-yl)-2-oxopyrrolidin-3-yl)-3-(2-fluoro-4-(trifluoromethyl)phenyl) urea

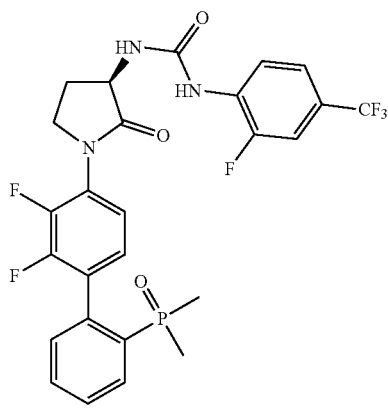 [SMILES: CP(C)(=O)c1ccccc1-c1ccc(N2CC[C@@H](NC(=O)Nc3ccc(C(F)(F)F)cc3F)C2=O)c(F)c1F]

DIEA (5.5 mL, 6.2 mmol) was added to a solution of Intermediate 10 (2.5 g, 6.2 mmol) in DCE (70 mL) slowly at 0° C. After stirring for 2 min, Intermediate 12 (1.7 g, 5.6 mmol) was added, and the reaction mixture was slowly heated to 50° C. and stirred for 8 h. The reaction mixture was concentrated under reduced pressure and the crude product was purified via column chromatography (6.5% MeOH in DCM). The product was purified by prep HPLC, washed with water, and dried to obtain Example 57 (2.2 g, 3.9 mmol, 62% yield) as a white solid.

Example 73: (R)-1-(1-(4-(2-(dimethylphosphoryl)pyridin-3-yl)-2,3-difluorophenyl)-2-oxopyrrolidin-3-yl)-3-(2-fluoro-4-(trifluoromethyl)phenyl) urea

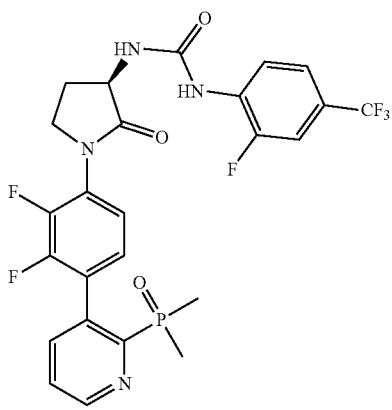 [SMILES: CP(C)(=O)c1ncccc1-c1ccc(N2CC[C@@H](NC(=O)Nc3ccc(C(F)(F)F)cc3F)C2=O)c(F)c1F]

To a solution of Intermediate 14 (13 g, 24 mmol) and Intermediate 15 (5.6 g, 24 mmol) in 1,4 dioxane (260 mL) and water (26 mL), were added potassium phosphate (10 g, 48 mmol) and PdCl$_2$(dppf)-CH$_2$Cl$_2$ (2.0 g, 2.4 mmol). The reaction mixture was stirred for 30 min, slowly raised to 110° C. and stirred for 12 h. The mixture was filtered through Celite, and the plug was washed with EtOAc. The filtrate was dried over sodium sulfate and concentrated under reduced pressure. The crude compound was purified via column chromatography (2% MeOH in DCM) to yield Example 73 (9.1 g, 16 mmol, 66% yield).

Example 89: (R)-1-(1-(2-Cyclopropyl-2'-(dimethylphosphoryl)-3-fluoro-[1,1'-biphenyl]-4-yl)-2-oxopyrrolidin-3-yl)-3-(2-fluoro-4-(trifluoromethyl)phenyl) urea

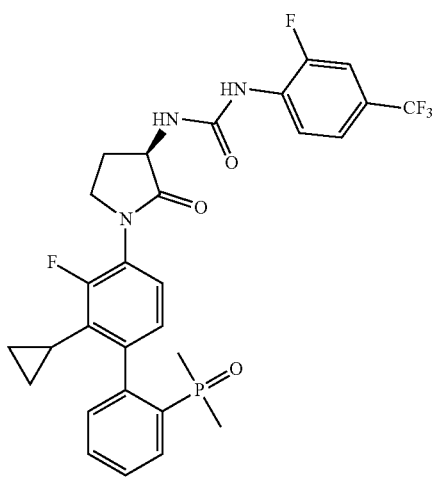 [SMILES: CP(C)(=O)c1ccccc1-c1ccc(N2CC[C@@H](NC(=O)Nc3ccc(C(F)(F)F)cc3F)C2=O)c(F)c1C1CC1]

To an ice cooled suspension of Intermediate 24 (0.13 g, 0.34 mmol) in DMF (2 mL) under argon atmosphere at rt, were added DIEA (0.18 mL, 1.0 mmol) and Intermediate 12 (0.12 g, 0.41 mmol). Then, the resulting solution was heated at 50° C. for 2 hours. The reaction mixture was concentrated under reduced pressure and the crude product was purified by reverse phase chromatography followed by chiral HPLC to give Example 89 (0.07 g, 0.12 mmol, 33% yield).

Example 91: (R)-1-(4-Chloro-2-fluorophenyl)-3-(1-(2'-(dimethylphosphoryl)-2-fluoro-3-(trifluoromethyl)-[1,1'-biphenyl]-4-yl)-2-oxopyrrolidin-3-yl) urea

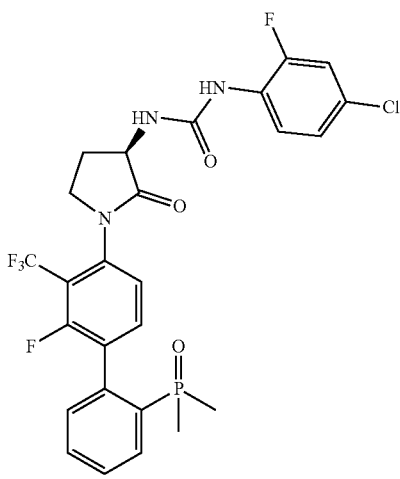 [SMILES: CP(C)(=O)c1ccccc1-c1ccc(N2CC[C@@H](NC(=O)Nc3ccc(Cl)cc3F)C2=O)c(C(F)(F)F)c1F]

To an ice cooled suspension of Intermediate 27 (0.080 g, 0.18 mmol) in DCE (2 mL) under argon atmosphere at rt, were added DIEA (0.06 mL, 0.36 mmol) and Intermediate 11 (0.060 g, 0.21 mmol). Then, the resulting solution was heated at 50° C. for 2 h. The reaction mixture was concentrated under reduced pressure, and the crude product was purified by reverse phase chromatography followed by chiral HPLC to yield Example 91 (0.060 g, 0.11 mmol, 60% yield) as a white solid.

Example 109: 1-(4-Chloro-2-fluorophenyl)-3-(1-(2'-(dimethylphosphoryl)-2,3-difluoro-[1,1'-biphenyl]-4-yl)-5-methyl-2-oxopyrrolidin-3-yl) urea Example 112: 1-(4-Chloro-2-fluorophenyl)-3-((3R,5S)-1-(2'-(dimethylphosphoryl)-2,3-difluoro-[1,1'-biphenyl]-4-yl)-5-(hydroxymethyl)-2-oxopyrrolidin-3-yl)urea

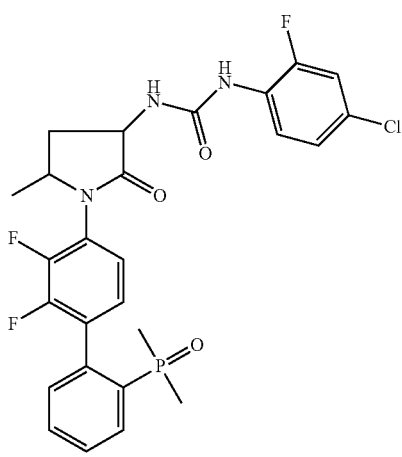 [SMILES: CC1CC(NC(=O)Nc2ccc(Cl)cc2F)C(=O)N1c1ccc(-c2ccccc2P(C)(C)=O)c(F)c1F]

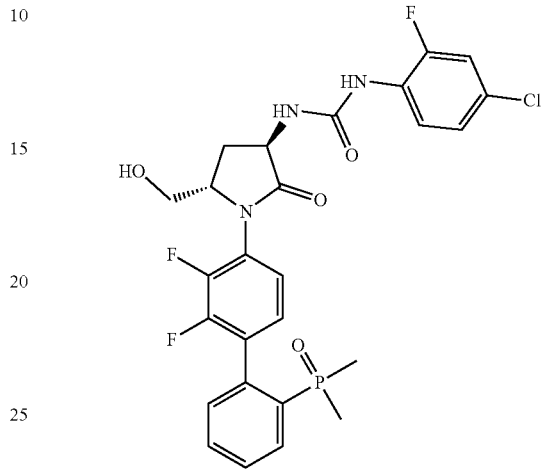

To an ice cooled suspension of Intermediate 38 (0.20 g, 0.48 mmol) in DCE (10 mL) under argon atmosphere at rt, were added DIEA (0.34 mL, 1.9 mmol) and Intermediate 11 (73 mg, 0.25 mmol). Then, the resulting solution was heated at 50° C. for 3 h. The reaction mixture was concentrated under reduced pressure and the crude product was purified by reverse phase chromatography followed by chiral HPLC to yield Example 109 (0.02 g, 0.04 mmol, 8.3% yield) as a white solid.

To an ice cooled suspension of Intermediate 22 (0.11 g, 0.28 mmol) in DMF (2 mL) under argon atmosphere at rt, were added DIEA (0.15 mL, 0.84 mmol) and Intermediate 11 (0.11 g, 0.42 mmol). Then, the resulting solution was heated at 50° C. for 3 h. The reaction mixture was concentrated under reduced pressure and the crude product was purified by reverse phase chromatography followed by chiral HPLC to yield Example 112 (0.05 g, 0.08 mmol, 29% yield).

The following Examples in Table 1 were made by using the same procedure as shown above in Examples 1, 25, 57, 73, 89, 91, 109, and 112.

| Ex | Structure | LCMS (M + H)+ | HPLC Method, RT (min.) & Purity | $^1$H NMR |
|---|---|---|---|---|
| 2 | 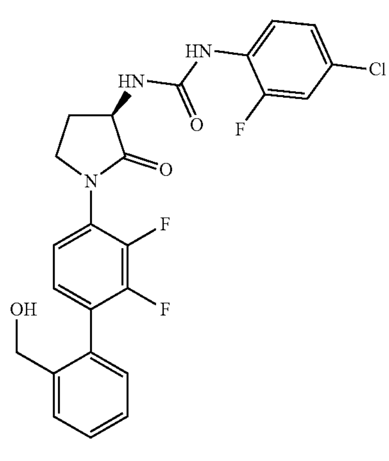 [SMILES: O=C(Nc1ccc(Cl)cc1F)N[C@@H]1CCN(c2ccc(-c3ccccc3CO)c(F)c2F)C1=O] | 490.1 | Method D, RT = 1.75 min, 99.3% | $^1$H NMR (400 MHz, DMSO-d$_6$) δ = 8.64 (d, J = 2.2 Hz, 1H), 8.16 (t, J = 8.8 Hz, 1H), 7.63 (d, J = 7.6 Hz, 1H), 7.54-7.32 (m, 4H), 7.31-7.08 (m, 4H), 5.16 (t, J = 5.5 Hz, 1H), 4.63-4.48 (m, 1H), 4.35 (d, J = 5.4 Hz, 2H), 3.97-3.85 (m, 1H), 3.84-3.74 (m, 1H), 2.65-2.56 (m, 1H), 2.16-2.03 (m, 1H). |

-continued

| Ex | Structure | LCMS (M + H)+ | HPLC Method, RT (min.) & Purity | ¹H NMR |
|---|---|---|---|---|
| 3 | 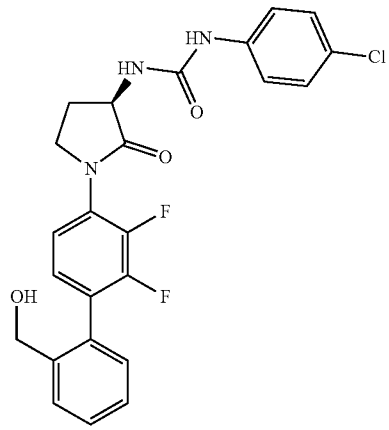 [SMILES: O=C(Nc1ccc(Cl)cc1)N[C@@H]1CCN(c2ccc(-c3ccccc3CO)c(F)c2F)C1=O] | 472.1 | Method D, RT = 1.89 min, 98.9% | ¹H NMR (400 MHz, DMSO-d$_6$) δ = 8.86 (s, 1H), 7.63 (d, J = 7.6 Hz, 1H), 7.54-7.34 (m, 5H), 7.34-7.14 (m, 4H), 6.72 (d, J = 7.3 Hz, 1H), 5.16 (t, J = 5.4 Hz, 1H), 4.55 (dt, J = 10.1, 8.1 Hz, 1H), 4.35 (d, J = 5.4 Hz, 2H), 3.95-3.83 (m, 1H), 3.83-3.72 (m, 1H), 2.60-2.54 (m, 1H), 2.19-2.06 (m, 1H). |
| 4 | 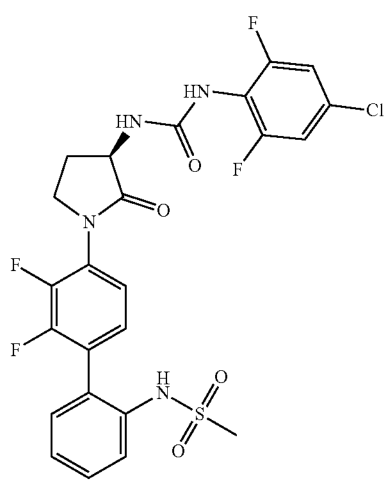 [SMILES: CS(=O)(=O)Nc1ccccc1-c1ccc(N2CC[C@@H](NC(=O)Nc3c(F)cc(Cl)cc3F)C2=O)c(F)c1F] | 588.2 (M + NH$_4$)$^+$ | Method D, RT = 1.66 min, 95.2% | ¹H NMR (400 MHz, DMSO-d$_6$) δ = 9.18 (s, 1H), 8.21 (s, 1H), 7.97 (s, 1H), 7.60-7.45 (m, 2H), 7.45-7.31 (m, 4H), 7.26-7.20 (m, 1H), 7.03-6.97 (m, 1H), 4.60-4.52 (m, 1H), 3.98-3.82 (m, 2H), 3.79-3.73 (m, 1H), 2.87 (s, 3H), 2.18-2.06 (m, 1H). |
| 5 | 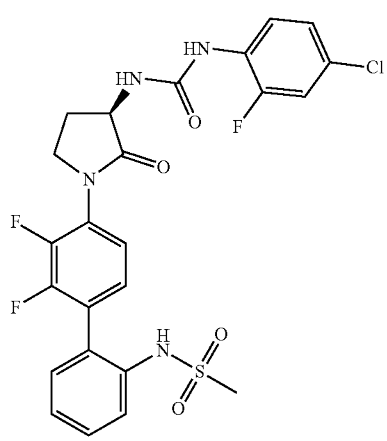 [SMILES: CS(=O)(=O)Nc1ccccc1-c1ccc(N2CC[C@@H](NC(=O)Nc3ccc(Cl)cc3F)C2=O)c(F)c1F] | 553.1 | Method C, RT = 1.79 min, 96.8% | ¹H NMR (400 MHz, DMSO-d$_6$) δ = 9.18 (s, 1H), 8.65 (d, J = 2.2 Hz, 1H), 8.16 (t, J = 8.9 Hz, 1H), 7.56-7.29 (m, 6H), 7.29-7.13 (m, 3H), 4.64-4.48 (m, 1H), 3.96-3.87 (m, 1H), 3.78-3.74 (m, 1H), 2.74 (s, 3H), 2.62-2.56 (m, 1H), 2.13-2.01 (m, 1H). |

| Ex | Structure | LCMS (M + H)+ | HPLC Method, RT (min.) & Purity | $^1$H NMR |
|---|---|---|---|---|
| 6 | 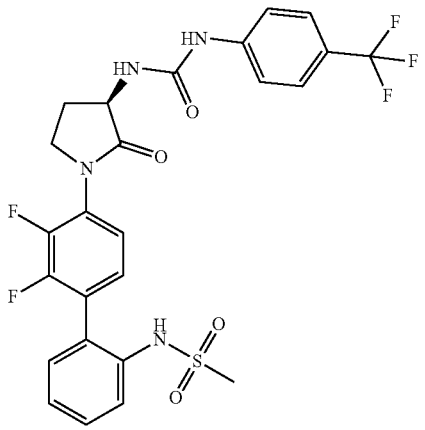 [SMILES: CS(=O)(=O)Nc1ccccc1-c1ccc(N2CC[C@@H](NC(=O)Nc3ccc(C(F)(F)F)cc3)C2=O)c(F)c1F] | 569.1 | Method C, RT = 1.86 min, 97.2% | $^1$H NMR (400 MHz, DMSO-d$_6$) δ = 9.16 (s, 1H), 7.96 (s, 1H), 7.70-7.56 (m, 4H), 7.55-7.45 (m, 2H), 7.44-7.30 (m, 3H), 7.28-7.20 (m, 1H), 6.86 (d, J = 7.6 Hz, 1H), 4.60-4.54 (m, 1H), 3.96-3.86 (m, 1H), 3.77-3.75 (m, 1H), 2.74 (s, 3H), 2.61-2.54 (m, 1H), 2.21-2.06 (m, 1H). |
| 7 | 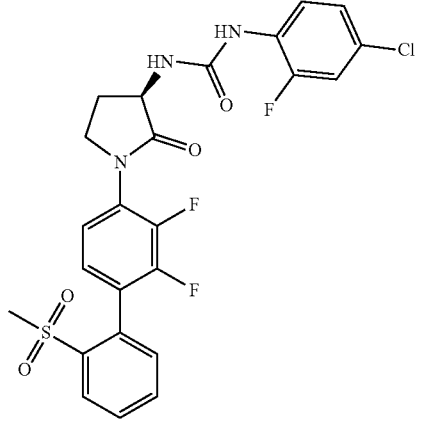 [SMILES: CS(=O)(=O)c1ccccc1-c1ccc(N2CC[C@@H](NC(=O)Nc3ccc(Cl)cc3F)C2=O)c(F)c1F] | 538.2 | Method D, RT = 1.75 min, 95.9% | $^1$H NMR (400 MHz, DMSO-d$_6$) δ = 8.65 (s, 1H), 8.23-8.05 (m, 2H), 7.91-7.68 (m, 2H), 7.51 (d, J = 7.3 Hz, 1H), 7.46-7.35 (m, 2H), 7.35-7.25 (m, 1H), 7.20-7.18 (m, 2H), 4.63-4.48 (m, 1H), 3.94-3.87 (m, 1H), 3.83-3.69 (m, 1H), 3.05 (s, 3H), 2.63-2.54 (m, 1H), 2.10-2.05 (m, 1H). |
| 8 | 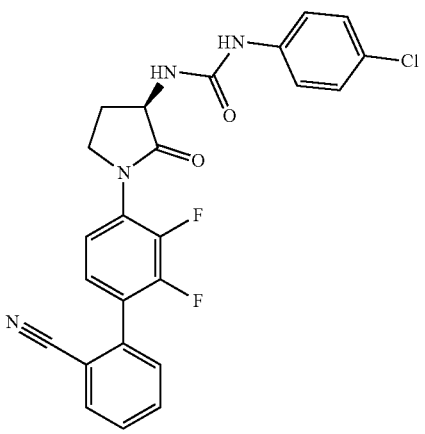 [SMILES: N#Cc1ccccc1-c1ccc(N2CC[C@@H](NC(=O)Nc3ccc(Cl)cc3)C2=O)c(F)c1F] | 467.2 | Method D, RT = 1.85 min, 100% | $^1$H NMR (400 MHz, DMSO-d$_6$) δ = 8.88 (s, 1H), 8.05 (d, J = 8.1 Hz, 1H), 7.96-7.85 (m, 1H), 7.79-7.63 (m, 2H), 7.59-7.49 (m, 1H), 7.49-7.37 (m, 3H), 7.30 (d, J = 8.8 Hz, 2H), 6.75 (d, J = 7.6 Hz, 1H), 4.63-4.51 (m, 1H), 3.98-3.87 (m, 1H), 3.87-3.73 (m, 1H), 2.58 (br. s., 1H), 2.18-2.11 (m, 1H). |

-continued

| Ex | Structure | LCMS (M + H)+ | HPLC Method, RT (min.) & Purity | ¹H NMR |
|---|---|---|---|---|
| 9 | 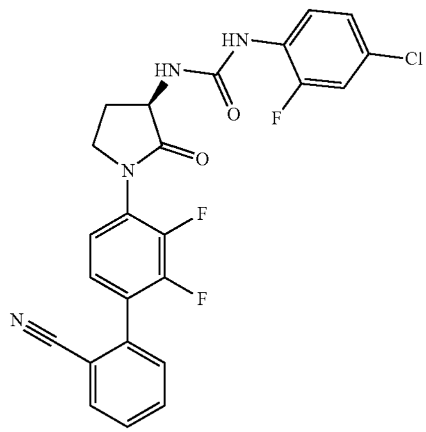 [SMILES: N#Cc1ccccc1-c1ccc(N2CC[C@@H](NC(=O)Nc3ccc(Cl)cc3F)C2=O)c(F)c1F] | 485.1 | Method D, RT = 1.91 min, 96.8% | ¹H NMR (400 MHz, DMSO-d$_6$) δ = 8.65 (s, 1H), 8.15 (t, J = 8.9 Hz, 1H), 8.04 (d, J = 7.9 Hz, 1H), 7.94-7.83 (m, 1H), 7.78-7.60 (m, 2H), 7.57-7.49 (m, 1H), 7.48-7.34 (m, 2H), 7.20 (d, J = 7.6 Hz, 2H), 4.64-4.52 (m, 1H), 3.98-3.88 (m, 1H), 3.86-3.76 (m, 1H), 2.65-2.55 (m, 1H), 2.18-2.00 (m, 1H). |
| 10 | 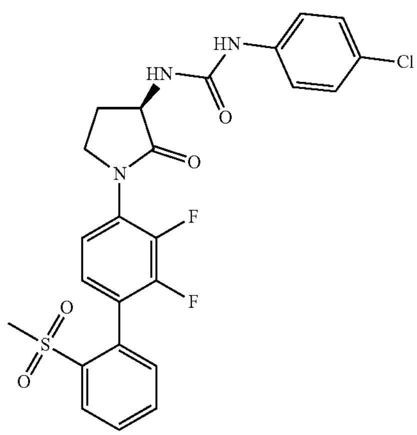 [SMILES: CS(=O)(=O)c1ccccc1-c1ccc(N2CC[C@@H](NC(=O)Nc3ccc(Cl)cc3)C2=O)c(F)c1F] | 520.1 | Method D, RT = 1.69 min, 99.1% | ¹H NMR (400 MHz, DMSO-d$_6$) δ = 8.88 (s, 1H), 8.15 (dd, J = 7.7, 1.3 Hz, 1H), 7.89-7.71 (m, 2H), 7.52 (dd, J = 7.3, 1.5 Hz, 1H), 7.49-7.37 (m, 3H), 7.36-7.22 (m, 3H), 6.74 (d, J = 7.6 Hz, 1H), 4.62-4.49 (m, 1H), 3.97-3.85 (m, 1H), 3.84-3.73 (m, 1H), 3.06 (s, 3H), 2.60-2.54 (m, 1H), 2.19-2.07 (m, 1H). |
| 11 | 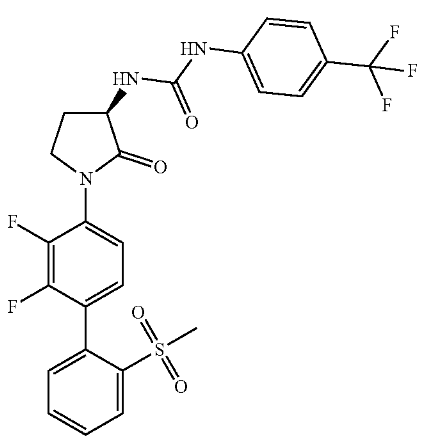 [SMILES: CS(=O)(=O)c1ccccc1-c1ccc(N2CC[C@@H](NC(=O)Nc3ccc(C(F)(F)F)cc3)C2=O)c(F)c1F] | 554.2 | Method D, RT = 1.81 min, 97.1% | ¹H NMR (400 MHz, DMSO-d$_6$) δ = 9.18 (s, 1H), 8.15 (dd, J = 7.8, 1.5 Hz, 1H), 7.90-7.72 (m, 2H), 7.70-7.55 (m, 4H), 7.52 (dd, J = 7.5, 1.3 Hz, 1H), 7.42 (t, J = 7.6 Hz, 1H), 7.36-7.25 (m, 1H), 6.86 (d, J = 7.3 Hz, 1H), 4.65-4.50 (m, 1H), 4.00-3.86 (m, 1H), 3.81-3.77 (m, 1H), 3.06 (s, 3H), 2.62-2.54 (m, 1H), 2.16-2.11 (m, 1H). |

-continued
| Ex | Structure | LCMS (M + H)+ | HPLC Method, RT (min.) & Purity | ¹H NMR |
|---|---|---|---|---|
| 12 | 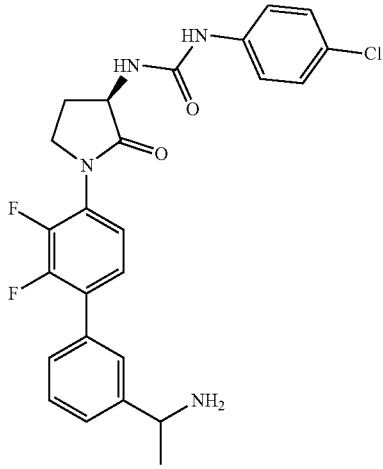 [SMILES: CC(N)c1cccc(-c2ccc(N3CC[C@@H](NC(=O)Nc4ccc(Cl)cc4)C3=O)c(F)c2F)c1] | 485.2 | Method D, RT = 1.50 min, 96.9% | ¹H NMR (400 MHz, DMSO-d$_6$) δ = 8.94 (s, 1H), 7.62 (s, 1H), 7.49-7.34 (m, 7H), 7.31-7.23 (m, 2H), 6.81 (d, J = 7.3 Hz, 1H), 4.61-4.50 (m, 1H), 4.16 (q, J = 6.8 Hz, 1H), 3.92-3.84 (m, 1H), 3.79-3.74 (m, 1H), 3.60-3.20 (m, 2H), 2.61-2.54 (m, 1H), 2.17-2.07 (m, 1H), 1.35 (d, J = 6.6 Hz, 3H). |
| 13 | 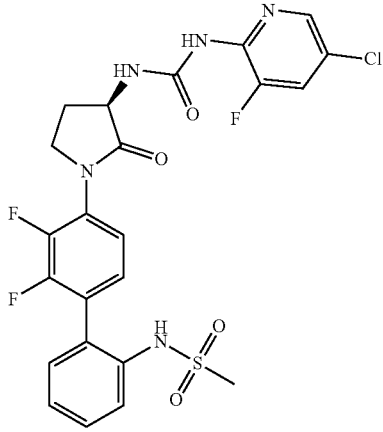 [SMILES: CS(=O)(=O)Nc1ccccc1-c1ccc(N2CC[C@@H](NC(=O)Nc3ncc(Cl)cc3F)C2=O)c(F)c1F] | 554.1 | Method D, RT = 1.67 min, 100% | ¹H NMR (400 MHz, DMSO-d$_6$) δ = 9.40 (s, 1H), 9.15 (s, 1H), 8.77 (d, J = 7.1 Hz, 1H), 8.17 (d, J = 2.2 Hz, 1H), 7.98 (dd, J = 10.3, 2.2 Hz, 1H), 7.52-7.42 (m, 2H), 7.41-7.27 (m, 3H), 7.20 (t, J = 7.1 Hz, 1H), 4.68-4.55 (m, 1H), 3.95-3.81 (m, 2H), 2.86 (s, 3H), 2.60-2.55 (m, 1H), 2.28-2.14 (m, 1H). |
| 14 | 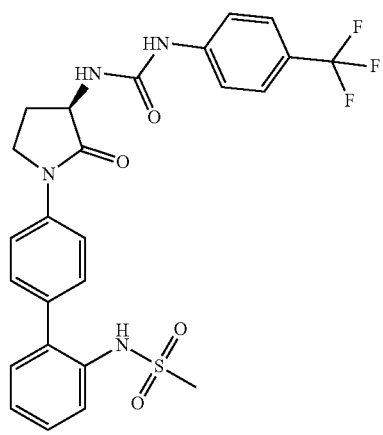 [SMILES: CS(=O)(=O)Nc1ccccc1-c1ccc(N2CC[C@@H](NC(=O)Nc3ccc(C(F)(F)F)cc3)C2=O)cc1] | 533.2 | Method C, RT = 2.07 min, 99.2% | ¹H NMR (400 MHz, DMSO-d$_6$) δ = 9.19 (s, 1H), 8.96 (br. s., 1H), 7.75 (d, J = 8.8 Hz, 2H), 7.65-7.56 (m, 4H), 7.45 (d, J = 8.8 Hz, 2H), 7.41-7.27 (m, 4H), 6.81 (d, J = 7.6 Hz, 1H), 4.58-4.49 (m, 1H), 3.89-3.79 (m, 2H), 2.73 (s, 3H), 2.51-2.50 (m, 1H), 2.10-2.01 (m, 1H). |

-continued

| Ex | Structure | LCMS (M + H)+ | HPLC Method, RT (min.) & Purity | $^1$H NMR |
|---|---|---|---|---|
| 15 | 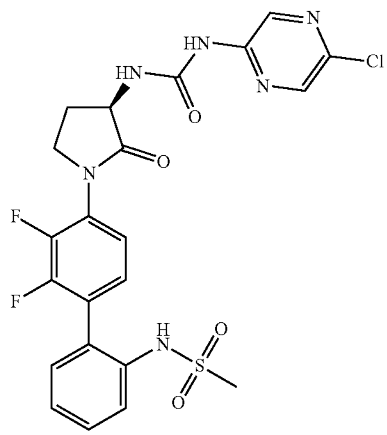 [SMILES: CS(=O)(=O)Nc1ccccc1-c1ccc(N2CC[C@@H](NC(=O)Nc3cnc(Cl)cn3)C2=O)c(F)c1F] | 537.2 | Method D, RT = 1.54 min, 99.7% | $^1$H NMR (400 MHz, DMSO-d$_6$) δ = 9.71 (s, 1H), 9.13 (s, 1H), 8.83 (s, 1H), 8.38 (s, 1H), 7.55 (d, J = 7.6 Hz, 1H), 7.51-7.45 (m, 2H), 7.41-7.31 (m, 3H), 7.24-7.17 (m, 1H), 4.58-4.49 (m, 1H), 3.89-3.79 (m, 2H), 2.88 (s, 3H), 2.51-2.50 (m, 1H), 2.20-2.10 (m, 1H). |
| 16 | 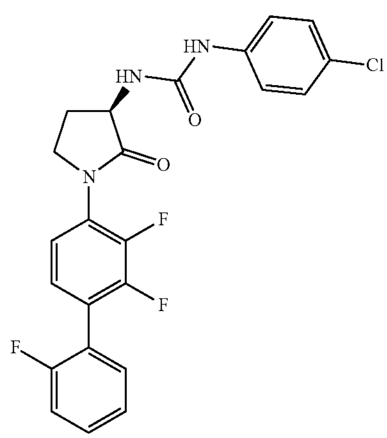 [SMILES: O=C(Nc1ccc(Cl)cc1)N[C@@H]1CCN(c2ccc(-c3ccccc3F)c(F)c2F)C1=O] | 460.1 | Method D, RT = 2.00 min, 92.1% | $^1$H NMR (400 MHz, DMSO-d$_6$) δ = 8.88 (s, 1H), 7.62-7.50 (m, 2H), 7.50-7.42 (m, 3H), 7.42-7.33 (m, 3H), 7.33-7.22 (m, 2H), 6.75 (d, J = 7.3 Hz, 1H), 4.65-4.49 (m, 1H), 3.97-3.84 (m, 1H), 3.84-3.70 (m, 1H), 2.61-2.53 (m, 1H), 2.21-2.04 (m, 1H). |
| 17 | 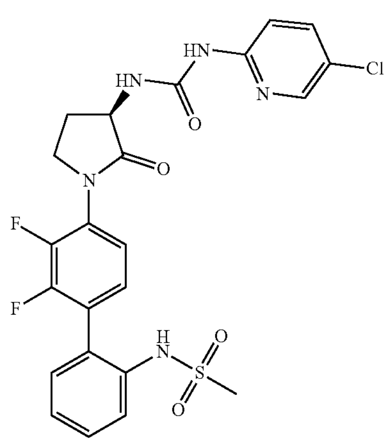 [SMILES: CS(=O)(=O)Nc1ccccc1-c1ccc(N2CC[C@@H](NC(=O)Nc3ccc(Cl)cn3)C2=O)c(F)c1F] | 536.1 | Method D, RT = 1.66 min, 99.7% | $^1$H NMR (400 MHz, DMSO-d$_6$) δ = 9.43 (s, 1H), 9.15 (br. s., 1H), 8.23 (d, J = 2.7 Hz, 1H), 8.05 (d, J = 7.8 Hz, 1H), 7.80 (dd, J = 8.8, 2.7 Hz, 1H), 7.57 (d, J = 8.8 Hz, 1H), 7.50-7.44 (m, 2H), 7.40-7.27 (m, 3H), 7.20 (t, J = 7.1 Hz, 1H), 4.63-4.54 (m, 1H), 3.95-3.81 (m, 2H), 2.86 (s, 3H), 2.60-2.55 (m, 1H), 2.21-2.11 (m, 1H). |

| Ex | Structure | LCMS (M + H)+ | HPLC Method, RT (min.) & Purity | $^1$H NMR |
|---|---|---|---|---|
| 18 | 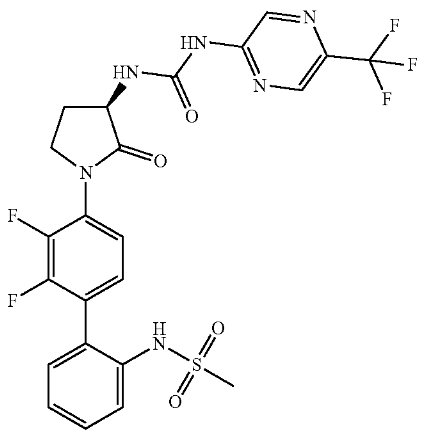 [SMILES: CS(=O)(=O)Nc1ccccc1-c1ccc(N2CC[C@@H](NC(=O)Nc3cnc(C(F)(F)F)cn3)C2=O)c(F)c1F] | 571.2 | Method D, RT = 1.68 min, 100% | $^1$H NMR (400 MHz, DMSO-$d_6$) δ = 10.13 (s, 1H), 9.12 (br. s., 1H), 9.05 (s, 1H), 8.73 (s, 1H), 7.89 (d, J = 7.6 Hz, 1H), 7.52-7.46 (m, 2H), 7.41-7.31 (m, 3H), 7.25-7.16 (m, 1H), 4.66-4.60 (m, 1H), 3.95-3.81 (m, 2H), 2.60-2.55 (m, 1H), 2.88 (s, 3H), 2.24-2.13 (m, 1H). |
| 19 | 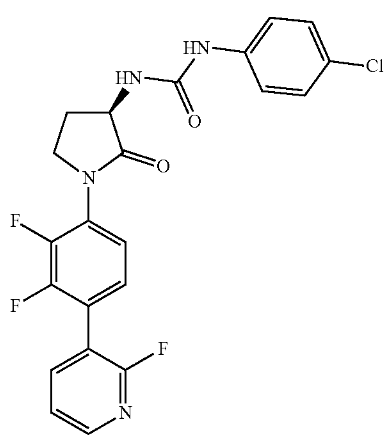 [SMILES: O=C(Nc1ccc(Cl)cc1)N[C@@H]1CCN(c2ccc(-c3cccnc3F)c(F)c2F)C1=O] | 461.1 | Method D, RT = 1.73 min, 96.8% | $^1$H NMR (400 MHz, DMSO-$d_6$) δ = 8.88 (s, 1H), 8.38 (d, J = 4.6 Hz, 1H), 8.16 (t, J = 7.9 Hz, 1H), 7.56 (t, J = 6.2 Hz, 1H), 7.53-7.35 (m, 4H), 7.30 (d, J = 9.0 Hz, 2H), 6.74 (d, J = 7.3 Hz, 1H), 4.64-4.49 (m, 1H), 3.96-3.85 (m, 1H), 3.84-3.73 (m, 1H), 2.61-2.54 (m, 1H), 2.21-2.01 (m, 1H). |
| 20 | 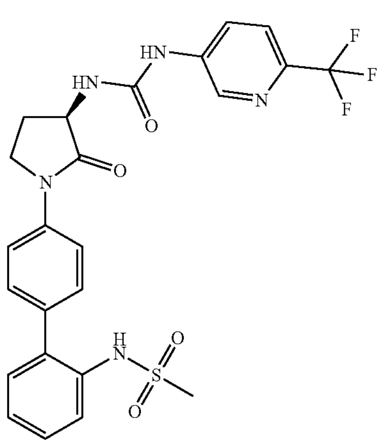 [SMILES: CS(=O)(=O)Nc1ccccc1-c1ccc(N2CC[C@@H](NC(=O)Nc3ccc(C(F)(F)F)nc3)C2=O)cc1] | 534.2 | Method D, RT = 1.63 min, 98.8% | $^1$H NMR (400 MHz, DMSO-$d_6$) δ = 9.43 (s, 1H), 8.95 (s, 1H), 8.71 (d, J = 2.2 Hz, 1H), 8.19 (dd, J = 8.7, 1.8 Hz, 1H), 7.88-7.71 (m, 3H), 7.52 (d, J = 8.8 Hz, 2H), 7.47-7.28 (m, 4H), 6.99 (d, J = 7.3 Hz, 1H), 4.64-4.54 (m, 1H), 3.99-3.78 (m, 2H), 2.74 (s, 3H), 2.50-2.46 (m, 1H) 2.15-2.02 (m, 1H). |

-continued

| Ex | Structure | LCMS (M + H)+ | HPLC Method, RT (min.) & Purity | ¹H NMR |
|---|---|---|---|---|
| 21 | 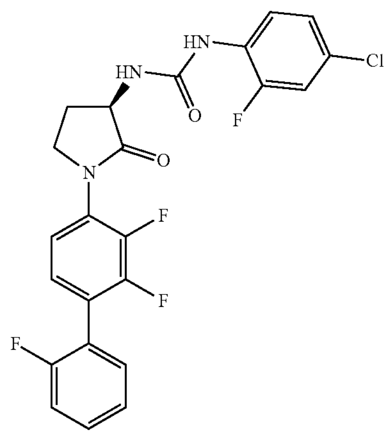 [SMILES: O=C(Nc1ccc(Cl)cc1F)N[C@@H]1CCN(c2ccc(-c3ccccc3F)c(F)c2F)C1=O] | 478.1 | Method D, RT = 2.05 min, 100% | ¹H NMR (400 MHz, DMSO-d$_6$) δ = 8.65 (d, J = 2.2 Hz, 1H), 8.16 (t, J = 8.9 Hz, 1H), 7.61-7.05 (m, 2H), 7.50-7.32 (m, 5H), 7.27-7.14 (m, 2H), 4.64-4.50 (m, 1H), 3.98-3.85 (m, 1H), 3.84-3.75 (m, 1H), 2.64-2.55 (m, 1H), 2.17-2.01 (m, 1H). |
| 22 | 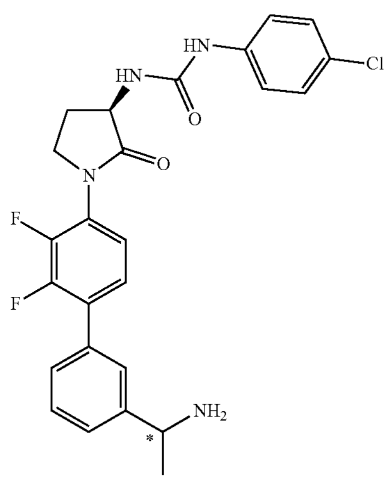 [SMILES: CC(N)c1cccc(-c2ccc(N3CC[C@@H](NC(=O)Nc4ccc(Cl)cc4)C3=O)c(F)c2F)c1] | 485.2 | Method D, RT = 1.55 min, 100% | ¹H NMR (400 MHz, DMSO-d$_6$) δ = 8.97 (s, 1H), 7.61 (s, 1H), 7.53-7.33 (m, 7H), 7.33-7.22 (m, 2H), 6.84 (d, J = 7.3 Hz, 1H), 4.55 (m, 1H), 4.14 (q, J = 6.8 Hz, 1H), 3.91-3.84 (m, 1H), 3.78-3.73 (m, 1H), 2.64-2.55 (m, 1H), 2.12 (m, 1H), 1.34 (d, J = 6.6 Hz, 3H). |
| 23 | 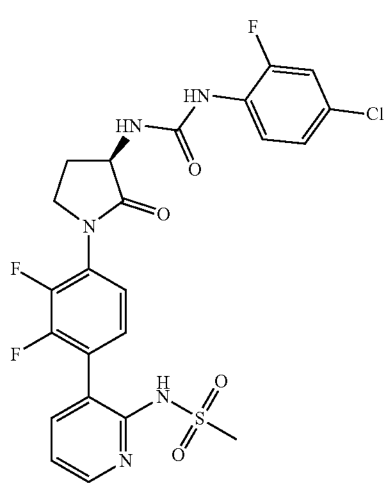 [SMILES: CS(=O)(=O)Nc1ncccc1-c1ccc(N2CC[C@@H](NC(=O)Nc3ccc(Cl)cc3F)C2=O)c(F)c1F] | 554.2 | Method D, RT = 1.46 min, 94.8% | ¹H NMR (400 MHz, DMSO-d$_6$) δ = 8.83 (br. s., 1H), 8.63 (br. s., 1H), 8.16 (t, J = 8.9 Hz, 1H), 8.08 (br. s., 1H), 7.47-7.32 (m, 2H), 7.32-7.10 (m, 4H), 6.65 (br. s., 1H), 4.64-4.48 (m, 1H), 3.92-3.82 (m, 1H), 3.75 (t, J = 8.7 Hz, 1H), 2.95 (br. s., 3H), 2.63-2.54 (m, 1H), 2.21-1.96 (m, 1H). |

-continued
| Ex | Structure | LCMS (M + H)+ | HPLC Method, RT (min.) & Purity | ¹H NMR |
|---|---|---|---|---|
| 24 | 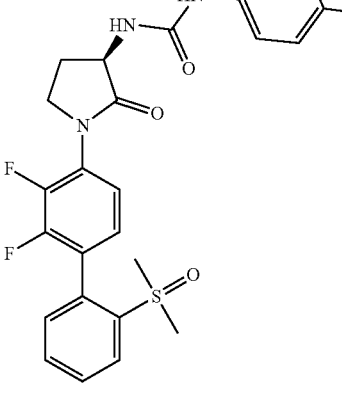 | 521.1 | Method D, RT = 1.62 min, 99.7% | 1H NMR (400 MHz, DMSO-d$_6$) δ 9.47 (s, 1H), 8.25 (d, J = 2.7 Hz, 1H), 8.15 (d, J = 7.6 Hz, 1H), 8.01-7.89 (m, 1H), 7.88-7.72 (m, 3H), 7.65 (d, J = 9.3 Hz, 1H), 7.55-7.46 (m, 1H), 7.43 (t, J = 7.2 Hz, 1H), 7.31 (t, J = 7.0 Hz, 1H), 4.67-4.56 (m, 1H), 3.97-3.87 (m, 1H), 3.85-3.77 (m, 1H), 3.06 (s, 3H), 2.63-2.55 (m, 1H), 2.20-2.10 (m, 1H). |
| 25 | 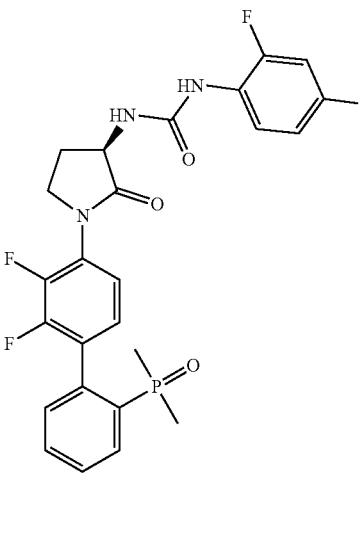 | 536.2 | Method D, RT = 1.476 min, 98.6% | ¹H NMR (400 MHz, DMSO-d$_6$) δ = 8.64 (br. s., 1H), 8.16 (t, J = 9.0 Hz, 1H), 7.97-7.84 (m, 1H), 7.69-7.57 (m, 2H), 7.43 (dd, J = 11.0, 2.5 Hz, 1H), 7.40-7.32 (m, 2H), 7.32-7.23 (m, 1H), 7.23-7.12 (m, 2H), 4.56 (dt, J = 9.9, 8.1 Hz, 1H), 3.95-3.85 (m, 1H), 3.78 (br. t., J = 8.8 Hz, 1H), 2.63-2.54 (m, 1H), 2.14-1.99 (m, 1H), 1.52 (br. d., J = 13.1 Hz, 6H). |
| 26 | 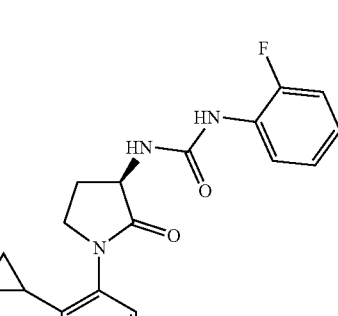 | 557.2 | Method D, RT = 1.89 min, 99.7% | ¹H NMR (400 MHz, DMSO-d$_6$) δ = 8.95 (br. s., 1H), 8.63 (d, J = 2.2 Hz, 1H), 8.17 (t, J = 8.9 Hz, 1H), 7.52-7.24 (m, 7H), 7.23-7.13 (m, 2H), 7.12 (s, 1H), 4.63-4.47 (m, 1H), 3.82 (td, J = 9.5, 6.5 Hz, 1H), 3.71-3.59 (m, 1H), 2.86 (s, 3H), 2.63-2.56 (m, 1H), 2.17-2.04 (m, 1H), 2.01-1.95 (m, 1H), 1.04-0.83 (m, 2H), 0.80-0.58 (m, 2H). |

-continued

| Ex | Structure | LCMS (M + H)+ | HPLC Method, RT (min.) & Purity | ¹H NMR |
|---|---|---|---|---|
| 27 | 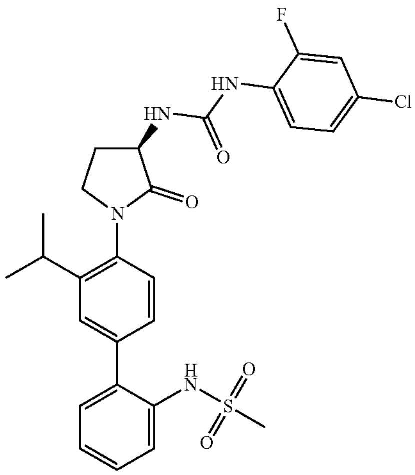 [SMILES: CC(C)c1cc(-c2ccccc2NS(C)(=O)=O)ccc1N1CC[C@@H](NC(=O)Nc2ccc(Cl)cc2F)C1=O] | 559.2 | Method D, RT = 1.868 min, 99.6% | ¹H NMR (400 MHz, DMSO-$d_6$) δ = 9.01 (s, 1H), 8.62 (d, J = 2.0 Hz, 1H), 8.17 (t, J = 8.9 Hz, 1H), 7.55 (d, J = 2.0 Hz, 1H), 7.48-7.32 (m, 6H), 7.32-7.26 (m, 1H), 7.25-7.12 (m, 2H), 4.60-4.50 (m, 1H), 3.82-3.71 (m, 1H), 3.56 (t, J = 9.3 Hz, 1H), 3.06-3.02 (m, 1H) 2.81 (s, 3H), 2.65-2.56 (m, 1H), 2.12-2.02 (m, 1H), 1.31-1.13 (m, 6H). |
| 28 | 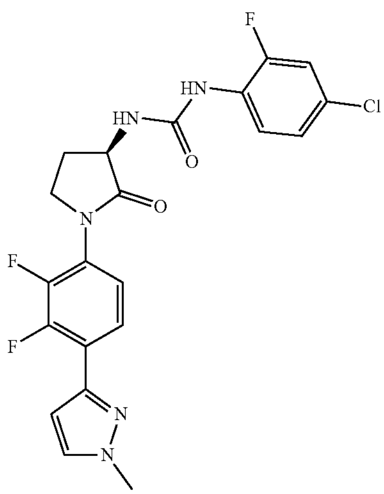 [SMILES: Cn1ccc(-c2ccc(N3CC[C@@H](NC(=O)Nc4ccc(Cl)cc4F)C3=O)c(F)c2F)n1] | 464.1 | Method D, RT = 1.732 min, 98.6% | ¹H NMR (400 MHz, DMSO-$d_6$) δ = 8.62 (d, J = 2.2 Hz, 1H), 8.15 (t, J = 8.9 Hz, 1H), 7.84 (d, J = 2.4 Hz, 1H), 7.80-7.68 (m, 1H), 7.49-7.28 (m, 2H), 7.24-7.06 (m, 2H), 6.73-6.61 (m, 1H), 4.63-4.46 (m, 1H), 3.94 (s, 3H), 3.91-3.78 (m, 1H), 3.78-3.67 (m, 1H), 2.64-2.53 (m, 1H), 2.16-2.01 (m, 1H). |
| 29 | 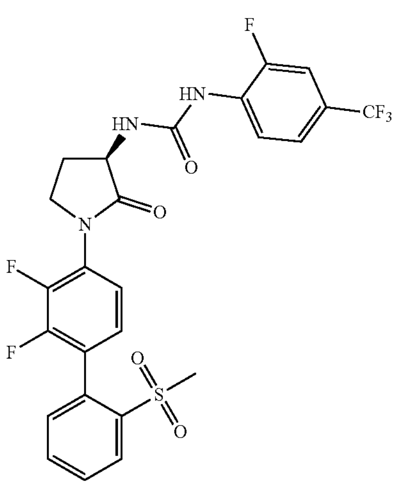 [SMILES: CS(=O)(=O)c1ccccc1-c1ccc(N2CC[C@@H](NC(=O)Nc3ccc(C(F)(F)F)cc3F)C2=O)c(F)c1F] | 572.2 | Method C, RT = 1.887 min, 100% | ¹H NMR (400 MHz, DMSO-$d_6$) δ = 8.93 (s, 1H), 8.41 (t, J = 8.4 Hz, 1H), 8.15 (dd, J = 7.9, 1.3 Hz, 1H), 7.90-7.72 (m, 2H), 7.66 (dd, J = 11.5, 1.7 Hz, 1H), 7.51 (dd, J = 7.5, 1.3 Hz, 2H), 7.46-7.37 (m, 1H), 7.37-7.21 (m, 2H), 4.65-4.51 (m, 1H), 4.00-3.87 (m, 1H), 3.81 (t, J = 8.8 Hz, 1H), 3.06 (s, 3H), 2.65-2.56 (m, 1H), 2.20-2.02 (m, 1H). |

-continued

| Ex | Structure | LCMS (M + H)+ | HPLC Method, RT (min.) & Purity | ¹H NMR |
|---|---|---|---|---|
| 30 | 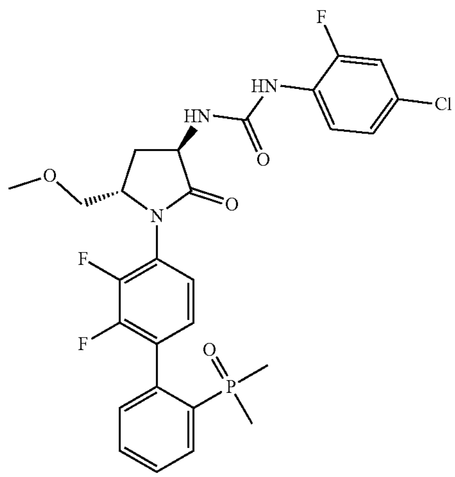 [SMILES: COC[C@@H]1C[C@@H](NC(=O)Nc2ccc(Cl)cc2F)C(=O)N1c1ccc(-c2ccccc2P(C)(C)=O)c(F)c1F] | 580.1 | Method C, RT = 1.632 min, 98.7% | ¹H NMR (400 MHz, DMSO-$d_6$) δ = 8.65 (s, 1H), 8.14 (t, J = 8.8 Hz, 1H), 8.01-7.87 (m, 1H), 7.72-7.57 (m, 2H), 7.48-7.36 (m, 2H), 7.29 (m, 2H), 7.23-7.16 (m, 1H), 7.10 (d, J = 7.6 Hz, 1H), 4.70-4.58 (m, 1H), 4.39-4.27 (m, 1H), 3.51-3.43 (m, 1H), 3.39-3.35 (m, 1H), 3.24 (s, 3H), 2.46-2.44 (m, 1H), 2.34-2.26 (m, 1H), 1.61-1.40 (m, 6H) |
| 31 | 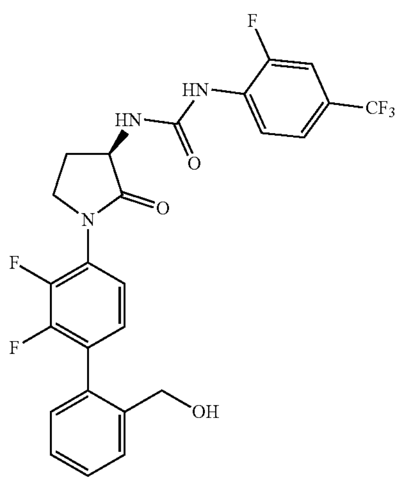 [SMILES: O=C(Nc1ccc(C(F)(F)F)cc1F)N[C@@H]1CCN(c2ccc(-c3ccccc3CO)c(F)c2F)C1=O] | 524.2 | Method D, RT = 1.719 min, 99.2% | ¹H NMR (400 MHz, DMSO-$d_6$) δ = 8.93 (d, J = 2.4 Hz, 1H), 8.41 (t, J = 8.2 Hz, 1H), 7.72-7.58 (m, 2H), 7.55-7.31 (m, 5H), 7.30-7.17 (m, 2H), 5.16 (t, J = 5.5 Hz, 1H), 4.64-4.53 (m, 1H), 4.35 (d, J = 5.6 Hz, 2H), 3.97-3.84 (m, 1H), 3.80 (t, J = 8.7 Hz, 1H), 2.61 (dd, J = 19.4, 6.7 Hz, 1H), 2.15-2.03 (m, 1H). |
| 32 | 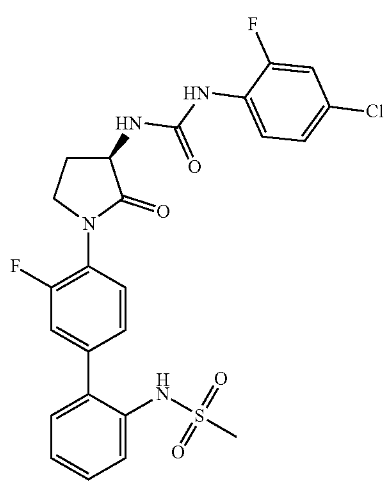 [SMILES: CS(=O)(=O)Nc1ccccc1-c1ccc(N2CC[C@@H](NC(=O)Nc3ccc(Cl)cc3F)C2=O)c(F)c1] | 535.2 | Method C, RT = 1.550 min, 100% | ¹H NMR (400 MHz, DMSO-$d_6$) δ = 9.11 (br. s., 1H), 8.63 (d, J = 2.4 Hz, 1H), 8.16 (t, J = 8.9 Hz, 1H), 7.56 (t, J = 8.2 Hz, 1H), 7.50-7.28 (m, 7H), 7.24-7.12 (m, 2H), 4.60-4.50 (m, 1H), 3.92-3.82 (m, 1H), 3.74 (t, J = 8.4 Hz, 1H), 2.86 (s, 3H), 2.60 (dd, J = 12.0, 8.1 Hz, 1H), 2.14-2.03 (m, 1H). |

| Ex | Structure | LCMS (M + H)+ | HPLC Method, RT (min.) & Purity | ¹H NMR |
|---|---|---|---|---|
| 33 | 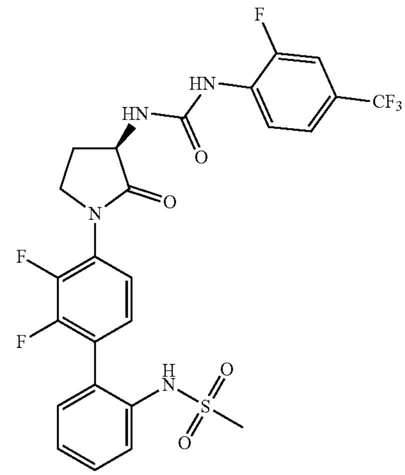 [SMILES: CS(=O)(=O)Nc1ccccc1-c1ccc(N2CC[C@@H](NC(=O)Nc3ccc(C(F)(F)F)cc3F)C2=O)c(F)c1F] | 587.2 | Method C, RT = 1.726 min, 98.1% | ¹H NMR (400 MHz, DMSO-d$_6$) δ = 9.12 (br. s., 1H), 8.93 (d, J = 2.9 Hz, 1H), 8.41 (t, J = 8.3 Hz, 1H), 7.66 (d, J = 11.7 Hz, 1H), 7.56-7.43 (m, 3H), 7.43-7.27 (m, 4H), 7.23 (t, J = 7.1 Hz, 1H), 4.66-4.54 (m, 1H), 4.00-3.86 (m, 1H), 3.78 (t, J = 9.2 Hz, 1H), 2.91 (s, 3H), 2.66-2.57 (m, 1H), 2.16-2.04 (m, 1H). |
| 34 | 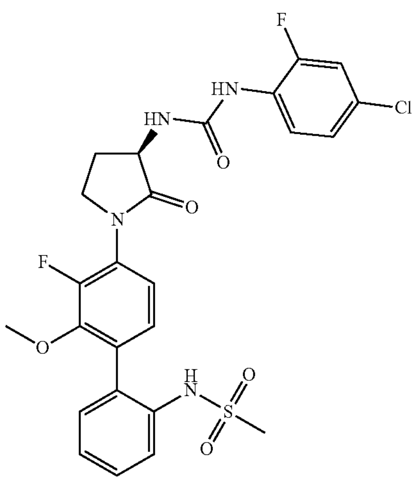 [SMILES: COc1c(-c2ccccc2NS(C)(=O)=O)ccc(N2CC[C@@H](NC(=O)Nc3ccc(Cl)cc3F)C2=O)c1F] | 565.2 | Method C, RT = 1.606 min, 96.7% | ¹H NMR (400 MHz, DMSO-d$_6$) δ = 8.78 (s, 1H), 8.63 (d, J = 2.7 Hz, 1H), 8.16 (t, J = 8.9 Hz, 1H), 7.53-7.46 (m, 1H), 7.46-7.36 (m, 2H), 7.34-7.15 (m, 5H), 7.11 (dd, J = 8.4, 1.6 Hz, 1H), 4.60-4.49 (m, 1H), 3.94-3.80 (m, 1H), 3.74-3.72 (m, 1H), 3.66 (s, 3H), 2.90 (s, 3H), 2.63-2.54 (m, 1H), 2.12-2.01 (m, 1H). |
| 35 | 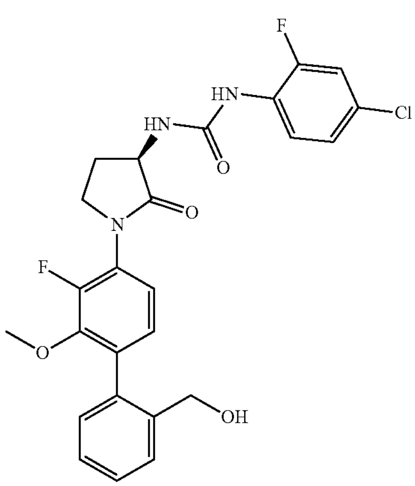 [SMILES: COc1c(-c2ccccc2CO)ccc(N2CC[C@@H](NC(=O)Nc3ccc(Cl)cc3F)C2=O)c1F] | 502.1 | Method D, RT = 1.634 min, 93.3% | ¹H NMR (400 MHz, DMSO-d$_6$) δ = 8.63 (d, J = 2.2 Hz, 1H), 8.21-8.10 (m, 1H), 7.59 (d, J = 7.1 Hz, 1H), 7.50-7.55 (m, 2H), 7.33 (t, J = 8.1 Hz, 1H), 7.28-7.12 (m, 4H), 7.06 (dd, J = 8.1, 1.7 Hz, 1H), 5.06 (t, J = 5.5 Hz, 1H), 4.59-4.48 (m, 1H), 4.33-4.29 (m, 2H), 3.94-3.81 (m, 1H), 3.75 (t, J = 8.8 Hz, 1H), 3.55 (s, 3H), 2.59 (dd, J = 12.2, 7.3 Hz, 1H), 2.14-1.98 (m, 1H). |

-continued

| Ex | Structure | LCMS (M + H)+ | HPLC Method, RT (min.) & Purity | ¹H NMR |
|---|---|---|---|---|
| 36 | 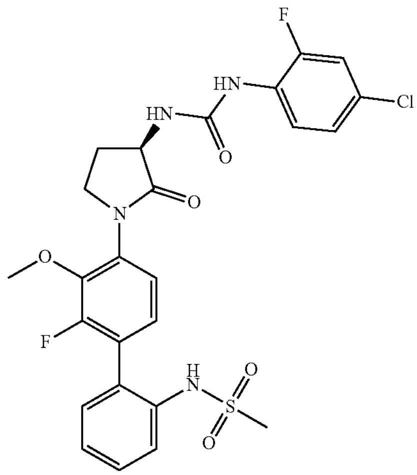 [SMILES: COc1c(N2CC[C@@H](NC(=O)Nc3ccc(Cl)cc3F)C2=O)ccc(-c2ccccc2NS(C)(=O)=O)c1F] | 565.1 | Method D, RT = 1.669 min, 100% | ¹H NMR (400 MHz, DMSO-d$_6$) δ = 8.68 (s, 1H), 8.37 (s, 1H), 8.16 (t, J = 8.9 Hz, 1H), 7.56-7.37 (m, 3H), 7.35-7.15 (m, 5H), 7.15-7.05 (m, 1H), 4.59-4.49 (m, 1H), 3.87 (s, 3H), 3.79 (dd, J = 9.7, 6.5 Hz, 1H), 3.69 (t, J = 8.6 Hz, 1H), 2.88 (s, 3H), 2.59 (dd, J = 11.7, 7.3 Hz, 1H), 2.13-1.96 (m, 1H). |
| 37 | 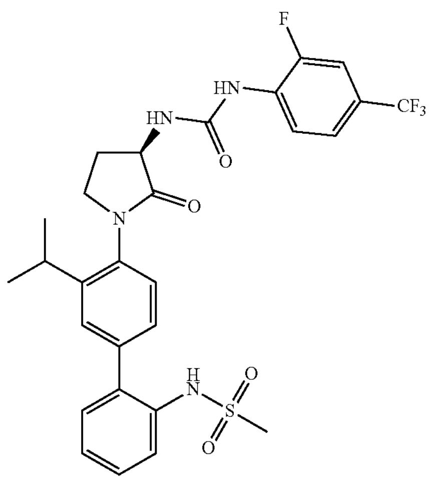 [SMILES: CC(C)c1cc(-c2ccccc2NS(C)(=O)=O)ccc1N1CC[C@@H](NC(=O)Nc2ccc(C(F)(F)F)cc2F)C1=O] | 593.2 | Method C, RT = 1.902 min, 97.5% | ¹H NMR (400 MHz, DMSO-d$_6$) δ = 8.97 (br. s., 1H), 8.49-8.30 (m, 2H), 7.65 (d, J = 11.7 Hz, 1H), 7.55 (d, J = 2.0 Hz, 1H), 7.52 (d, J = 9.0 Hz, 1H), 7.48-7.22 (m, 7H), 4.59-4.52 (m, 1H), 3.83-3.77 (m, 1H), 3.57-3.55 (m, 1H), 3.06-3.02 (m, 1H), 2.87 (s, 3H), 2.66-2.58 (m, 1H), 2.14-2.01 (m, 1H), 1.31-1.13 (m, 6H). |
| 38 | 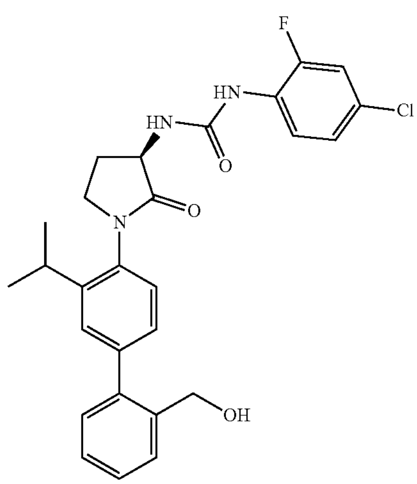 [SMILES: CC(C)c1cc(-c2ccccc2CO)ccc1N1CC[C@@H](NC(=O)Nc2ccc(Cl)cc2F)C1=O] | 496.2 | Method C, RT = 1.863 min, 92.2% | ¹H NMR (400 MHz, DMSO-d$_6$) δ = 8.67 (s, 1H), 8.38 (s, 1H), 8.17 (m, 1H), 7.59 (d, J = 7.3 Hz, 1H), 7.49-7.30 (m, 4H), 7.30-7.11 (m, 4H), 4.61-4.50 (m, 1H), 4.43 (s, 2H), 3.91 (s, 1H), 3.81-3.76 (m, 1H), 3.59-3.56 (m, 1H), 3.04-3.01 (m, 1H), 2.64-2.55 (m, 1H), 2.14-2.03 (m, 1H), 1.31-1.13 (m, 6H). |

| Ex | Structure | LCMS (M + H)+ | HPLC Method, RT (min.) & Purity | ¹H NMR |
|---|---|---|---|---|
| 39 | 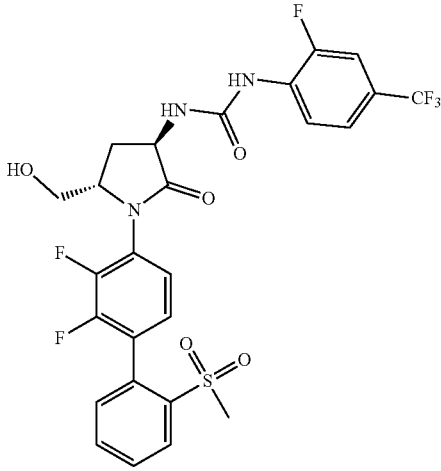 [SMILES: CS(=O)(=O)c1ccccc1-c1ccc(N2C(=O)[C@H](NC(=O)Nc3ccc(C(F)(F)F)cc3F)C[C@H]2CO)c(F)c1F] | 602.1 | Method C, RT = 1.731 min, 92.6% | ¹H NMR (400 MHz, DMSO-d$_6$) δ = 8.92 (br. s., 1H), 8.41 (t, J = 8.4 Hz, 1H), 8.15 (d, J = 7.8 Hz, 1H), 7.91-7.76 (m, 2H), 7.66 (br. d., J = 12.0 Hz, 1H), 7.57-7.47 (m, 2H), 7.43-7.29 (m, 2H), 7.25 (br. d., J = 6.8 Hz, 1H), 5.13 (br. s., J = 1.7 Hz, 1H), 4.78-4.65 (m, 1H), 4.27-4.13 (m, 1H), 3.54-3.42 (m, 2H), 3.06 (s, 3H), 2.57-2.24 (m, 1H), 2.35-2.31 (m, 1H). |
| 40 | 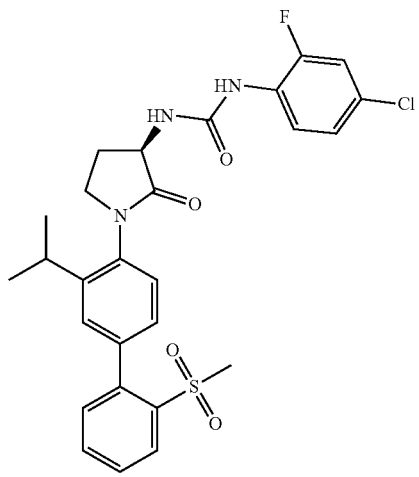 [SMILES: CC(C)c1cc(-c2ccccc2S(C)(=O)=O)ccc1N1CC[C@@H](NC(=O)Nc2ccc(Cl)cc2F)C1=O] | 544.2 | Method D, RT = 1.851 min, 100% | ¹H NMR (400 MHz, DMSO-d$_6$) δ = 8.63 (d, J = 2.0 Hz, 1H), 8.17 (t, J = 8.9 Hz, 1H), 8.12 (dd, J = 7.9, 1.1 Hz, 1H), 7.82-7.75 (m, 1H), 7.73-7.64 (m, 1H), 7.54-7.36 (m, 3H), 7.34-7.25 (m, 2H), 7.23-7.09 (m, 2H), 4.57-4.52 (m, 1H), 3.84-3.74 (m, 1H), 3.59 (t, J = 9.0 Hz, 1H), 3.06-3.02 (m, 1H), 2.82 (s, 3H), 2.65-2.56 (m, 1H), 2.13-2.00 (m, 1H), 1.31-1.06 (m, 6H). |
| 41 | 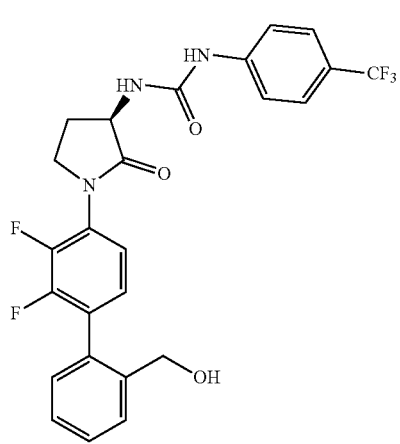 [SMILES: O=C(Nc1ccc(C(F)(F)F)cc1)N[C@@H]1CCN(c2ccc(-c3ccccc3CO)c(F)c2F)C1=O] | 506.1 | Method D, RT = 1.825 min, 97.2% | ¹H NMR (400 MHz, DMSO-d$_6$) δ = 9.15 (s, 1H), 7.78-7.50 (m, 5H), 7.50-7.43 (m, 1H), 7.43-7.31 (m, 2H), 7.30-7.16 (m, 2H), 6.85 (d, J = 7.3 Hz, 1H), 5.16 (t, J = 5.4 Hz, 1H), 4.65-4.52 (m, 1H), 4.35 (d, J = 5.4 Hz, 2H), 3.99-3.83 (m, 1H), 3.83-3.72 (m, 1H), 2.64-2.53 (m, 1H), 2.20-2.05 (m, 1H). |

-continued
| Ex | Structure | LCMS (M + H)+ | HPLC Method, RT (min.) & Purity | ¹H NMR |
|---|---|---|---|---|
| 42 | 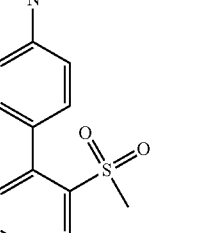 | 568.1 | Method C, RT = 1.598 min, 98.9% | ¹H NMR (400 MHz, DMSO-d$_6$) δ = 8.61 (br. s., 1H), 8.22-8.07 (m, 2H), 7.88-7.73 (m, 2H), 7.58-7.49 (m, 1H), 7.45-7.25 (m, 3H), 7.23-7.15 (m, 1H), 7.09 (d, J = 7.1 Hz, 1H), 4.76-4.64 (m, 1H), 4.24-4.13 (m, 1H), 3.99-3.87 (m, 1H), 3.49-3.45 (m, 2H), 3.05 (s, 3H), 2.57-2.55 (m, 1H), 2.26-2.21 (m, 1H). |
| 43 | 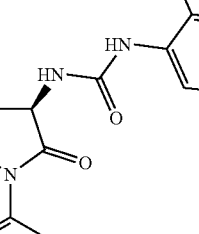 | 591.2 | Method C, RT = 2.008 min, 100% | ¹H NMR (400 MHz, DMSO-d$_6$) δ = 9.08-8.82 (m, 2H), 8.42 (t, J = 8.3 Hz, 1H), 7.71-7.61 (m, 1H), 7.52 (d, J = 8.3 Hz, 1H), 7.48-7.36 (m, 2H), 7.36-7.20 (m, 5H), 7.12 (s, 1H), 4.65-4.52 (m, 1H), 3.83 (td, J = 9.2, 6.1 Hz, 1H), 3.66 (t, J = 9.2 Hz, 1H), 2.86 (s, 3H), 2.67-2.58 (m, 1H), 2.19-2.03 (m, 1H), 2.00-1.90 (m, 1H), 1.04-0.83 (m, 2H), 0.79-0.62 (m, 2H). |
| 44 | 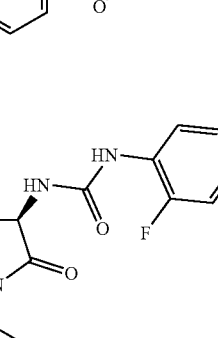 | 545.2 | Method C, RT = 1.776 min, 100% | ¹H NMR (400 MHz, DMSO-d$_6$) δ = 8.63 (s, 1H), 8.33 (d, J = 7.8 Hz, 1H), 8.15 (t, J = 8.9 Hz, 1H), 7.51 (s, 1H), 7.49-7.30 (m, 6H), 7.25-7.15 (m, 2H), 4.98 (m, 1H), 4.61-4.51 (m, 1H), 3.89 (td, J = 9.5, 6.6 Hz, 1H), 3.77 (t, J = 8.7 Hz, 1H), 2.58 (dd, J = 13.6, 5.7 Hz, 1H), 2.16-2.01 (m, 1H), 1.85 (s, 3H), 1.38 (d, J = 7.1 Hz, 3H). |

-continued

| Ex | Structure | LCMS (M + H)+ | HPLC Method, RT (min.) & Purity | ¹H NMR |
|---|---|---|---|---|
| 45 | 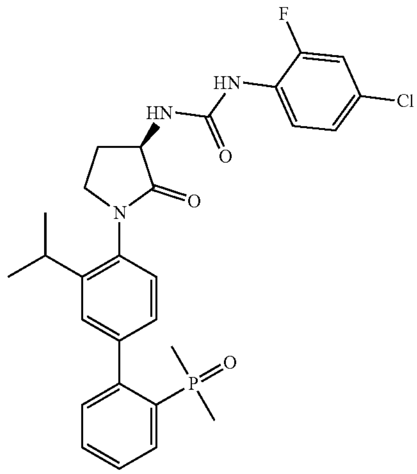 [SMILES: CC(C)c1cc(-c2ccccc2P(C)(C)=O)ccc1N1CC[C@@H](NC(=O)Nc2ccc(Cl)cc2F)C1=O] | 542.2 | Method C, RT = 1.778 min, 100% | ¹H NMR (400 MHz, DMSO-d$_6$) δ = 8.63 (s, 1H), 8.17 (t, J = 8.9 Hz, 1H), 7.98 (dd, J = 12.8, 7.7 Hz, 1H), 7.68-7.59 (m, 1H), 7.59-7.47 (m, 2H), 7.45-7.26 (m, 4H), 7.25-7.13 (m, 2H), 4.60-4.49 (m, 1H), 3.80 (d, J = 6.1 Hz, 1H), 3.61-3.52 (m, 1H), 3.07-2.99 (m, 1H), 2.59-2.55 (m, 1H), 2.28-1.99 (m, 1H), 1.33 (d, J = 13.4 Hz, 6H), 1.23-1.10 (m, 6H). |
| 46 | 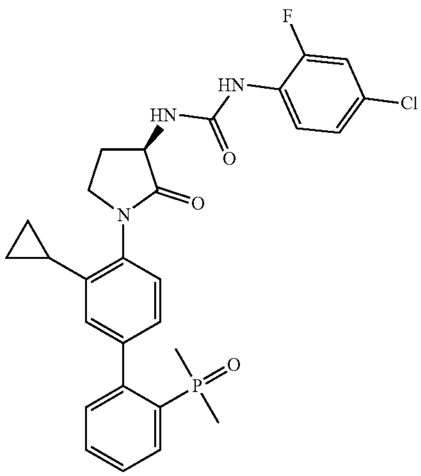 [SMILES: CP(C)(=O)c1ccccc1-c1ccc(N2CC[C@@H](NC(=O)Nc3ccc(Cl)cc3F)C2=O)c(C2CC2)c1] | 577.2 | Method C, RT = 1.716 min, 100% | ¹H NMR (400 MHz, DMSO-d$_6$) δ = 8.64 (d, J = 2.4 Hz, 1H), 8.16 (t, J = 8.9 Hz, 1H), 7.93 (dd, J = 12.3, 8.2 Hz, 1H), 7.61 (t, J = 7.5 Hz, 1H), 7.54 (t, J = 7.5 Hz, 1H), 7.42 (dd, J = 11.2, 2.4 Hz, 1H), 7.39-7.32 (m, 1H), 7.32-7.24 (m, 2H), 7.24-7.06 (m, 3H), 4.63-4.50 (m, 1H), 3.83 (td, J = 9.6, 6.7 Hz, 1H), 3.67 (t, J = 8.8 Hz, 1H), 2.65-2.56 (m, 1H), 2.16-2.05 (m, 1H), 2.00-1.90 (m, 1H), 1.34 (d, J = 13.2 Hz, 3H), 1.33 (d, J = 13.2 Hz, 3H), 0.98-0.84 (m, 2H), 0.82-0.65 (m, 2H). |
| 47 | 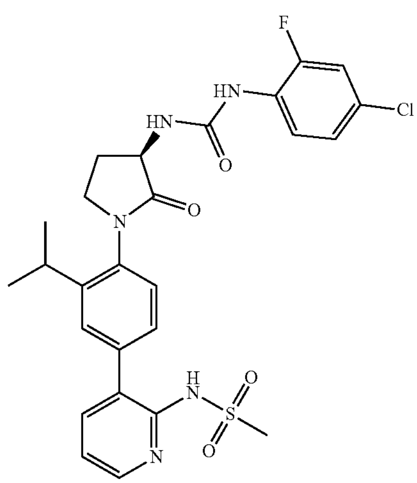 | 560.2 | Method C, RT = 1.760 min, 100% | ¹H NMR (400 MHz, DMSO-d$_6$) δ = 8.80 (br. s., 1H), 8.62 (s, 1H), 8.25-8.05 (m, 2H), 7.68-7.51 (m, 2H), 7.51-7.35 (m, 2H), 7.31-7.10 (m, 3H), 6.93-6.91 (m, 1H), 4.59-4.50 (m, 1H), 3.77 (d, J = 6.4 Hz, 1H), 3.56 (d, J = 8.3 Hz, 1H), 3.10 (s, 3H), 3.04-2.98 (m, 1H), 2.65-2.62 (m, 1H), 2.18-1.96 (m, 1H), 1.39-1.15 (m, 6H). |

-continued
| Ex | Structure | LCMS (M + H)+ | HPLC Method, RT (min.) & Purity | ¹H NMR |
|---|---|---|---|---|
| 48 | 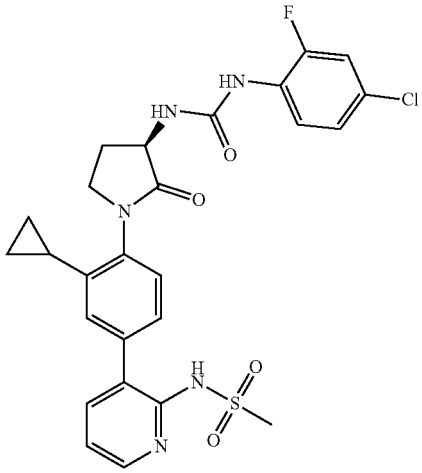 [SMILES: CS(=O)(=O)Nc1ncccc1-c1ccc(N2CC[C@@H](NC(=O)Nc3ccc(Cl)cc3F)C2=O)c(C2CC2)c1] | 558.2 | Method C, RT = 1.861 min, 100% | ¹H NMR (400 MHz, DMSO-d$_6$) δ = 10.5 (br. s., 1H), 8.64 (d, J = 2.7 Hz, 1H), 8.31-8.04 (m, 2H), 7.71 (dd, J = 7.6, 1.7 Hz, 1H), 7.47-7.35 (m, 2H), 7.35-7.27 (m, 1H), 7.26-7.14 (m, 3H), 7.10 (br. s., 1H), 4.64-4.50 (m, 1H), 3.81 (td, J = 9.6, 6.5 Hz, 1H), 3.65 (t, J = 9.0 Hz, 1H), 3.20 (s, 3H), 2.66-2.57 (m, 1H), 2.15-2.02 (m, 1H), 2.01-1.88 (m, 1H), 1.03-0.83 (m, 2H), 0.78-0.55 (m, 2H). |
| 49 | 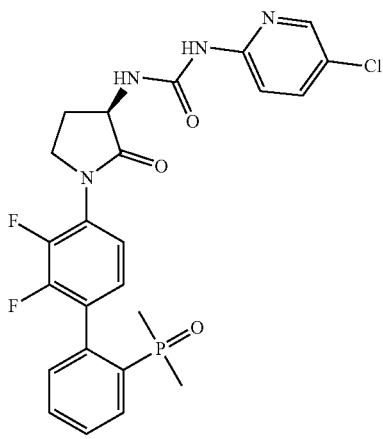 [SMILES: CP(C)(=O)c1ccccc1-c1ccc(N2CC[C@@H](NC(=O)Nc3ccc(Cl)cn3)C2=O)c(F)c1F] | 519.1 | Method C, RT = 1.469 min, 100% | ¹H NMR (400 MHz, DMSO-d$_6$) δ = 9.45 (s, 1H), 8.25 (d, J = 2.7 Hz, 1H), 8.00-7.87 (m, 2H), 7.82 (dd, J = 9.0, 2.7 Hz, 1H), 7.71-7.54 (m, 3H), 7.44-7.31 (m, 2H), 7.31-7.22 (m, 1H), 4.66-4.56 (m, 1H), 4.01-3.85 (m, 1H), 3.84-3.76 (m, 1H), 2.59-2.86 (m, 1H), 2.21-2.11 (m, 1H), 1.52 (d, J = 13.2 Hz, 6H). |
| 50 | 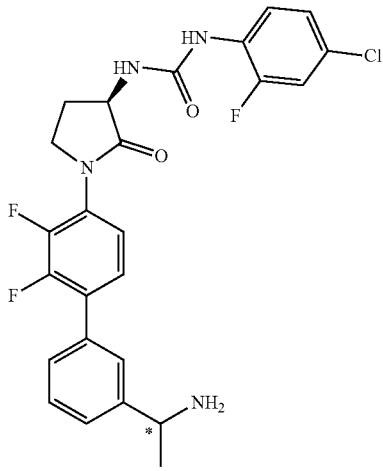 [SMILES: CC(N)c1cccc(-c2ccc(N3CC[C@@H](NC(=O)Nc4ccc(Cl)cc4F)C3=O)c(F)c2F)c1] | 503.2 | Method D, RT = 1.498 min, 100% | ¹H NMR (400 MHz, DMSO-d$_6$) δ = 8.64 (d, J = 1.7 Hz, 1H), 8.20-8.08 (m, 1H), 7.62 (s, 1H), 7.53-7.28 (m, 6H), 7.25-7.16 (m, 2H), 4.62-4.49 (m, 1H), 4.17 (q, J = 6.6 Hz, 1H), 3.94-3.85 (m, 1H), 3.82-3.72 (m, 1H), 3.34 (br. s., 2H), 2.65-2.55 (m, 1H), 2.13-2.02 (m, 1H), 1.35 (d, J = 6.6 Hz, 3H). |

-continued
| Ex | Structure | LCMS (M + H)+ | HPLC Method, RT (min.) & Purity | ¹H NMR |
|---|---|---|---|---|
| 51 | 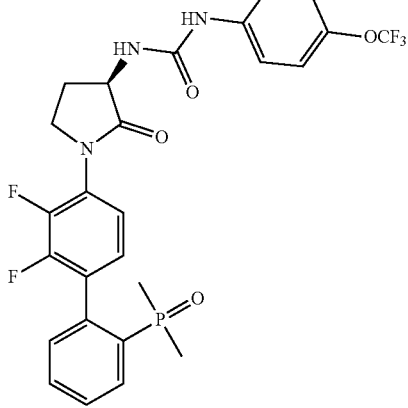 | 568.2 | Method C, RT = 1.709 min, 100% | ¹H NMR (400 MHz, DMSO-$d_6$) δ = 8.99 (s, 1H), 7.99-7.86 (m, 1H), 7.73-7.57 (m, 2H), 7.57-7.44 (m, 2H), 7.42-7.32 (m, 2H), 7.32-7.14 (m, 3H), 6.81 (d, J = 7.3 Hz, 1H), 4.61-4.49 (m, 1H), 3.94-3.84 (m, 1H), 3.83-3.71 (m, 1H), 2.61-2.53 (m, 1H), 2.18-2.05 (m, 1H), 1.52 (d, J = 13.2 Hz, 6H). |
| 52 | 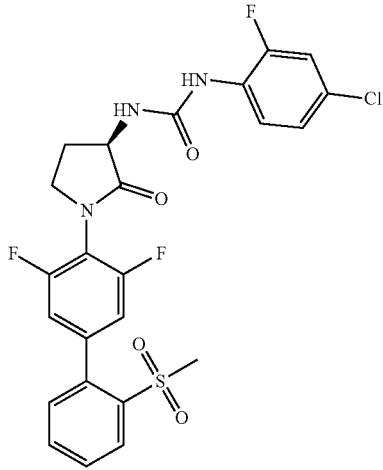 [SMILES: CS(=O)(=O)c1ccccc1-c1cc(F)c(N2CC[C@@H](NC(=O)Nc3ccc(Cl)cc3F)C2=O)c(F)c1] | 538.1 | Method D, RT = 1.774 min, 100% | ¹H NMR (400 MHz, DMSO-$d_6$) δ = 8.61 (d, J = 2.2 Hz, 1H), 8.23-8.04 (m, 2H), 7.87-7.63 (m, 2H), 7.49 (dd, J = 7.5, 1.1 Hz, 1H), 7.42 (dd, J = 11.1, 2.3 Hz, 1H), 7.35 (d, J = 9.0 Hz, 2H), 7.24-7.11 (m, 2H), 4.63-4.50 (m, 1H), 3.83-3.75 (m, 1H), 3.75-3.67 (m, 1H), 3.05 (s, 3H), 2.63-2.55 (m, 1H), 2.19-2.08 (m, 1H). |
| 53 | 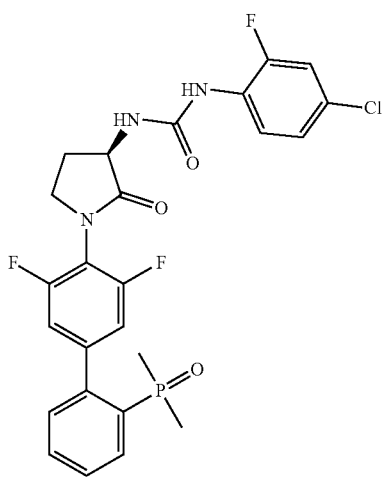 [SMILES: CP(C)(=O)c1ccccc1-c1cc(F)c(N2CC[C@@H](NC(=O)Nc3ccc(Cl)cc3F)C2=O)c(F)c1] | 536.1 | Method C, RT = 1.594 min, 100% | ¹H NMR (400 MHz, DMSO-$d_6$) δ = 8.65-8.57 (m, 1H), 8.19-8.12 (m, 1H), 7.96-7.86 (m, 1H), 7.69-7.56 (m, 2H), 7.46-7.37 (m, 4H), 7.24-7.17 (m, 2H), 4.64-4.53 (m, 1H), 3.84-3.67 (m, 2H), 2.66-2.57 (m, 1H), 2.19-2.06 (m, 1H), 1.52 (d, J = 13.2 Hz, 6H). |

| Ex | Structure | LCMS (M + H)+ | HPLC Method, RT (min.) & Purity | ¹H NMR |
|---|---|---|---|---|
| 54 | 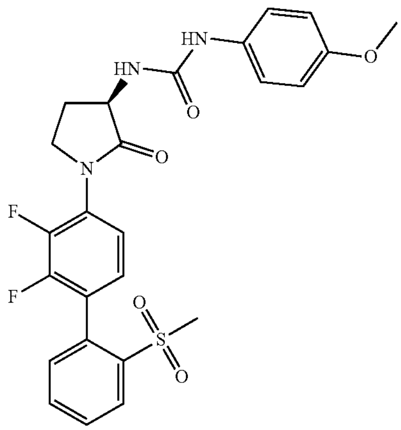 [SMILES: COc1ccc(NC(=O)N[C@@H]2CCN(c3ccc(-c4ccccc4S(C)(=O)=O)c(F)c3F)C2=O)cc1] | 516.2 | Method C, RT = 1.485 min, 98.5% | ¹H NMR (400 MHz, DMSO-d₆) δ = 8.49 (s, 1H), 8.14 (dd, J = 7.8, 1.5 Hz, 1H), 7.91-7.71 (m, 2H), 7.51 (dd, J = 7.8, 1.5 Hz, 1H), 7.41 (t, J = 7.8 Hz, 1H), 7.38-7.22 (m, 3H), 6.92-6.74 (m, 2H), 6.56 (d, J = 7.3 Hz, 1H), 4.56-4.50 (m, 1H), 3.99-3.83 (m, 1H), 3.83-3.75 (m, 1H), 3.71 (s, 3H), 3.06 (s, 3H), 2.61-2.54 (m, 1H), 2.20-2.01 (m, 1H). |
| 55 | 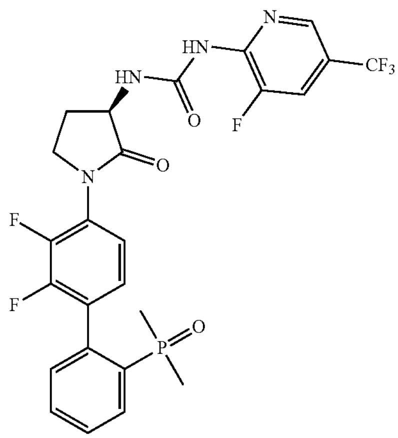 [SMILES: CP(C)(=O)c1ccccc1-c1ccc(N2CC[C@@H](NC(=O)Nc3ncc(C(F)(F)F)cc3F)C2=O)c(F)c1F] | 571.2 | Method C, RT = 1.589 min, 100% | ¹H NMR (400 MHz, DMSO-d₆) δ = 9.86 (s, 1H), 9.13 (d, J = 6.8 Hz, 1H), 8.49 (s, 1H), 8.22 (dd, J = 10.4, 1.8 Hz, 1H), 8.00-7.84 (m, 1H), 7.72-7.56 (m, 2H), 7.46-7.30 (m, 2H), 7.27 (t, J = 7.8 Hz, 1H), 4.74-4.61 (m, 1H), 4.00-3.87 (m, 1H), 3.86-3.78 (m, 1H), 2.66-2.56 (m, 1H), 2.30-2.17 (m, 1H), 1.52 (d, J = 13.2 Hz, 6H). |
| 56 | 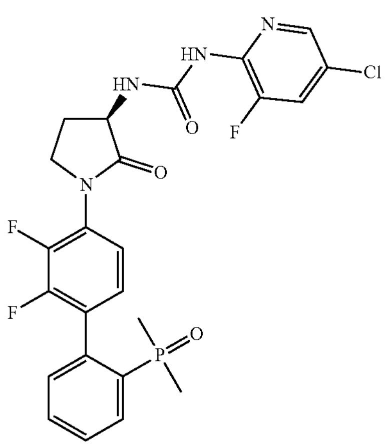 [SMILES: CP(C)(=O)c1ccccc1-c1ccc(N2CC[C@@H](NC(=O)Nc3ncc(Cl)cc3F)C2=O)c(F)c1F] | 537.2 | Method C, RT = 1.475 min, 100% | ¹H NMR (400 MHz, DMSO-d₆) δ = 9.44 (s, 1H), 8.68 (d, J = 6.8 Hz, 1H), 8.19 (s, 1H), 8.05 (dd, J = 10.0, 2.2 Hz, 1H), 7.98-7.88 (m, 1H), 7.67-7.40 (m, 2H), 7.47-7.31 (m, 2H), 7.29-7.21 (m, 1H), 4.70-4.62 (m, 1H), 3.98-3.84 (m, 1H), 3.84-3.74 (m, 1H), 2.63-2.55 (m, 1H), 2.27-2.13 (m, 1H), 1.52 (d, J = 13.2 Hz, 6H). |

-continued

| Ex | Structure | LCMS (M + H)+ | HPLC Method, RT (min.) & Purity | ¹H NMR |
|---|---|---|---|---|
| 57 | 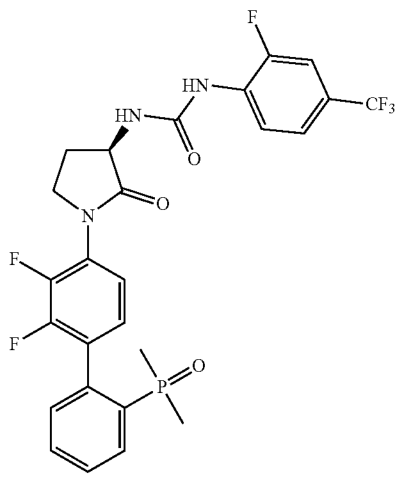 [SMILES: CP(C)(=O)c1ccccc1-c1ccc(N2CC[C@@H](NC(=O)Nc3ccc(C(F)(F)F)cc3F)C2=O)c(F)c1F] | 570.2 | Method C, RT = 1.728 min, 100% | ¹H NMR (400 MHz, DMSO-d$_6$) δ = 8.93 (d, J = 2.0 Hz, 1H), 8.41 (t, J = 8.6 Hz, 1H), 7.98-7.85 (m, 1H), 7.72-7.55 (m, 3H), 7.51 (d, J = 8.3 Hz, 1H), 7.42-7.30 (m, 3H), 7.30-7.22 (m, 1H), 4.65-4.54 (m, 1H), 3.96-3.85 (m, 1H), 3.79-3.45 (m, 1H), 2.65-2.57 (m, 1H), 2.16-2.02 (m, 1H), 1.52 (d, J = 13.2 Hz, 6H). |
| 58 | 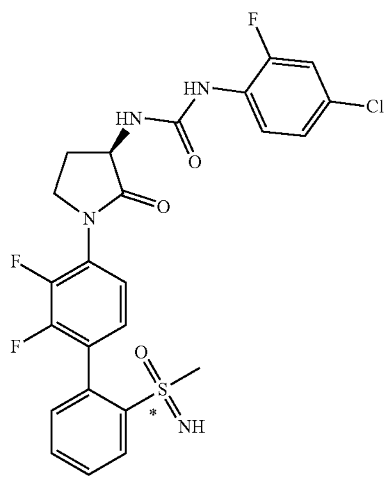 [SMILES: CS(=N)(=O)c1ccccc1-c1ccc(N2CC[C@@H](NC(=O)Nc3ccc(Cl)cc3F)C2=O)c(F)c1F] | 537.2 | Method C, RT = 1.671 min, 100% | ¹H NMR (400 MHz, DMSO-d$_6$) δ = 8.75 (br. s., 1H), 8.19 (d, J = 8.1 Hz, 1H), 8.14 (t, J = 8.9 Hz, 1H), 7.78-7.67 (m, 2H), 7.46-7.23 (m, 5H), 7.23-7.16 (m, 1H), 4.61-4.50 (m, 1H), 4.27 (br. s., 1H), 3.96-3.85 (m, 1H), 3.82-3.75 (m, 1H), 2.93-2.89 (m, 3H), 2.62-2.54 (m, 1H), 2.15-2.04 (m, 1H). |
| 59 | 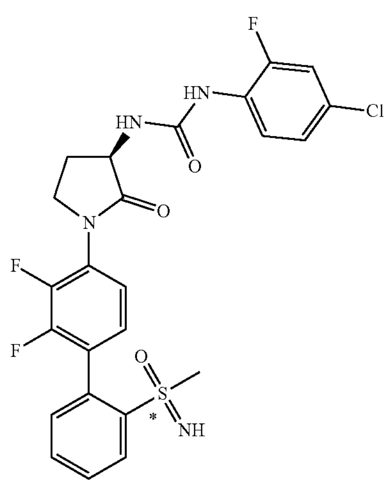 [SMILES: CS(=N)(=O)c1ccccc1-c1ccc(N2CC[C@@H](NC(=O)Nc3ccc(Cl)cc3F)C2=O)c(F)c1F] | 537.2 | Method C, RT = 1.672 min, 100% | ¹H NMR (400 MHz, DMSO-d$_6$) δ = 8.76 (br. s., 1H), 8.26-8.06 (m, 2H), 7.81-7.64 (m, 2H), 7.51-7.29 (m, 5H), 7.20 (ddd, J = 9.0, 2.4, 1.3 Hz, 1H), 4.56 (dd, J = 17.9, 8.3 Hz, 1H), 4.28 (br. s., 1H), 3.92-3.90 (m, 1H), 3.79 (t, J = 8.3 Hz, 1H), 2.93-2.89 (m, 3H), 2.64-2.53 (m, 1H), 2.16-2.01 (m, 1H). |

| Ex | Structure | LCMS (M + H)+ | HPLC Method, RT (min.) & Purity | $^1$H NMR |
|---|---|---|---|---|
| 60 | 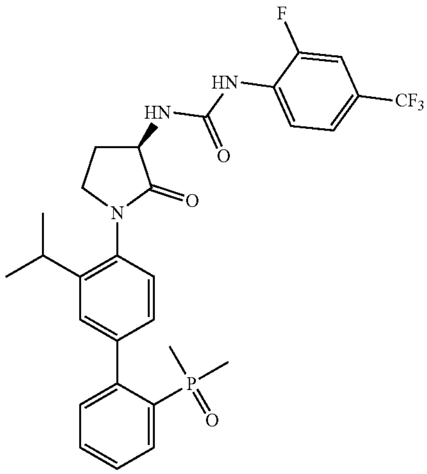 [SMILES: CC(C)c1cc(-c2ccccc2P(C)(C)=O)ccc1N1CC[C@@H](NC(=O)Nc2ccc(C(F)(F)F)cc2F)C1=O] | 576.3 | Method C, RT = 2.041 min, 100% | $^1$H NMR (400 MHz, DMSO-d$_6$) δ = 8.91 (d, J = 2.9 Hz, 1H), 8.43 (t, J = 8.6 Hz, 1H), 7.98 (dd, J = 12.7, 7.8 Hz, 1H), 7.71-7.60 (m, 2H), 7.60-7.47 (m, 3H), 7.37 (dd, J = 7.0, 3.5 Hz, 1H), 7.35-7.23 (m, 3H), 4.63-4.51 (m, 1H), 3.86-3.74 (m, 1H), 3.58 (t, J = 8.7 Hz, 1H), 3.09-2.99 (m, 1H), 2.66-2.56 (m, 1H), 2.17-2.02 (m, 1H), 1.34 (d, J = 13.2 Hz, 6H), 1.18 (d, J = 6.8 Hz, 3H), 1.20 (d, J = 6.8 Hz, 3H). |
| 61 | 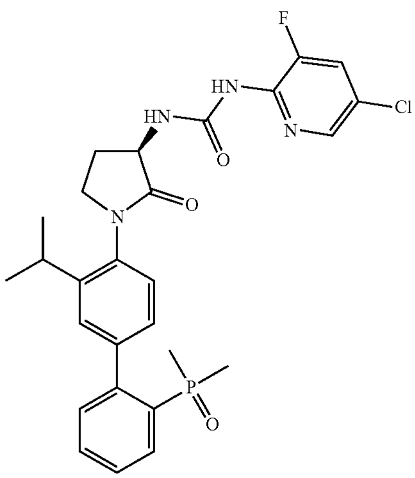 [SMILES: CC(C)c1cc(-c2ccccc2P(C)(C)=O)ccc1N1CC[C@@H](NC(=O)Nc2ncc(Cl)cc2F)C1=O] | 543.2 | Method C, RT = 1.774 min, 99.7% | $^1$H NMR (400 MHz, DMSO-d$_6$) δ = 9.44 (s, 1H), 8.67 (d, J = 5.9 Hz, 1H), 8.19 (d, J = 2.2 Hz, 1H), 8.04 (dd, J = 10.1, 2.2 Hz, 1H), 8.01-7.91 (m, 1H), 7.68-7.59 (m, 1H), 7.59-7.48 (m, 2H), 7.37 (dd, J = 6.4, 2.4 Hz, 1H), 7.31 (d, J = 1.0 Hz, 2H), 4.60-4.55 (m, 1H), 3.83-3.75 (m, 1H), 3.64-3.59 (m, 1H), 3.13-3.05 (m, 1H), 2.63-2.54 (m, 1H), 3.13-3.05 (m, 1H), 1.34 (d, J = 13.2 Hz, 6H), 1.19 (d, J = 6.8 Hz, 3H), 1.20 (d, J = 6.8 Hz, 3H). |
| 62 | 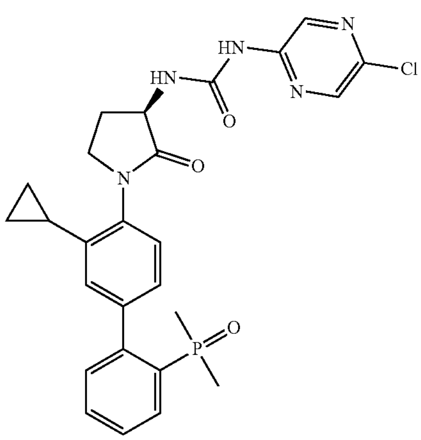 [SMILES: CP(C)(=O)c1ccccc1-c1ccc(N2CC[C@@H](NC(=O)Nc3cnc(Cl)cn3)C2=O)c(C2CC2)c1] | 524.2 | Method C, RT = 1.607 min, 99.6% | $^1$H NMR (400 MHz, DMSO-d$_6$) δ = 9.74 (br. s., 1H), 8.90 (d, J = 1.5 Hz, 1H), 8.41 (d, J = 1.2 Hz, 1H), 7.98-7.89 (m, 1H), 7.67-7.43 (m, 3H), 7.41-7.20 (m, 3H), 7.13 (d, J = 1.7 Hz, 1H), 4.64-4.54 (m, 1H), 3.83 (td, J = 9.5, 6.7 Hz, 1H), 3.73-3.65 (m, 1H), 2.65-2.56 (m, 1H), 2.24-2.13 (m, 1H), 2.03-1.93 (m, 1H), 1.34 (d, J = 13.2 Hz, 6H), 1.02-0.82 (m, 2H), 0.80-0.65 (m, 2H). |

-continued

| Ex | Structure | LCMS (M + H)+ | HPLC Method, RT (min.) & Purity | ¹H NMR |
|----|-----------|---------------|-------------------------------|--------|
| 63 | 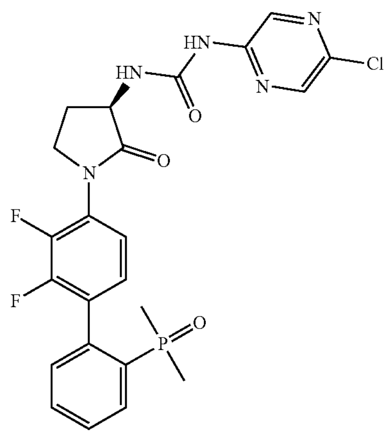 [SMILES: CP(C)(=O)c1ccccc1-c1ccc(N2CC[C@@H](NC(=O)Nc3cnc(Cl)cn3)C2=O)c(F)c1F] | 520.2 | Method C, RT = 1.517 min, 100% | ¹H NMR (400 MHz, DMSO-d$_6$) δ = 9.83 (br. s., 1H), 8.90 (s, 1H), 8.41 (d, J = 1.5 Hz, 1H), 7.99-7.85 (m, 1H), 7.73-7.53 (m, 3H), 7.51-7.30 (m, 2H), 7.30-7.20 (m, 1H), 4.67-4.55 (m, 1H), 3.95-3.87 (m, 1H), 3.80-3.77 (m, 1H), 2.64-2.56 (m, 1H), 2.28-2.00 (m, 1H), 1.52 (d, J = 13.2 Hz, 6H). |
| 64 | 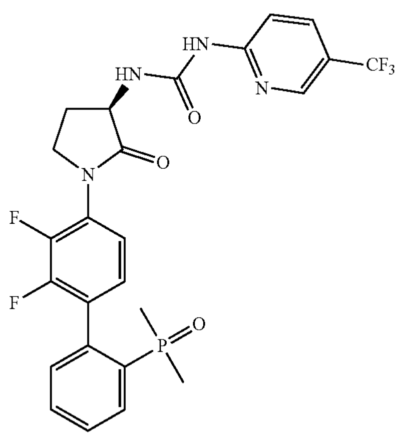 [SMILES: CP(C)(=O)c1ccccc1-c1ccc(N2CC[C@@H](NC(=O)Nc3ccc(C(F)(F)F)cn3)C2=O)c(F)c1F] | 553.3 | Method C, RT = 1.742 min, 100% | ¹H NMR (400 MHz, DMSO-d$_6$) δ = 9.79 (s, 1H), 8.59 (s, 1H), 8.08 (dd, J = 8.8, 2.2 Hz, 2H), 7.96-7.86 (m, 1H), 7.79 (d, J = 8.8 Hz, 1H), 7.72-7.55 (m, 2H), 7.45-7.31 (m, 2H), 7.31-7.23 (m, 1H), 4.70-4.59 (m, 1H), 3.98-3.84 (m, 1H), 3.84-3.74 (m, 1H), 2.65-2.55 (m, 1H), 2.28-2.08 (m, 1H), 1.53 (d, J = 13.2 Hz, 6H). |
| 65 | 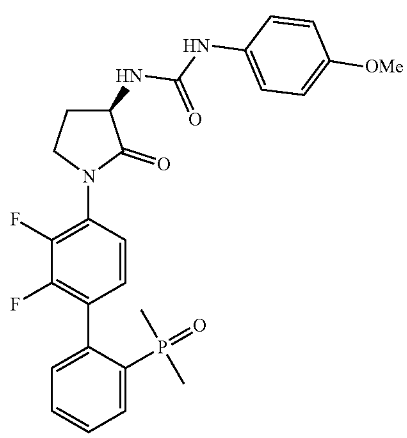 [SMILES: COc1ccc(NC(=O)N[C@@H]2CCN(c3ccc(-c4ccccc4P(C)(C)=O)c(F)c3F)C2=O)cc1] | 514.3 | Method C, RT = 1.496 min, 97.9% | ¹H NMR (400 MHz, DMSO-d$_6$) δ = 8.48 (s, 1H), 7.98-7.88 (m, 1H), 7.72-7.52 (m, 2H), 7.43-7.19 (m, 5H), 6.88-6.77 (m, 2H), 6.55 (d, J = 7.3 Hz, 1H), 4.58-4.49 (m, 1H), 3.93-3.83 (m, 1H), 3.77-3.74 (m, 1H), 3.71 (s, 3H), 2.60-2.54 (m, 1H), 2.23-1.99 (m, 1H), 1.52 (d, J = 13.2 Hz, 6H). |

| Ex | Structure | LCMS (M + H)+ | HPLC Method, RT (min.) & Purity | ¹H NMR |
|---|---|---|---|---|
| 66 | 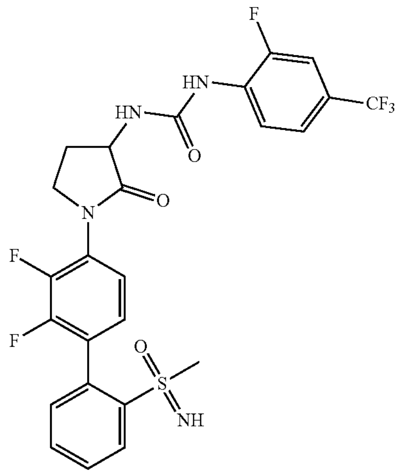 [SMILES: CS(=N)(=O)c1ccccc1-c1ccc(N2CCC(NC(=O)Nc3ccc(C(F)(F)F)cc3F)C2=O)c(F)c1F] | 571.2 | Method C, RT = 1.815 min, 96.2% | ¹H NMR (400 MHz, DMSO-d$_6$) δ = 8.41 (t, J = 8.2 Hz, 1H), 8.18 (br. s., 1H), 7.80-7.69 (m, 2H), 7.67 (d, J = 10.0 Hz, 1H), 7.52 (d, J = 8.6 Hz, 1H), 7.46-7.29 (m, 4H), 7.29-7.06 (m, 1H), 4.65-4.53 (m, 1H), 3.98-3.86 (m, 1H), 3.80 (t, J = 8.9 Hz, 1H), 2.93-2.89 (m, 3H), 2.64-2.55 (m, 1H), 2.16-2.04 (m, 1H). |
| 67 | 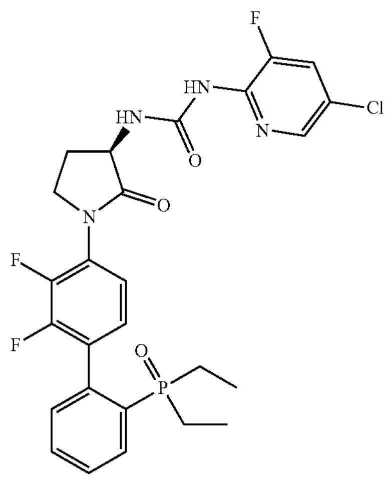 [SMILES: CCP(=O)(CC)c1ccccc1-c1ccc(N2CC[C@@H](NC(=O)Nc3ncc(Cl)cc3F)C2=O)c(F)c1F] | 565.2 | Method C, RT = 1.804 min, 100% | ¹H NMR (400 MHz, DMSO-d$_6$) δ = 9.45 (s, 1H), 8.69 (d, J = 6.4 Hz, 1H), 8.19 (s, 1H), 8.05 (d, J = 10.3 Hz, 1H), 7.89 (dd, J = 11.5, 7.3 Hz, 1H), 7.64 (quin, J = 7.8 Hz, 2H), 7.48-7.26 (m, 2H), 7.17 (t, J = 7.9 Hz, 1H), 4.70-4.59 (m, 1H), 3.96-3.85 (m, 1H), 3.85-3.74 (m, 1H), 2.63-2.54 (m, 1H), 2.29-2.11 (m, 1H), 1.80-1.60 (m, 4H), 0.93-0.88 (m, 6H). |
| 68 | 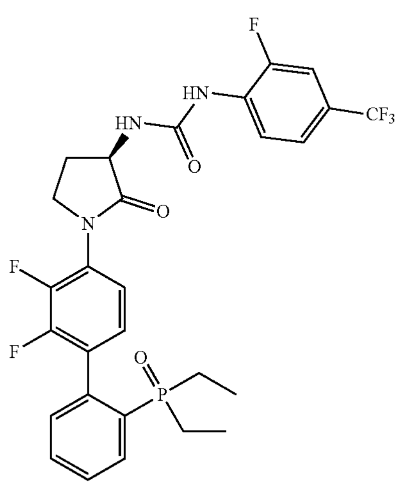 [SMILES: CCP(=O)(CC)c1ccccc1-c1ccc(N2CC[C@@H](NC(=O)Nc3ccc(C(F)(F)F)cc3F)C2=O)c(F)c1F] | 598.2 | Method C, RT = 2.038 min, 100% | ¹H NMR (400 MHz, DMSO-d$_6$) δ = 8.91 (br. s., 1H), 8.41 (t, J = 8.6 Hz, 1H), 7.97-7.83 (m, 1H), 7.75-7.56 (m, 3H), 7.51 (d, J = 8.8 Hz, 1H), 7.42-7.23 (m, 3H), 7.22-7.11 (m, 1H), 4.63-4.51 (m, 1H), 3.96-3.87 (m, 1H), 3.81-3.76 (m, 1H), 2.64-2.56 (m, 1H), 2.17-2.02 (m, 1H), 1.80-1.60 (m, 4H), 0.93-0.88 (m, 6H). |

-continued

| Ex | Structure | LCMS (M + H)+ | HPLC Method, RT (min.) & Purity | ¹H NMR |
|---|---|---|---|---|
| 69 | 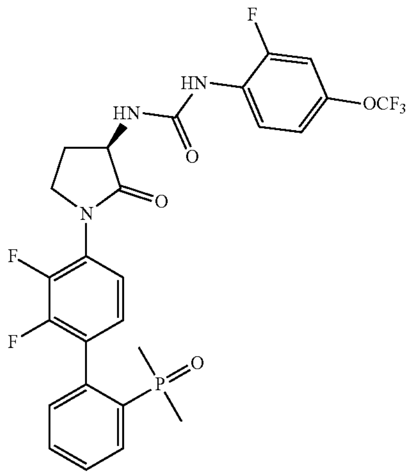 [SMILES: CP(C)(=O)c1ccccc1-c1ccc(N2CC[C@@H](NC(=O)Nc3ccc(OC(F)(F)F)cc3F)C2=O)c(F)c1F] | 586.2 | Method C, RT = 1.903 min, 100% | ¹H NMR (400 MHz, DMSO-$d_6$) δ = 8.70 (s, 1H), 8.22 (t, J = 9.2 Hz, 1H), 7.92 (dd, J = 12.5, 7.8 Hz, 1H), 7.73-7.55 (m, 2H), 7.49-7.30 (m, 3H), 7.30-7.23 (m, 1H), 7.23-7.09 (m, 2H), 4.63-4.52 (m, 1H), 4.00-3.84 (m, 1H), 3.80-3.75 (m, 1H), 2.64-2.56 (m, 1H), 2.18-2.01 (m, 1H), 1.52 (d, J = 13.2 Hz, 6H). |
| 70 | 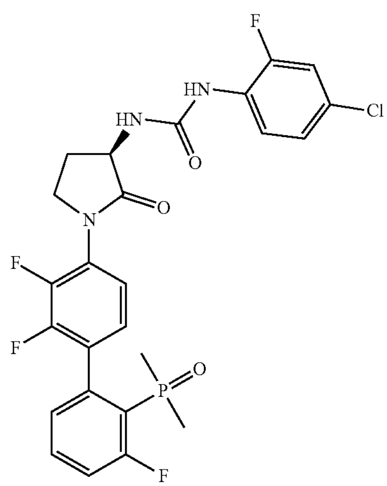 [SMILES: CP(C)(=O)c1c(F)cccc1-c1ccc(N2CC[C@@H](NC(=O)Nc3ccc(Cl)cc3F)C2=O)c(F)c1F] | 554.2 | Method C, RT = 1.663 min, 99.2% | ¹H NMR (400 MHz, DMSO-$d_6$) δ = 8.63 (d, J = 5.4 Hz, 1H), 8.16 (t, J = 8.9 Hz, 1H), 7.79-7.68 (m, 1H), 7.52-7.36 (m, 2H), 7.35-7.24 (m, 1H), 7.24-7.08 (m, 4H), 4.61-4.50 (m, 1H), 3.94-3.82 (m, 1H), 3.79-3.67 (m, 1H), 2.59 (dd, J = 12.7, 7.6 Hz, 1H), 2.13-2.01 (m, 1H), 1.86-1.59 (m, 6H) |
| 71 | 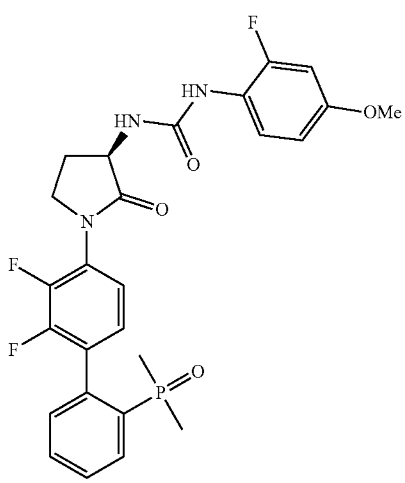 [SMILES: COc1ccc(NC(=O)N[C@@H]2CCN(c3ccc(-c4ccccc4P(C)(C)=O)c(F)c3F)C2=O)c(F)c1] | 532.3 | Method D, RT = 1.383 min, 98.9% | ¹H NMR (400 MHz, DMSO-$d_6$) δ = 8.24 (s, 1H), 7.92 (dd, J = 12.2, 8.1 Hz, 1H), 7.84 (t, J = 9.3 Hz, 1H), 7.74-7.55 (m, 2H), 7.37 (d, J = 6.8 Hz, 2H), 7.30-7.22 (m, 1H), 6.97 (d, J = 7.1 Hz, 1H), 6.87 (dd, J = 12.2, 2.6 Hz, 1H), 6.72 (dd, J = 8.9, 1.8 Hz, 1H), 4.61-4.48 (m, 1H), 3.95-3.84 (m, 1H), 3.82-3.59 (m, 1H), 3.74 (s, 3H), 2.62-2.55 (m, 1H), 2.15-2.02 (m, 1H), 1.52 (d, J = 13.2 Hz, 6H). |

-continued

| Ex | Structure | LCMS (M + H)+ | HPLC Method, RT (min.) & Purity | ¹H NMR |
|---|---|---|---|---|
| 72 | 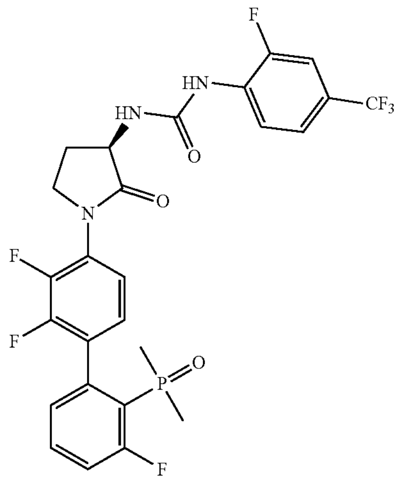 [SMILES: CP(C)(=O)c1c(F)cccc1-c1ccc(N2CC[C@@H](NC(=O)Nc3ccc(C(F)(F)F)cc3F)C2=O)c(F)c1F] | 588.2 | Method C, RT = 1.794 min, 100% | ¹H NMR (400 MHz, DMSO-d$_6$) δ = 8.95 (dd, J = 8.2, 2.5 Hz, 1H), 8.41 (t, J = 8.2 Hz, 1H), 7.76-7.65 (m, 2H), 7.53-7.43 (m, 2H), 7.38-7.28 (m, 2H), 7.23-7.16 (m, 2H), 4.62-4.54 (m, 1H), 3.94-3.83 (m, 1H), 3.81-3.70 (m, 1H), 2.64-2.53 (m, 1H), 2.16-2.02 (m, 1H), 1.76-1.64 (m, 6H). |
| 73 | 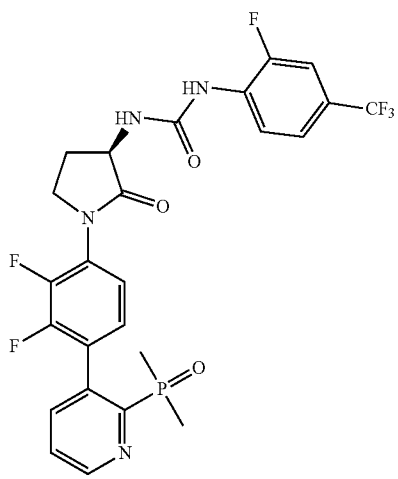 | 588.2 (M + NH$_4$)$^+$ | Method D, RT = 1.647 min, 100% | ¹H NMR (400 MHz, DMSO-d$_6$) δ = 8.94 (d, J = 2.9 Hz, 1H), 8.84 (d, J = 4.2 Hz, 1H), 8.42 (t, J = 8.3 Hz, 1H), 7.87-7.86 (m, 1H), 7.73-7.62 (m, 2H), 7.52 (d, J = 8.6 Hz, 1H), 7.43-7.25 (m, 3H), 4.65-4.52 (m, 1H), 3.98-3.86 (m, 1H), 3.82-3.70 (m, 1H), 2.64-2.56 (m, 1H), 2.16-2.04 (m, 1H), 1.62 (d, J = 13.2 Hz, 6H). |
| 74 | 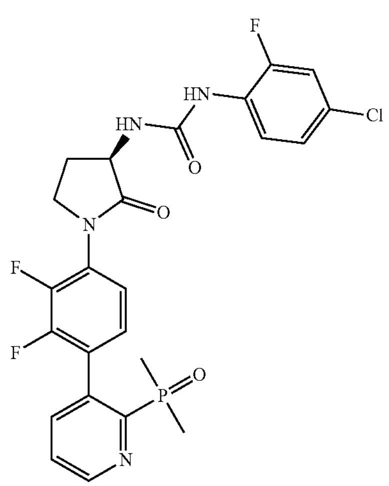 [SMILES: CP(C)(=O)c1ncccc1-c1ccc(N2CC[C@@H](NC(=O)Nc3ccc(Cl)cc3F)C2=O)c(F)c1F] | 554.2 (M + NH$_4$)$^+$ | Method D, RT = 1.498 min, 100% | ¹H NMR (400 MHz, DMSO-d$_6$) δ = 8.84 (br d, J = 4.2 Hz, 1H), 8.64 (s, 1H), 8.15 (t, J = 8.9 Hz, 1H), 7.86 (dd, J = 3.5, 7.5 Hz, 1H), 7.70-7.61 (m, 1H), 7.42 (dd, J = 2.4, 11.0 Hz, 1H), 7.37 (br d, J = 8.1 Hz, 1H), 7.32-7.24 (m, 1H), 7.20 (br d, J = 7.6 Hz, 2H), 4.62-4.50 (m, 1H), 3.95-3.84 (m, 1H), 3.82-3.71 (m, 1H), 2.64-2.56 (m, 1H), 2.13-2.00 (m, 1H), 1.62 (d, J = 13.4 Hz, 6H). |

| Ex | Structure | LCMS (M + H)+ | HPLC Method, RT (min.) & Purity | ¹H NMR |
|---|---|---|---|---|
| 75 | 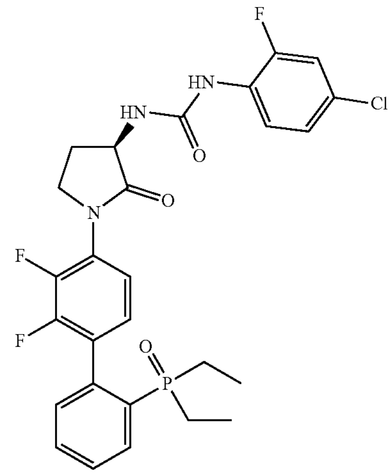 [SMILES: CCP(=O)(CC)c1ccccc1-c1ccc(N2CC[C@@H](NC(=O)Nc3ccc(Cl)cc3F)C2=O)c(F)c1F] | 564.2 | Method C, RT = 1.723 min, 99.9% | ¹H NMR (400 MHz, DMSO-d$_6$) δ = 8.62 (d, J = 2.4 Hz, 1H), 8.16 (t, J = 8.9 Hz, 1H), 7.87 (ddd, J = 11.6, 7.5, 1.7 Hz, 1H), 7.70-7.53 (m, 2H), 7.43 (dd, J = 11.0, 2.4 Hz, 1H), 7.36 (ddd, J = 7.5, 3.6, 1.6 Hz, 1H), 7.33-7.26 (m, 2H), 7.23-7.16 (m, 2H), 4.64-4.50 (m, 1H), 3.84-3.74 (m, 1H), 3.73-3.63 (m, 1H), 2.66-2.57 (m, 1H), 2.19-2.01 (m, 1H), 1.71 (m, 4H), 0.93-0.88 (m, 6H). |
| 76 | 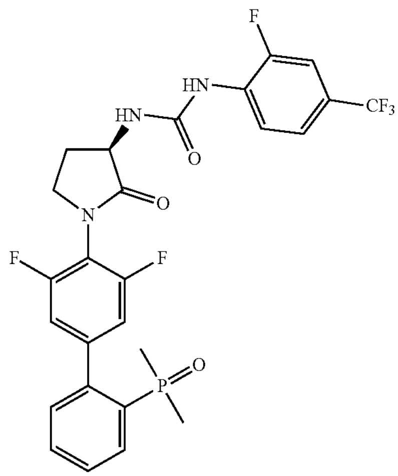 [SMILES: CP(C)(=O)c1ccccc1-c1cc(F)c(N2CC[C@@H](NC(=O)Nc3ccc(C(F)(F)F)cc3F)C2=O)c(F)c1] | 570.2 | Method C, RT = 1.867 min, 98.9% | ¹H NMR (400 MHz, DMSO-d$_6$) δ = 8.91 (d, J = 2.9 Hz, 1H), 8.41 (m, 1H), 7.91 (ddd, J = 13.0, 7.6, 1.2 Hz, 1H), 7.73-7.56 (m, 3H), 7.52 (d, J = 9.5 Hz, 1H), 7.46-7.38 (m, 3H), 7.35 (d, J = 7.1 Hz, 1H), 4.68-4.55 (m, 1H), 3.85-3.76 (m, 1H), 3.74-3.66 (m, 1H), 2.67-2.59 (m, 1H), 2.21-2.10 (m, 1H), 1.49 (d, J = 13.5 Hz, 6H). |
| 77 | 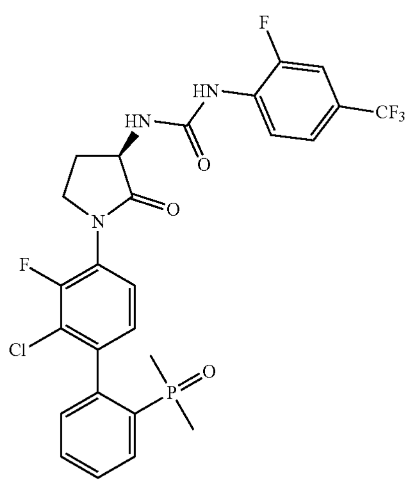 [SMILES: CP(C)(=O)c1ccccc1-c1ccc(N2CC[C@@H](NC(=O)Nc3ccc(C(F)(F)F)cc3F)C2=O)c(F)c1Cl] | 586.2 | Method C, RT = 1.781 min, 99.8% | ¹H NMR (400 MHz, DMSO-d$_6$) δ = 8.95 (t, J = 3.2 Hz, 1H), 8.42 (t, J = 8.2 Hz, 1H), 8.01-7.90 (m, 1H), 7.70-7.58 (m, 3H), 7.55-7.47 (m, 2H), 7.39-7.21 (m, 3H), 4.63-4.53 (m, 1H), 3.97-3.85 (m, 1H), 3.82-3.70 (m, 1H), 2.64-2.55 (m, 1H), 2.17-2.03 (m, 1H), 1.48 (d, J = 12.8 Hz, 3H), 1.46 (d, J = 12.8 Hz, 3H). |

-continued

| Ex | Structure | LCMS (M + H)+ | HPLC Method, RT (min.) & Purity | ¹H NMR |
|---|---|---|---|---|
| 78 | 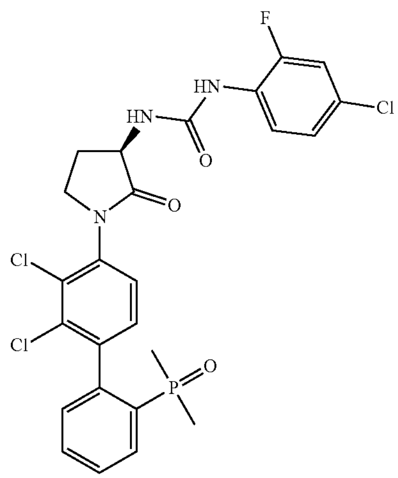 [SMILES: CP(C)(=O)c1ccccc1-c1ccc(N2CC[C@@H](NC(=O)Nc3ccc(Cl)cc3F)C2=O)c(Cl)c1Cl] | 568.1 | Method C, RT = 1.691 min, 99.8% | ¹H NMR (400 MHz, DMSO-$d_6$) δ = 8.65 (dd, J = 6.1, 2.4 Hz, 1H), 8.17 (t, J = 8.9 Hz, 1H), 7.98-7.88 (m, 1H), 7.70-7.57 (m, 2H), 7.54-7.39 (m, 3H), 7.29 (td, J = 3.5, 7.1 Hz, 1H), 7.24-7.13 (m, 2H), 4.63-4.49 (m, 1H), 3.87-3.76 (m, 1H), 3.73-3.64 (m, 1H), 2.66-2.57 (m, 1H), 2.16-2.01 (m, 1H), 1.52-1.44 (m, 6H). |
| 79 | 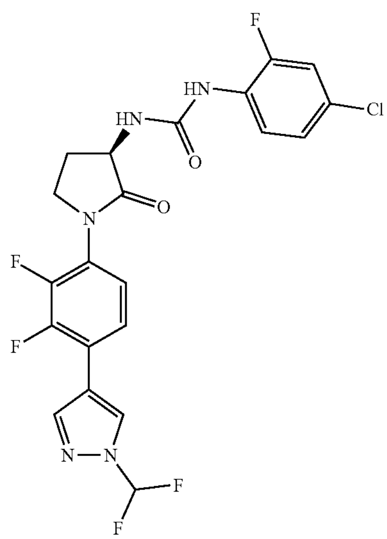 [SMILES: O=C(Nc1ccc(Cl)cc1F)N[C@@H]1CCN(c2ccc(-c3cnn(C(F)F)c3)c(F)c2F)C1=O] | 500.1 | Method C, RT = 1.763 min, 100% | ¹H NMR (400 MHz, DMSO-$d_6$) δ = 8.73 (s, 1H), 8.63 (d, J = 2.2 Hz, 1H), 8.33 (s, 1H), 8.15 (t, J = 8.8 Hz, 1H), 7.90 (s, 1H), 7.70 (t, J = 7.2 Hz, 1H), 7.48-7.33 (m, 2H), 7.29-7.11 (m, 2H), 4.55 (dd, J = 18.1, 8.6 Hz, 1H), 3.92-3.84 (m, 1H), 3.81-3.72 (m, 1H), 2.61 (m, 1H), 2.12-2.00 (m, 1H). |
| 80 | 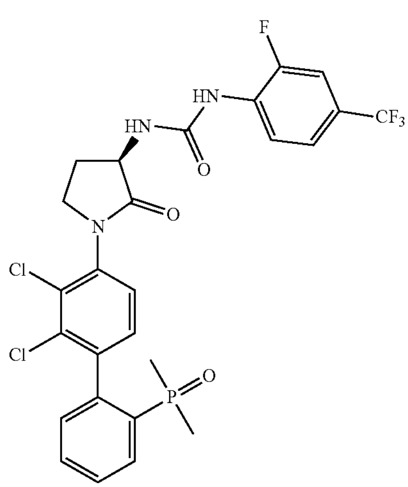 [SMILES: CP(C)(=O)c1ccccc1-c1ccc(N2CC[C@@H](NC(=O)Nc3ccc(C(F)(F)F)cc3F)C2=O)c(Cl)c1Cl] | 602.1 | Method C, RT = 1.821 min, 99.5% | ¹H NMR (400 MHz, DMSO-$d_6$) δ = 8.94 (dd, J = 5.9, 2.9 Hz, 1H), 8.42 (m, 1H), 7.99-7.89 (m, 1H), 7.72-7.55 (m, 3H), 7.54-7.44 (m, 3H), 7.35 (dd, J = 7.1, 2.9 Hz, 1H), 7.32-7.24 (m, 1H), 4.65-4.53 (m, 1H), 3.87-3.78 (m, 1H), 3.74-3.67 (m, 1H), 2.63 (dt, J = 6.4, 5.1 Hz, 1H), 2.17-2.03 (m, 1H), 1.50-1.45 (m, 6H). |

-continued

| Ex | Structure | LCMS (M + H)+ | HPLC Method, RT (min.) & Purity | ¹H NMR |
|---|---|---|---|---|
| 81 | 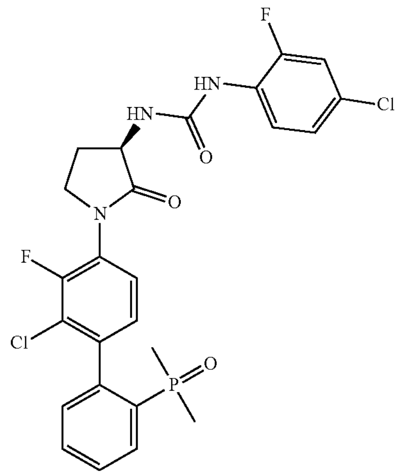 [SMILES: CP(C)(=O)c1ccccc1-c1ccc(N2CC[C@@H](NC(=O)Nc3ccc(Cl)cc3F)C2=O)c(F)c1Cl] | 552.2 | Method D, RT = 2.358 min, 99.7% | ¹H NMR (400 MHz, DMSO-d$_6$) δ = 8.64 (br. s., 1H), 8.15 (t, J = 8.8 Hz, 1H), 7.94 (dd, J = 12.5, 1.5 Hz, 1H), 7.69-7.58 (m, 2H), 7.55-7.48 (m, 1H), 7.42 (dd, J = 11.3, 2.3 Hz, 1H), 7.32 (d, J = 7.8 Hz, 1H), 7.30-7.26 (m, 1H), 7.22-7.16 (m, 2H), 4.56 (s, 1H), 3.96-3.83 (m, 1H), 3.83-3.70 (m, 1H), 2.61-2.57 (m, 1H), 2.13-2.01 (m, 1H), 1.48 (d, J = 12.8 Hz, 3H), 1.46 (d, J = 12.8 Hz, 3H). |
| 82 | 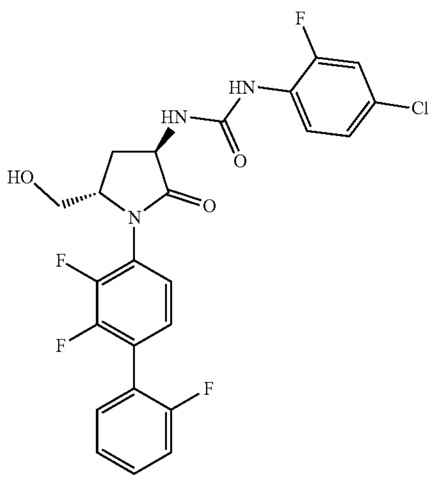 [SMILES: O=C(Nc1ccc(Cl)cc1F)N[C@@H]1C[C@@H](CO)N(c2ccc(-c3ccccc3F)c(F)c2F)C1=O] | 508.1 | Method C, RT = 1.834 min, 100% | ¹H NMR (400 MHz, DMSO-d$_6$) δ = 8.63 (d, J = 1.0 Hz, 1H), 8.15 (t, J = 8.8 Hz, 1H), 7.63-7.50 (m, 2H), 7.50-7.29 (m, 5H), 7.24-7.15 (m, 1H), 7.11 (d, J = 7.3 Hz, 1H), 5.10 (t, J = 4.9 Hz, 1H), 4.81-4.62 (m, 1H), 4.29-4.12 (m, 1H), 3.49-3.47 (m, 2H), 2.55-2.52 (m, 1H), 2.31-2.21 (m, 1H). |
| 83 | 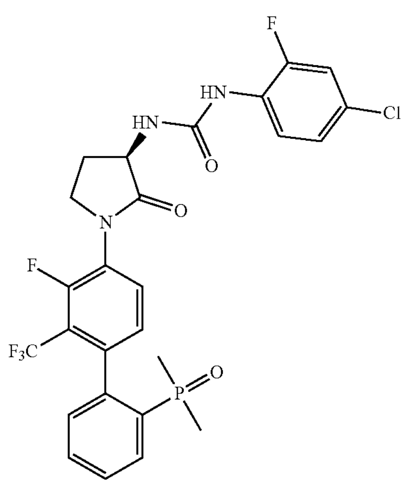 [SMILES: CP(C)(=O)c1ccccc1-c1ccc(N2CC[C@@H](NC(=O)Nc3ccc(Cl)cc3F)C2=O)c(F)c1C(F)(F)F] | 586.2 | Method C, RT = 2.031 min, 100% | ¹H NMR (400 MHz, DMSO-d$_6$) δ = 8.66 (d, J = 2.5 Hz, 1H), 8.15 (t, J = 8.8 Hz, 1H), 7.89-7.80 (m, 1H), 7.75 (t, J = 7.8 Hz, 1H), 7.63-7.53 (m, 2H), 7.43 (dd, J = 11.3, 2.3 Hz, 1H), 7.31-7.13 (m, 4H), 4.62-4.50 (m, 1H), 3.97-3.94 (m, 1H), 3.81-3.73 (m, 1H), 2.63-2.55 (m, 1H), 2.17-2.05 (m, 1H), 1.54 (d, J = 13.6 Hz, 3H), 1.52 (d, J = 13.6 Hz, 3H). |

-continued

| Ex | Structure | LCMS (M + H)+ | HPLC Method, RT (min.) & Purity | ¹H NMR |
|---|---|---|---|---|
| 84 | 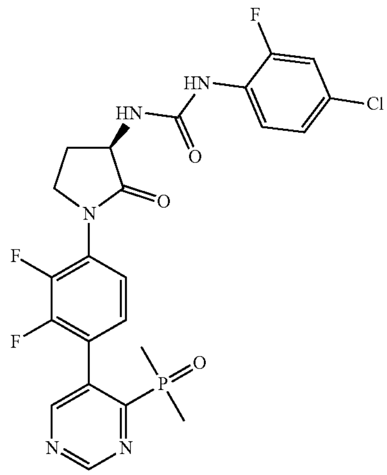 [SMILES: CP(C)(=O)c1ncncc1-c1ccc(N2CC[C@@H](NC(=O)Nc3ccc(Cl)cc3F)C2=O)c(F)c1F] | 555.2 (M + NH₄)⁺ | Method C, RT = 1.369 min, 92.6% | ¹H NMR (400 MHz, DMSO-d$_6$) δ = 9.47 (s, 1H), 8.97 (d, J = 5.6 Hz, 1H), 8.66 (d, J = 2.4 Hz, 1H), 8.15 (t, J = 8.9 Hz, 1H), 7.48-7.34 (m, 3H), 7.25-7.17 (m, 2H), 4.62-4.54 (m, 1H), 3.96-3.85 (m, 1H), 3.78 (t, J = 8.6 Hz, 1H), 2.63-2.54 (m, 1H), 2.15-2.04 (m, 1H), 1.69 (d, J = 13.7 Hz, 6H). |
| 85 | 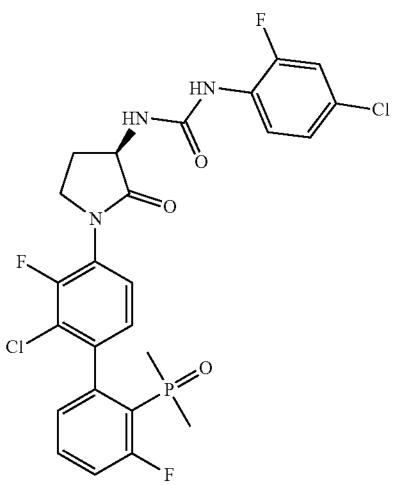 [SMILES: CP(C)(=O)c1c(F)cccc1-c1ccc(N2CC[C@@H](NC(=O)Nc3ccc(Cl)cc3F)C2=O)c(F)c1Cl] | 570.2 | Method C, RT = 1.722 min, 100% | ¹H NMR (400 MHz, DMSO-d$_6$) δ = 8.68-8.58 (m, 1H), 8.15 (t, J = 8.8 Hz, 1H), 7.76-7.65 (m, 1H), 7.52-7.35 (m, 3H), 7.25-7.15 (m, 3H), 7.13-7.06 (m, 1H), 4.59-4.48 (m, 1H), 3.91-3.81 (m, 1H), 3.78-3.67 (m, 1H), 2.55-2.52 (m, 1H), 2.13-2.01 (m, 1H), 1.73-1.61 (m, 6H). |
| 86 | 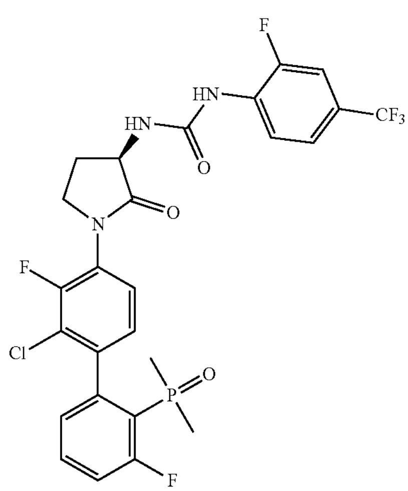 [SMILES: CP(C)(=O)c1c(F)cccc1-c1ccc(N2CC[C@@H](NC(=O)Nc3ccc(C(F)(F)F)cc3F)C2=O)c(F)c1Cl] | 604.1 | Method C, RT = 1.834 min, 100% | ¹H NMR (400 MHz, DMSO-d$_6$) δ = 8.98-8.91 (m, 1H), 8.45-8.38 (m, 1H), 7.76-7.62 (m, 2H), 7.52 (br. d, J = 9.3 Hz, 1H), 7.48-7.40 (m, 2H), 7.36-7.30 (m, 1H), 7.24-7.18 (m, 1H), 7.11 (d, J = 6.6 Hz, 1H), 4.62-4.52 (m, 1H), 3.92-3.83 (m, 1H), 3.78-3.70 (m, 1H), 2.64-2.56 (m, 1H), 2.14-2.06 (m, 1H), 1.72-1.64 (m, 6H). |

| Ex | Structure | LCMS (M + H)+ | HPLC Method, RT (min.) & Purity | $^1$H NMR |
|---|---|---|---|---|
| 87 | 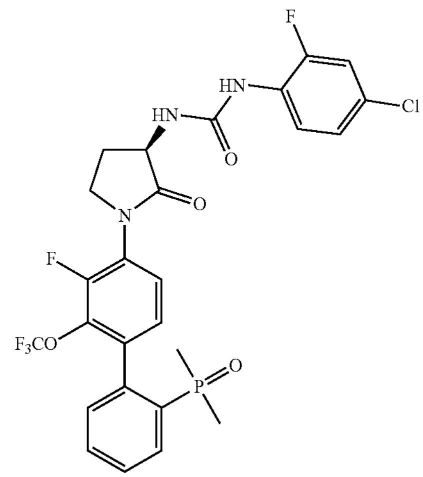 [SMILES: CP(C)(=O)c1ccccc1-c1ccc(N2CC[C@@H](NC(=O)Nc3ccc(Cl)cc3F)C2=O)c(F)c1OC(F)(F)F] | 602.2 | Method C, RT = 1.795 min, 100% | $^1$H NMR (400 MHz, DMSO-$d_6$) δ = 8.65 (dd, J = 1.7, 8.8 Hz, 1H), 8.15 (t, J = 8.9 Hz, 1H), 7.88 (dd, J = 7.3, 12.7 Hz, 1H), 7.70-7.53 (m, 3H), 7.43 (dd, J = 2.4, 11.0 Hz, 1H), 7.38-7.30 (m, 2H), 7.24-7.10 (m, 2H), 4.61-4.52 (m, 1H), 3.96-3.85 (m, 1H), 3.81-3.71 (m, 1H), 2.61-2.54 (m, 1H), 2.17-2.03 (m, 1H), 1.64-1.48 (m, 6H). |
| 88 | 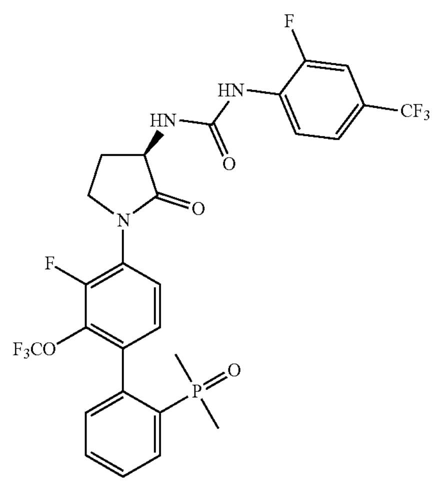 [SMILES: CP(C)(=O)c1ccccc1-c1ccc(N2CC[C@@H](NC(=O)Nc3ccc(C(F)(F)F)cc3F)C2=O)c(F)c1OC(F)(F)F] | 636.2 | Method C, RT = 1.919 min, 100% | $^1$H NMR (400 MHz, DMSO-$d_6$) δ = 8.94 (dd, J = 2.9, 8.6 Hz, 1H), 8.41 (m, 1H), 7.92-7.82 (m, 1H), 7.71-7.54 (m, 4H), 7.51 (d, J = 8.8 Hz, 1H), 7.39-7.31 (m, 3H), 4.63-4.53 (m, 1H), 3.96-3.87 (m, 1H), 3.81-3.73 (m, 1H), 2.63-2.57 (m, 1H), 2.18-2.06 (m, 1H), 1.61-1.50 (m, 6H). |
| 89 | 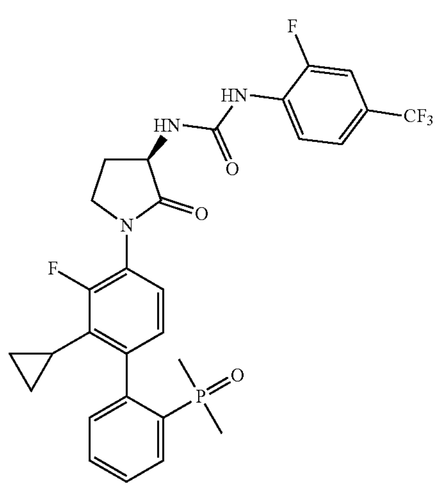 [SMILES: CP(C)(=O)c1ccccc1-c1ccc(N2CC[C@@H](NC(=O)Nc3ccc(C(F)(F)F)cc3F)C2=O)c(F)c1C1CC1] | 592.2 | Method C, RT = 1.872 min, 100% | $^1$H NMR (400 MHz, DMSO-$d_6$) δ = 8.96-8.89 (m, 1H), 8.41 (t, J = 8.3 Hz, 1H), 8.03-7.93 (m, 1H), 7.71-7.49 (m, 4H), 7.39-7.26 (m, 3H), 7.14-7.07 (m, 1H), 4.58-4.49 (m, 1H), 3.87-3.78 (m, 1H), 3.74-3.67 (m, 1H), 2.63-2.54 (m, 1H), 2.13-2.02 (m, 1H), 1.60-1.50 (m, 1H), 1.45 (d, J = 13.4 Hz, 3H), 1.42 (d, J = 13.4 Hz, 3H), 0.79-0.72 (m, 1H), 0.71-0.61 (m, 3H). |

-continued

| Ex | Structure | LCMS (M + H)+ | HPLC Method, RT (min.) & Purity | ¹H NMR |
|---|---|---|---|---|
| 90 | 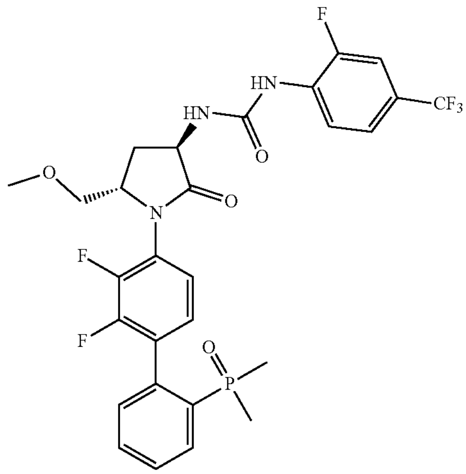 [SMILES: COC[C@@H]1C[C@@H](NC(=O)Nc2ccc(C(F)(F)F)cc2F)C(=O)N1c1ccc(-c2ccccc2P(C)(C)=O)c(F)c1F] | 614.2 | Method C, RT = 1.768 min, 99.7% | ¹H NMR (400 MHz, DMSO-$d_6$) δ = 8.94 (d, J = 2.0 Hz, 1H), 8.40 (t, J = 8.3 Hz, 1H), 8.01-7.89 (m, 1H), 7.72-7.58 (m, 3H), 7.51 (m, 1H), 7.40 (m, 1H), 7.34-7.18 (m, 3H), 4.71-4.58 (m, 1H), 4.33 (m, 1H), 3.48 (dd, J = 10.5, 3.9 Hz, 1H), 3.40-3.36 (m, 1H), 3.24 (s, 3H), 2.49-2.44 (m, 1H), 2.37-2.23 (m, 1H), 1.62-1.36 (m, 6H). |
| 91 | 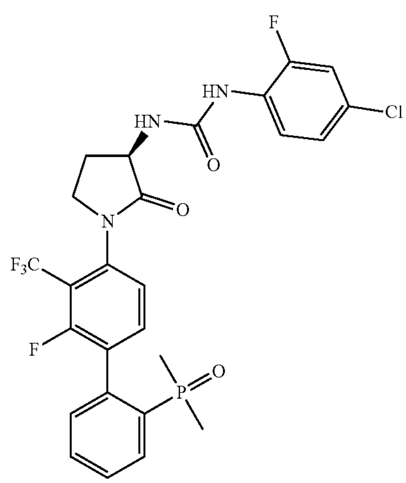 [SMILES: CP(C)(=O)c1ccccc1-c1ccc(N2CC[C@@H](NC(=O)Nc3ccc(Cl)cc3F)C2=O)c(C(F)(F)F)c1F] | 586.2 | Method C, RT = 1.778 min, 99.8% | ¹H NMR (400 MHz, DMSO-$d_6$) δ = 8.71-8.59 (m, 1H), 8.22-8.12 (m, 1H), 7.93-7.90 (m, 1H), 7.83-7.75 (m, 1H), 7.70-7.58 (m, 2H), 7.48-7.33 (m, 3H), 7.24-7.14 (m, 2H), 4.62 (d, J = 1.2 Hz, 1H), 3.96-3.84 (m, 1H), 3.81-3.71 (m, 1H), 2.65-2.58 (m, 1H), 2.10-2.04 (m, 1H), 1.67-1.33 (m, 6H). |
| 92 | 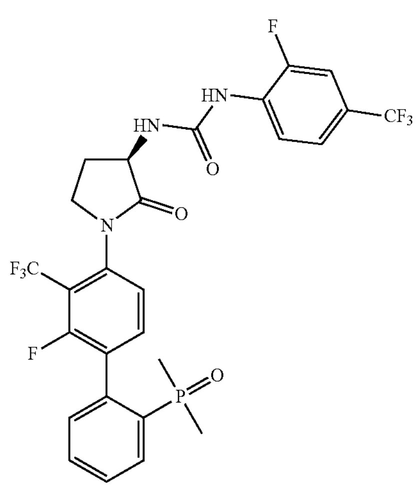 [SMILES: CP(C)(=O)c1ccccc1-c1ccc(N2CC[C@@H](NC(=O)Nc3ccc(C(F)(F)F)cc3F)C2=O)c(C(F)(F)F)c1F] | 620.2 | Method C, RT = 1.911 min, 100% | ¹H NMR (400 MHz, DMSO-$d_6$) δ = 9.00-8.89 (m, 1H), 8.47-8.37 (m, 1H), 7.95-7.86 (m, 1H), 7.83-7.74 (m, 1H), 7.71-7.60 (m, 3H), 7.55-7.48 (m, 1H), 7.45-7.36 (m, 2H), 7.35-7.32 (m, 1H), 4.75-4.43 (m, 1H), 3.96-3.84 (m, 1H), 3.81-3.71 (m, 1H), 2.66-2.58 (m, 1H), 2.10-2.04 (m, 1H), 1.60-1.48 (m, 6H). |

-continued

| Ex | Structure | LCMS (M + H)+ | HPLC Method, RT (min.) & Purity | ¹H NMR |
|---|---|---|---|---|
| 93 | 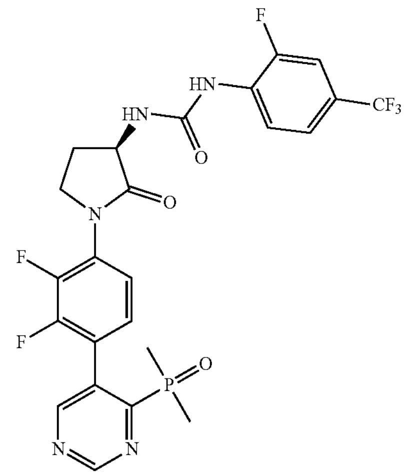 [SMILES: CP(C)(=O)c1ncncc1-c1ccc(N2CC[C@@H](NC(=O)Nc3ccc(C(F)(F)F)cc3F)C2=O)c(F)c1F] | 589.2 (M + NH₄)⁺ | Method C, RT = 1.532 min, 94.1% | ¹H NMR (400 MHz, DMSO-d₆) δ = 9.47 (s, 1H), 9.03-8.85 (m, 2H), 8.42 (t, J = 8.2 Hz, 1H), 7.67 (br. d., J = 11.5 Hz, 1H), 7.53 (s, 1H), 7.48-7.30 (m, 3H), 4.60 (td, J = 10.2, 8.0 Hz, 1H), 4.01-3.87 (m, 1H), 3.79 (br. t., J = 8.8 Hz, 1H), 2.65-2.55 (m, 1H), 2.18-2.04 (m, 1H), 1.69 (d, J = 13.7 Hz, 6H). |
| 94 | 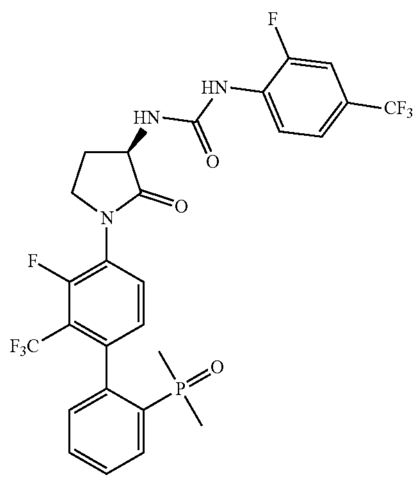 [SMILES: CP(C)(=O)c1ccccc1-c1ccc(N2CC[C@@H](NC(=O)Nc3ccc(C(F)(F)F)cc3F)C2=O)c(F)c1C(F)(F)F] | 620.2 | Method C, RT = 1.932 min, 100% | ¹H NMR (400 MHz, DMSO-d₆) δ = 8.95 (d, J = 3.2 Hz, 1H), 8.41 (t, J = 8.4 Hz, 1H), 7.90-7.80 (m, 1H), 7.76 (t, J = 7.9 Hz, 1H), 7.67 (dd, J = 1.8, 11.6 Hz, 1H), 7.63-7.55 (m, 2H), 7.52 (d, J = 9.0 Hz, 1H), 7.34 (d, J = 7.1 Hz, 1H), 7.29-7.19 (m, 2H), 4.64-4.55 (m, 1H), 3.96-3.87 (m, 1H), 3.83-3.74 (m, 1H), 2.99-2.87 (m, 1H), 2.64-2.56 (m, 1H), 2.16-2.06 (m, 1H), 1.60-1.48 (m, 6H). |
| 95 | 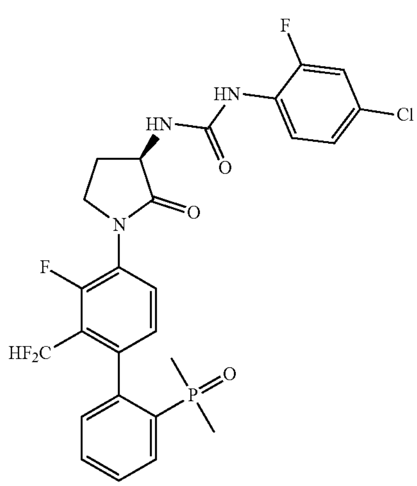 | 568.2 | Method C, RT = 1.608 min, 99% | ¹H NMR (400 MHz, DMSO-d₆) δ = 8.65 (br. s., 1H), 8.16 (t, J = 8.8 Hz, 1H), 7.98-7.87 (m, 1H), 7.74-7.57 (m, 3H), 7.43 (dd, J = 11.2, 2.4 Hz, 1H), 7.32-7.10 (m, 4H), 6.59 (t, J = 52.4 Hz, 1H), 4.60-4.50 (m, 1H), 3.95-3.85 (m, 1H), 3.81-3.71 (m, 1H), 2.62-2.55 (m, 1H), 2.17-2.03 (m, 1H), 1.50 (d, J = 13.2 Hz, 3H), 1.44 (d, J = 13.2 Hz, 3H). |

| Ex | Structure | LCMS (M + H)+ | HPLC Method, RT (min.) & Purity | ¹H NMR |
|---|---|---|---|---|
| 96 | 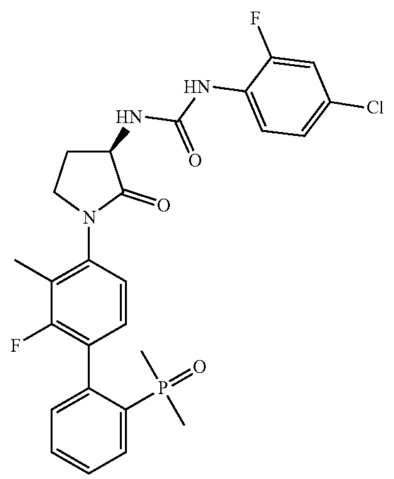 [SMILES: Cc1c(N2CC[C@@H](NC(=O)Nc3ccc(Cl)cc3F)C2=O)ccc(-c2ccccc2P(C)(C)=O)c1F] | 532.2 | Method C, RT = 1.813 min, 100% | ¹H NMR (400 MHz, DMSO-d$_6$) δ = 8.64 (d, J = 1.5 Hz, 1H), 8.16 (m, 1H), 8.04-7.92 (m, 1H), 7.69-7.54 (m, 2H), 7.43 (dd, J = 11.1, 2.3 Hz, 1H), 7.36-7.26 (m, 2H), 7.24-7.13 (m, 3H), 4.59-4.45 (m, 1H), 3.89-3.78 (m, 1H), 3.69-3.55 (m, 1H), 2.62-2.54 (m, 1H), 2.12 (m, 3H), 2.10-1.99 (m, 1H), 1.45 (br. d., J = 13.4 Hz, 3H), 1.36 (br. d., J = 13.4 Hz, 3H). |
| 97 | 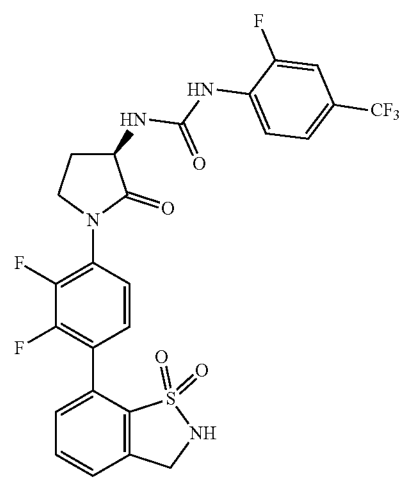 [SMILES: O=C(Nc1ccc(C(F)(F)F)cc1F)N[C@@H]1CCN(c2ccc(-c3cccc4c3S(=O)(=O)NC4)c(F)c2F)C1=O] | 585.2 | Method C, RT = 1.809 min, 100% | ¹H NMR (400 MHz, DMSO-d$_6$) δ = 8.95 (d, J = 2.7 Hz, 1H), 8.42 (t, J = 8.4 Hz, 1H), 8.02-7.84 (m, 1H), 7.81-7.74 (m, 1H), 7.70-7.62 (m, 2H), 7.57 (d, J = 7.6 Hz, 1H), 7.54-7.48 (m, 1H), 7.46 (dd, J = 6.8, 1.7 Hz, 1H), 7.42 (dd, J = 7.2, 1.7 Hz, 1H), 7.40-7.32 (m, 1H), 4.68-4.56 (m, 1H), 4.45 (s, 2H), 4.00-3.88 (m, 1H), 3.85-3.77 (m, 1H), 2.66-2.56 (m, 1H), 2.18-2.05 (m, 1H). |
| 98 | 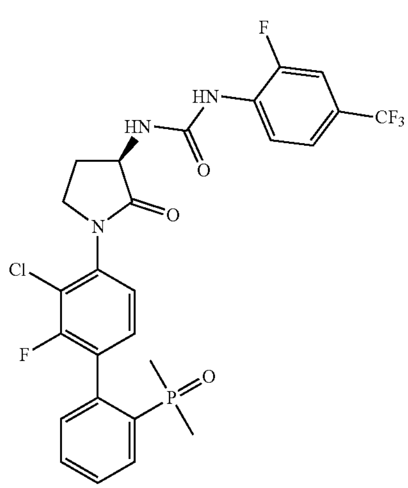 [SMILES: CP(C)(=O)c1ccccc1-c1ccc(N2CC[C@@H](NC(=O)Nc3ccc(C(F)(F)F)cc3F)C2=O)c(Cl)c1F] | 586.2 | Method C, RT = 1.764 min, 99.9% | ¹H NMR (400 MHz, DMSO-d$_6$) δ = 8.93 (br. s., 1H), 8.42 (m, 1H), 7.94-7.90 (m, 1H), 7.71-7.57 (m, 3H), 7.56-7.49 (m, 1H), 7.49-7.41 (m, 1H), 7.41-7.26 (m, 3H), 4.67-4.53 (m, 1H), 3.88-3.79 (m, 1H), 3.76-3.66 (m, 1H), 2.67-2.56 (m, 1H), 2.20-2.05 (m, 1H), 1.57-1.48 (m, 6H). |

-continued
| Ex | Structure | LCMS (M + H)+ | HPLC Method, RT (min.) & Purity | ¹H NMR |
|---|---|---|---|---|
| 99 | 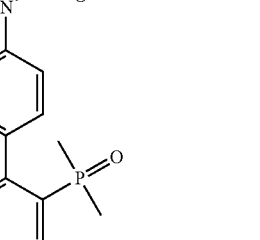 | 552.2 | Method C, RT = 1.595 min, 99.7% | ¹H NMR (400 MHz, DMSO-d$_6$) δ = 8.64 (br. s., 1H), 8.17 (t, J = 8.9 Hz, 1H), 7.95-7.90 (m, 1H), 7.71-7.57 (m, 2H), 7.50-7.30 (m, 4H), 7.25-7.09 (m, 2H), 4.65-4.49 (m, 1H), 3.82 (dt, J = 9.4, 6.4 Hz, 1H), 3.74-3.61 (m, 1H), 2.66-2.56 (m, 1H), 2.15-2.03 (m, 1H), 1.57-1.48 (m, 6H). |
| 100 | 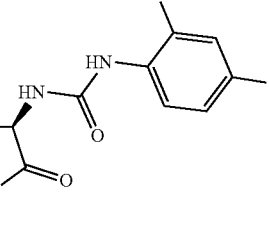 | 599.2 | Method C, RT = 1.857 min, 100% | ¹H NMR (400 MHz, DMSO-d$_6$) δ = 8.93 (d, J = 2.7 Hz, 1H), 8.85 (dd, J = 4.6, 1.2 Hz, 1H), 8.42 (m, 1H), 7.86-8.82 (m, 1H), 7.70-7.60 (m, 2H), 7.55-7.47 (m, 1H), 7.42-7.29 (m, 2H), 7.24-7.16 (m, 1H), 4.64-4.52 (m, 1H), 3.96-3.87 (m, 1H), 3.81-3.73 (m, 1H), 2.65-2.58 (m, 1H), 2.16-1.81 (m, 5H), 1.02-0.85 (m, 6H). |
| 101 | 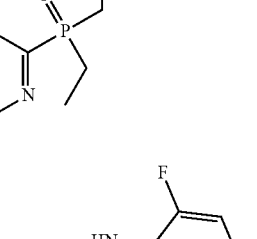 | 583.1 (M + NH$_4$)⁺ | Method C, RT = 1.746 min, 100% | ¹H NMR (400 MHz, DMSO-d$_6$) δ = 8.69-8.56 (m, 1H), 8.15 (t, J = 8.9 Hz, 1H), 8.04-7.91 (m, 1H), 7.76-7.59 (m, 2H), 7.49-7.32 (m, 3H), 7.29-7.10 (m, 3H), 4.62-4.51 (m, 1H), 3.97-3.61 (m, 4H), 2.57-2.52 (m, 1H), 2.14-2.01 (m, 1H), 1.44 (d, J = 14.4 Hz, 3H), 1.12 (t, J = 7.1 Hz, 3H). |

-continued

| Ex | Structure | LCMS (M + H)+ | HPLC Method, RT (min.) & Purity | ¹H NMR |
|---|---|---|---|---|
| 102 | 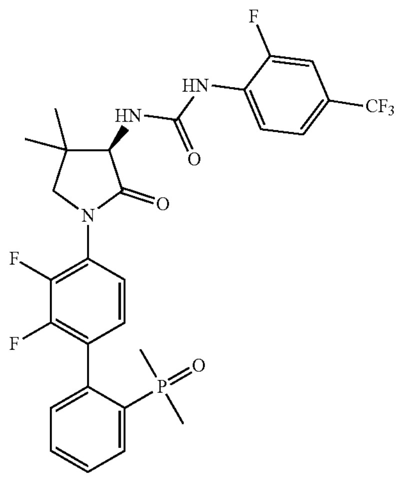 [SMILES: CC1(C)CN(c2ccc(-c3ccccc3P(C)(C)=O)c(F)c2F)C(=O)[C@@H]1NC(=O)Nc1ccc(C(F)(F)F)cc1F] | 598.2 | Method C, RT = 1.965 min, 100% | ¹H NMR (400 MHz, DMSO-$d_6$) δ = 8.96 (d, J = 2.7 Hz, 1H), 8.46 (t, J = 8.3 Hz, 1H), 7.97-7.86 (m, 1H), 7.72-7.57 (m, 3H), 7.53 (d, J = 8.8 Hz, 1H), 7.42-7.30 (m, 2H), 7.30-7.22 (m, 2H), 4.65 (d, J = 9.0 Hz, 1H), 3.88 (br. d., J = 9.3 Hz, 1H), 3.45 (br. d., J = 9.3 Hz, 1H), 1.53 (d, J = 13.2 Hz, 6H), 1.22 (s, 3H), 1.06 (s, 3H). |
| 103 | 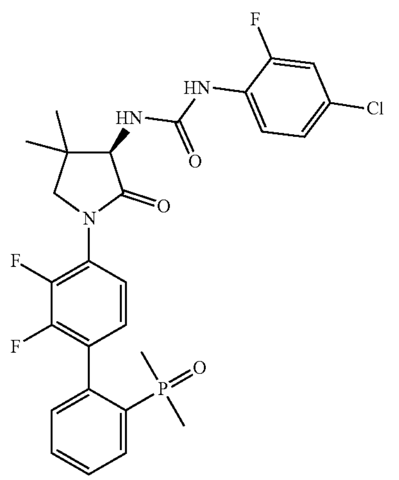 [SMILES: CC1(C)CN(c2ccc(-c3ccccc3P(C)(C)=O)c(F)c2F)C(=O)[C@@H]1NC(=O)Nc1ccc(Cl)cc1F] | 581.2 (M + NH$_4$)+ | Method C, RT = 1.965 min, 100% | ¹H NMR (400 MHz, DMSO-$d_6$) δ = 8.68 (d, J = 1.5 Hz, 1H), 8.22 (t, J = 9.0 Hz, 1H), 7.97-7.86 (m, 1H), 7.70-7.56 (m, 2H), 7.45 (dd, J = 11.2, 2.4 Hz, 1H), 7.41-7.29 (m, 2H), 7.29-7.17 (m, 2H), 7.12 (d, J = 9.0 Hz, 1H), 4.62 (d, J = 9.0 Hz, 1H), 3.86 (br. d., J = 9.3 Hz, 1H), 3.45 (br. d., J = 9.3 Hz, 1H), 1.54 (d, J = 13.2 Hz, 6H), 1.21 (s, 3H), 1.05 (s, 3H). |
| 104 | 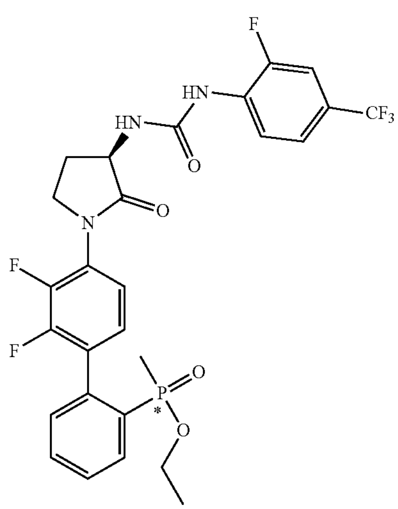 [SMILES: CCOP(C)(=O)c1ccccc1-c1ccc(N2CC[C@@H](NC(=O)Nc3ccc(C(F)(F)F)cc3F)C2=O)c(F)c1F] | 600.2 | Method C, RT = 1.871 min, 100% | ¹H NMR (400 MHz, DMSO-$d_6$) δ = 8.98-8.86 (m, 1H), 8.41 (t, J = 8.68 Hz, 1H), 8.02-7.92 (m, 1H), 7.77-7.60 (m, 3H), 7.56-7.48 (m, 1H), 7.46-7.30 (m, 3H), 7.28-7.18 (m, 1H), 4.65-4.51 (m, 1H), 3.98-3.81 (m, 2H), 3.81-3.73 (m, 1H), 3.73-3.61 (m, 1H), 2.65-2.54 (m, 1H), 2.17-2.02 (m, 1H), 1.44 (d, J = 14.67 Hz, 3H), 1.12 (t, J = 7.1 Hz, 3H). |

-continued

| Ex | Structure | LCMS (M + H)+ | HPLC Method, RT (min.) & Purity | 1H NMR |
|---|---|---|---|---|
| 105 | 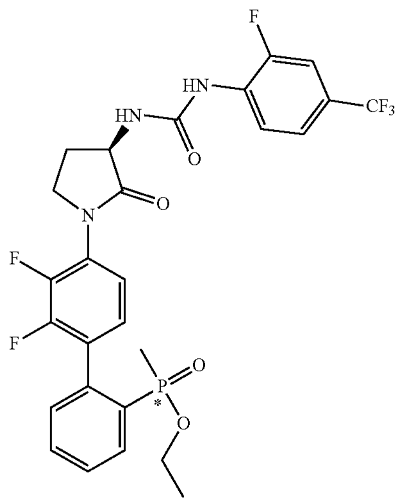 [SMILES: CCOP(C)(=O)c1ccccc1-c1ccc(N2CC[C@@H](NC(=O)Nc3ccc(C(F)(F)F)cc3F)C2=O)c(F)c1F] | 600.2 | Method C, RT = 1.871 min, 100% | 1H NMR (400 MHz, DMSO-d6) δ = 9.02-8.90 (m, 1H), 8.41 (t, J = 8.3 Hz, 1H), 8.05-7.92 (m, 1H), 7.76-7.60 (m, 3H), 7.51 (dd, J = 8.7, 1.1 Hz, 1H), 7.46-7.31 (m, 3H), 7.28-7.15 (m, 1H), 4.65-4.53 (m, 1H), 3.97-3.74 (m, 3H), 3.74-3.60 (m, 1H), 2.65-2.56 (m, 1H), 2.18-2.02 (m, 1H), 1.45 (d, J = 14.43 Hz, 3H), 1.12 (t, J = 7.1 Hz, 3H). |
| 106 | 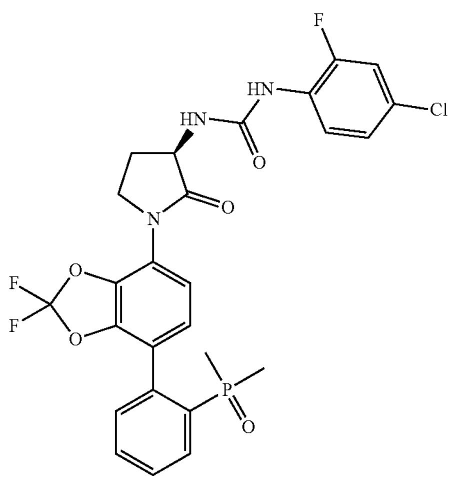 [SMILES: CP(C)(=O)c1ccccc1-c1ccc(N2CC[C@@H](NC(=O)Nc3ccc(Cl)cc3F)C2=O)c2c1OC(F)(F)O2] | 580.1 | Method C, RT = 1.763 min, 94.7% | 1H NMR (400 MHz, DMSO-d6) δ = 8.65 (d, J = 2.5 Hz, 1 H) 8.15 (t, J = 8.9 Hz, 1 H), 7.96-7.88 (m, 1 H), 7.67-7.64 (m, 2 H), 7.51 (d, J = 8.6 Hz, 1 H), 7.37-7.47 (m, 2 H), 7.27 (d, J = 8.8 Hz, 1 H), 7.16-7.23 (m, 2 H), 4.47-4.64 (m, 1 H), 3.90-4.01 (m, 1H), 3.82-3.90 (m, 1 H), 2.54-2.62 (m, 1 H), 2.01-2.15 (m, 1 H), 1.53 (d, J = 13.2 Hz, 6 H). |
| 107 | 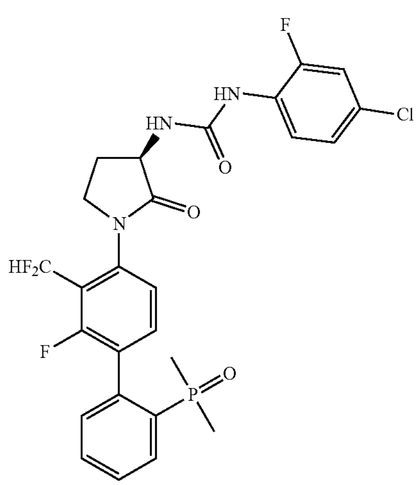 | 568.1 | Method C, RT = 1.662 min, 100% | 1H NMR (400 MHz, DMSO-d6) δ = 8.74 (d, J = 1.71 Hz, 1 H), 8.11 (t, J = 8.93 Hz, 1 H), 7.89-8.01 (m, 1 H), 7.57-7.71 (m, 3 H), 7.40-7.40 (m, 1 H), 7.34-7.48 (m, 1 H), 7.32 (d, J = 8.31 Hz, 1 H), 7.25-7.14 (m, 2 H), 7.04 (t, J = 52.4 Hz, 1H), 4.41-4.55 (m, 1 H), 3.89-4.01 (m, 1 H), 3.64-3.71 (m, 1 H), 2.56-2.52 (m, 1 H), 2.18-2.31 (m, 1 H), 1.30-1.63 (m, 6 H). |

-continued

| Ex | Structure | LCMS (M + H)+ | HPLC Method, RT (min.) & Purity | ¹H NMR |
|---|---|---|---|---|
| 108 | 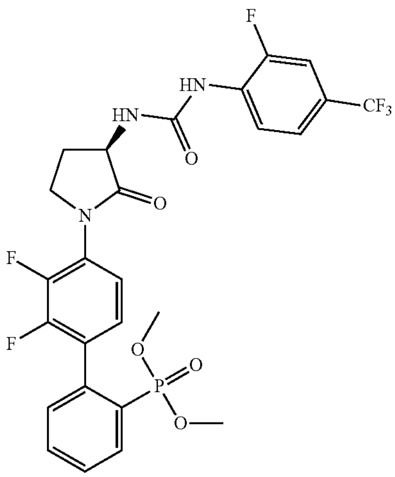 [SMILES: COP(=O)(OC)c1ccccc1-c1ccc(N2CC[C@@H](NC(=O)Nc3ccc(C(F)(F)F)cc3F)C2=O)c(F)c1F] | 602.1 | Method C, RT = 1.892 min, 100% | ¹H NMR (400 MHz, DMSO-d$_6$) δ = 8.93 (d, J = 2.5 Hz, 1 H), 8.41 (t, J = 8.4 Hz, 1 H), 8.0-7.87 (m, 1 H), 7.77-7.71 (m, 1 H), 7.69-7.59 (m, 2 H), 7.55-7.49 (m, 1 H), 7.48-7.42 (m, 1 H), 7.41-7.27 (m, 2 H), 7.23-7.13 (m, 1 H), 4.65-4.54 (m, 1 H), 3.97-3.86 (m, 1 H), 3.82-3.71 (m, 1 H), 3.51 (s, 3H), 3.49 (s, 3H), 2.65-2.56 (m, 1 H), 2.18-2.02 (m, 1 H). |
| 109 | 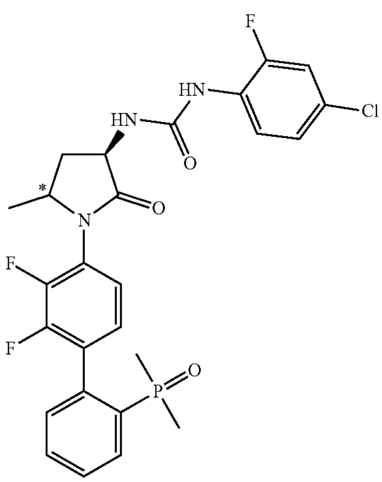 [SMILES: CC1C[C@@H](NC(=O)Nc2ccc(Cl)cc2F)C(=O)N1c1ccc(-c2ccccc2P(C)(C)=O)c(F)c1F] | 550.2 | Method C, RT = 1.650 min, 100% | ¹H NMR (400 MHz, DMSO-d$_6$) δ = 8.63 (d, J = 2.0 Hz, 1 H), 8.14 (t, J = 8.9 Hz, 1 H), 7.99-7.84 (m, 1 H), 7.72-7.55 (m, 2 H), 7.37-7.50 (m, 2 H), 7.35-7.25 (m, 2 H), 7.23-7.17 (m, 1 H), 7.14 (d, J = 7.1 Hz, 1 H), 4.70-4.58 (m, 1 H), 4.36-4.23 (m, 1 H), 2.36-2.25 (m, 2 H), 1.46 (d, J = 12.4 Hz, 6H), 1.19 (d, J = 6.4 Hz, 3 H). |
| 110 | 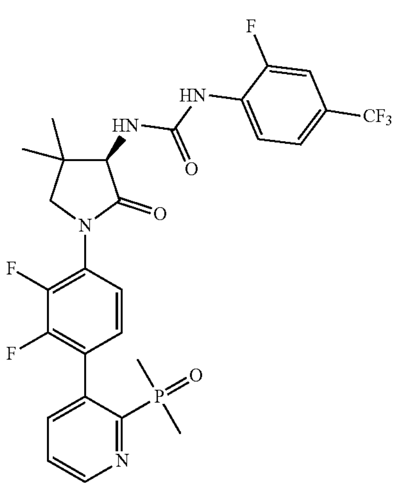 | 599.2 | Method C, RT = 1.851 min, 100% | ¹H NMR (400 MHz, DMSO-d$_6$) δ = 8.96 (d, J = 3.18 Hz, 1 H), 8.84 (m, 1 H), 8.46 (t, J = 8.2 Hz, 1 H), 7.87 (m, 1H), 7.63-7.72 (m, 2 H), 7.52 (d, J = 9.5 Hz, 1 H), 7.19-7.39 (m, 3 H), 4.65 (d, J = 9.1 Hz, 1 H), 3.88 (d, J = 9.2 Hz, 1 H), 3.45 (d, J = 9.2 Hz, 1 H), 1.63 (d, J = 13.2 Hz, 6H), 1.23 (s, 3 H), 1.07 (s, 3 H). |

-continued

| Ex | Structure | LCMS (M + H)+ | HPLC Method, RT (min.) & Purity | ¹H NMR |
|---|---|---|---|---|
| 111 | 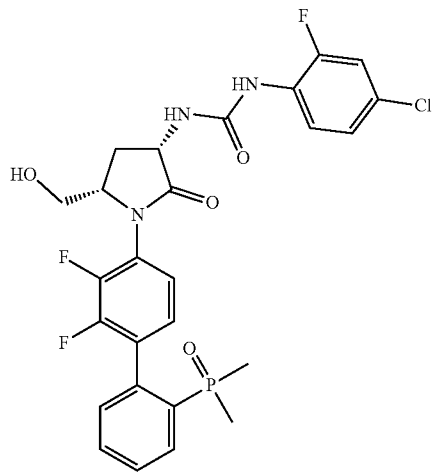 [SMILES: CP(C)(=O)c1ccccc1-c1ccc(N2C(=O)[C@@H](NC(=O)Nc3ccc(Cl)cc3F)C[C@H]2CO)c(F)c1F] | 566.2 | Method C, RT = 1.404 min, 100% | ¹H NMR (400 MHz, DMSO-d$_6$) δ = 8.63 (s, 1H), 8.17 (t, J = 8.8 Hz, 1H), 8.00-7.88 (m, 1H), 7.70-7.58 (m, 2H), 7.49-7.36 (m, 2H), 7.33-7.13 (m, 4H), 4.93 (t, J = 5.0 Hz, 1H), 4.68-4.56 (m, 1H), 4.25-4.12 (m, 1H), 3.44 (br. t., J = 4.0 Hz, 2H), 2.67-2.61 (m, 1H), 1.98-1.85 (m, 1H), 1.64-1.42 (m, 6H). |
| 112 | 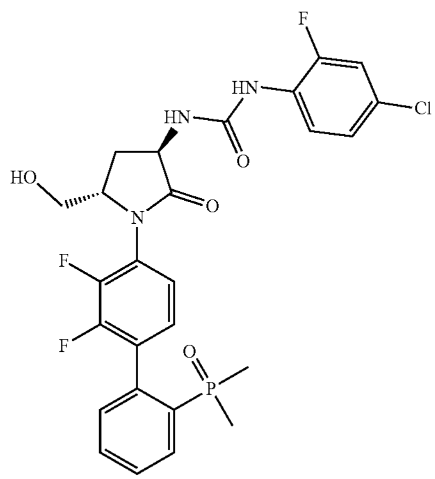 [SMILES: CP(C)(=O)c1ccccc1-c1ccc(N2C(=O)[C@H](NC(=O)Nc3ccc(Cl)cc3F)C[C@H]2CO)c(F)c1F] | 566.2 | Method C, RT = 1.425 min, 100% | ¹H NMR (400 MHz, DMSO-d$_6$) δ = 8.61 (s, 1H), 8.14 (t, J = 8.9 Hz, 1H), 7.98-7.87 (m, 1H), 7.71-7.56 (m, 2H), 7.46-7.36 (m, 2H), 7.36-7.24 (m, 2H), 7.22-7.15 (m, 1H), 7.09 (d, J = 7.6 Hz, 1H), 5.15-5.05 (m, 1H), 4.76-4.63 (m, 1H), 4.24-4.11 (m, 1H), 3.47 (br. d., J = 3.9 Hz, 2H), 2.53 (br. s., 1H), 2.29-2.20 (m, 1H), 1.60-1.41 (m, 6H). |
| 113 | 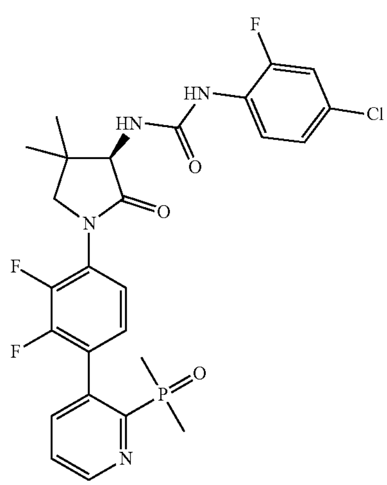 | 565.2 | Method C, RT = 1.719 min, 100% | ¹H NMR (400 MHz, DMSO-d$_6$) δ = 8.84 (d, J = 4.9 Hz, 1 H), 8.68 (d, J = 2.5 Hz, 1 H), 8.22 (t, J = 8.9 Hz, 1 H), 7.87 (ddd, J = 7.8, 4.4, 1.5 Hz, 1 H), 7.67 (ddd, J = 7.8, 4.9, 2.5 Hz, 1 H), 7.44 (dd, J = 11.3, 2.5 Hz, 1 H), 7.26-7.38 (m, 2 H), 7.21 (ddd, J = 8.9, 2.5, 1.1 Hz, 1 H), 7.00-7.16 (m, 1 H), 4.62 (d, J = 9.1 Hz, 1 H), 3.86 (d, J = 9.1 Hz, 1 H), 3.44 (d, J = 9.1 Hz, 1 H), 1.63 (d, J = 13.7 Hz, 6 H), 1.19-1.28 (m, 3 H), 1.05 (s, 3 H). |

-continued

| Ex | Structure | LCMS (M + H)+ | HPLC Method, RT (min.) & Purity | ¹H NMR |
|---|---|---|---|---|
| 114 | 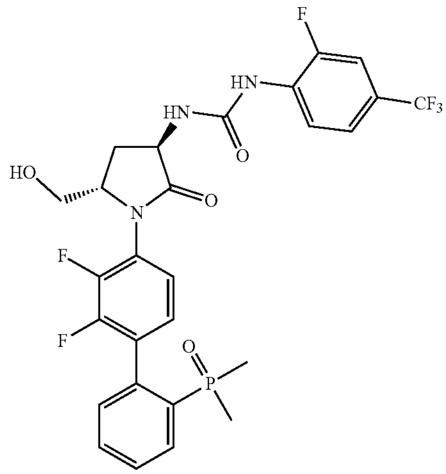 [SMILES: CP(C)(=O)c1ccccc1-c1ccc(N2C(=O)[C@H](NC(=O)Nc3ccc(C(F)(F)F)cc3F)C[C@H]2CO)c(F)c1F] | 600.2 | Method D, RT = 1.577 min, 100% | ¹H NMR (400 MHz, DMSO-d$_6$) δ = 9.06-8.51 (br. s., 1H), 8.45-8.36 (m, 1 H), 8.00-7.87 (m, 1 H), 7.71-7.57 (m, 3 H), 7.51 (dd, J = 9.17, 1.10 Hz, 1 H), 7.44-7.11 (m, 4 H), 4.78-4.61 (m, 1 H), 4.26-4.21 (m, 1 H), 3.50-3.40 (m, 3 H), 2.61-2.53 (m, 1 H), 2.33-2.22 (m, 1 H), 1.44-1.55 (m, 6 H). |
| 115 | 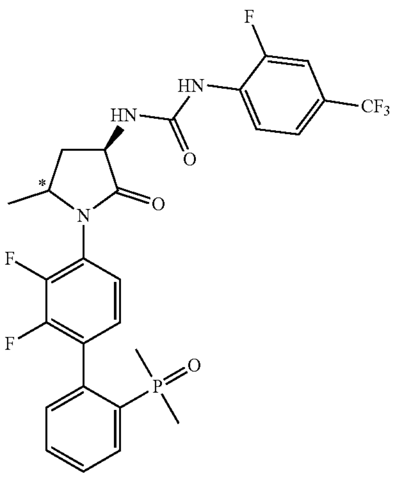 [SMILES: CC1C[C@@H](NC(=O)Nc2ccc(C(F)(F)F)cc2F)C(=O)N1c1ccc(-c2ccccc2P(C)(C)=O)c(F)c1F] | 584.2 | Method D, RT = 1.805 min, 100% | ¹H NMR (400 MHz, DMSO-d$_6$) δ = 8.97-8.85 (m, 1 H), 8.46-8.34 (m, 1 H), 7.99-7.89 (m, 1 H), 7.70-7.57 (m, 3 H), 7.52 (br. d., J = 8.6 Hz, 1 H), 7.46-7.17 (m, 4 H), 4.71-4.57 (m, 1 H), 4.34-4.15 (m, 1 H), 2.37-2.30 (m, 1 H), 1.75-1.62 (m, 1 H), 1.59-1.39 (m, 6 H), 1.19 (d, J = 6.4 Hz, 3 H). |
| 116 | 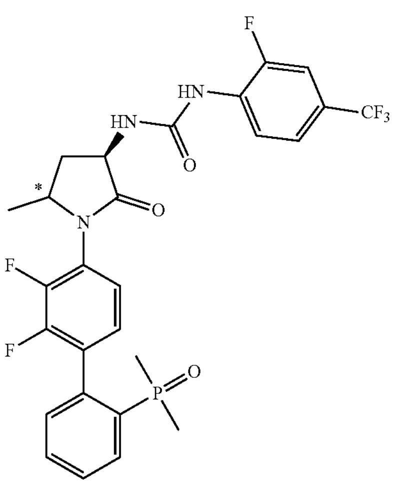 [SMILES: CC1C[C@@H](NC(=O)Nc2ccc(C(F)(F)F)cc2F)C(=O)N1c1ccc(-c2ccccc2P(C)(C)=O)c(F)c1F] | 584.2 | Method D, RT = 1.802 min, 100% | ¹H NMR (400 MHz, DMSO-d$_6$) δ = 8.92 (d, J = 2.7 Hz, 1 H), 8.40 (t, J = 8.3 Hz, 1 H), 7.97-7.89 (m, 1 H), 7.71-7.58 (m, 3 H), 7.51 (d, J = 8.8 Hz, 1 H), 7.40 (m, 1 H), 7.36-7.25 (m, 3 H), 4.66 (td, J = 9.2, 7.3 Hz, 1 H), 4.35-4.24 (m, 1 H), 2.38-2.24 (m, 2 H), 1.63-1.41 (m, 6 H), 1.20 (d, J = 6.4 Hz, 3 H). |

| Ex | Structure | LCMS (M + H)+ | HPLC Method, RT (min.) & Purity | ¹H NMR |
|---|---|---|---|---|
| 117 | 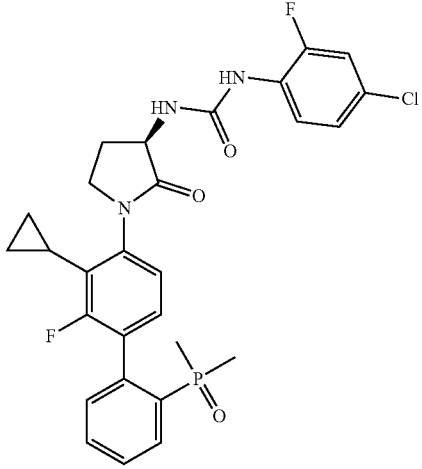 [SMILES: CP(C)(=O)c1ccccc1-c1ccc(N2CC[C@@H](NC(=O)Nc3ccc(Cl)cc3F)C2=O)c(C2CC2)c1F] | 558.2 | Method D, RT = 1.711 min, 99.4% | ¹H NMR (400 MHz, DMSO-d$_6$) δ = 8.65 (br. s., 1 H), 8.18 (t, J = 8.9 Hz, 1 H), 7.96 (m, 1 H), 7.69-7.53 (m, 2 H), 7.43 (dd, J = 12.5, 2.5 Hz, 1 H), 7.37-7.26 (m, 2 H), 7.25-7.10 (m, 3 H), 4.57 (dt, J = 10.3, 8.1 Hz, 1 H), 3.95-3.65 (m, 2 H), 2.66-2.55 (m, 1 H), 2.14-2.03 (m, 1 H), 1.80-1.69 (m, 1 H), 1.51-1.30 (m, 6 H), 0.98-0.83 (m, 2 H), 0.67-0.43 (m, 2 H). |
| 118 | 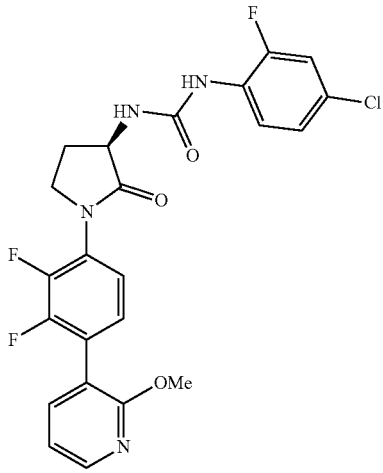 [SMILES: COc1ncccc1-c1ccc(N2CC[C@@H](NC(=O)Nc3ccc(Cl)cc3F)C2=O)c(F)c1F] | 491 | Method C, RT = 1.921 min, 99.3% | ¹H NMR (400 MHz, DMSO-d$_6$) δ = 8.63 (d, J = 2.1 Hz, 1 H), 8.29 (dd, J = 5.0, 2.1 Hz, 1 H), 8.15 (t, J = 8.8 Hz, 1 H), 7.78 (dd, J = 7.3, 2.1 Hz, 1 H), 7.47-7.36 (m, 2 H), 7.35-7.28 (m, 1 H), 7.25-7.05 (m, 3 H), 4.62-4.48 (m, 1 H), 3.95-3.84 (m, 1 H), 3.89 (s, 3H), 3.83-3.71 (m, 1 H), 2.63-2.52 (m, 1 H), 2.14-2.03 (m, 1H). |
| 119 | 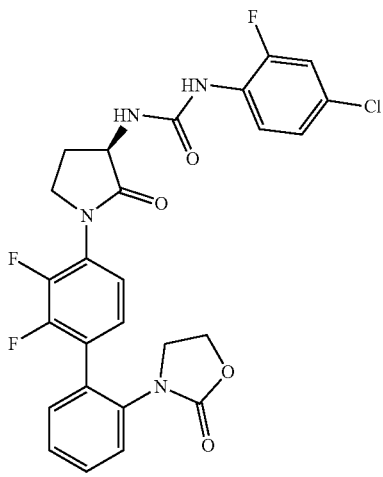 [SMILES: O=C(Nc1ccc(Cl)cc1F)N[C@@H]1CCN(c2ccc(-c3ccccc3N3CCOC3=O)c(F)c2F)C1=O] | 545.1 | Method C, RT = 1.737 min, 100% | ¹H NMR (400 MHz, DMSO-d$_6$) δ = 8.64 (d, J = 2.0 Hz, 1H), 8.19-8.05 (m, 1H), 7.63-7.52 (m, 2H), 7.50-7.35 (m, 4H), 7.27-7.13 (m, 3H), 4.55 (td, J = 10.5, 8.0 Hz, 1H), 4.30 (t, J = 7.9 Hz, 2H), 3.96-3.81 (m, 3H), 3.81-3.72 (m, 1H), 2.61-2.54 (m, 1H), 2.13-2.02 (m, 1H). |

| Ex | Structure | LCMS (M + H)+ | HPLC Method, RT (min.) & Purity | ¹H NMR |
|---|---|---|---|---|
| 120 | 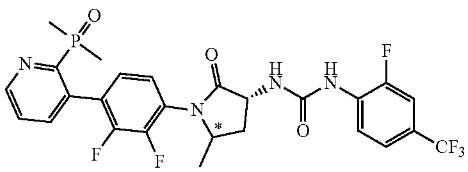 [SMILES: CC1C[C@@H](NC(=O)Nc2ccc(C(F)(F)F)cc2F)C(=O)N1c1ccc(-c2cccnc2P(C)(C)=O)c(F)c1F] | 585.0 | Method E, RT = 2.500 min, 99.9% | ¹H NMR (400 MHz, DMSO-d$_6$) δ = 8.93 (d, J = 2.7 Hz, 1H), 8.85 (d, J = 4.7 Hz, 1H), 8.40 (t, J = 8.2 Hz, 1H), 7.90 (m, 1H), 7.72-7.63 (m, 2H), 7.51 (m, 1H), 7.37-7.28 (m, 3H), 4.67 (m, 1H), 4.30 (m, 1H), 2.46-2.23 (m, 2H), 1.62 (d, J = 13.2 Hz, 6H), 1.19 (d, J = 5.2 Hz, 3H). |
| 121 | 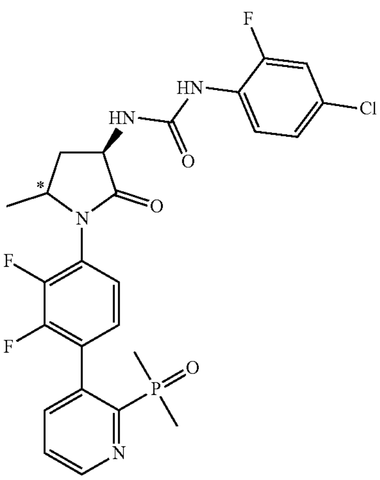 [SMILES: CC1C[C@@H](NC(=O)Nc2ccc(Cl)cc2F)C(=O)N1c1ccc(-c2cccnc2P(C)(C)=O)c(F)c1F] | 551.2 | Method C, RT = 1.596 min, 90.1% | ¹H NMR (400 MHz, DMSO-d$_6$) δ = 8.85 (d, J = 4.9 Hz, 1H), 8.69-8.60 (m, 1H), 8.20-8.09 (m, 1H), 7.91 (dd, J = 6.7, 4.9 Hz, 1H), 7.68 (m, 1H), 7.43 (dd, J = 11.0, 2.5 Hz, 1H), 7.37-7.30 (m, 1H), 7.29-7.18 (m, 3H), 4.69-4.50 (m, 1H), 4.34-4.10 (m, 1H), 2.86-2.76 (m, 1H), 1.65-1.62 (m, 1H), 1.63 (d, J = 13.4 Hz, 3H), 1.62 (d, J = 13.4 Hz, 3H), 1.12 (d, J = 6.1 Hz, 3H). |
| 122 | 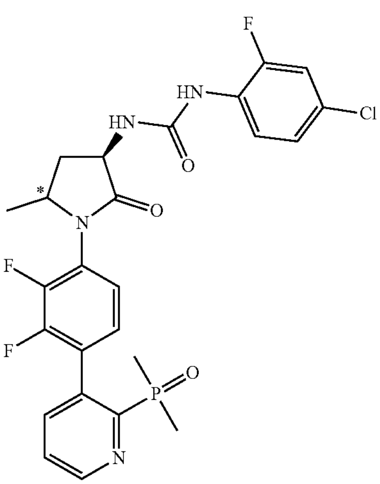 [SMILES: CC1C[C@@H](NC(=O)Nc2ccc(Cl)cc2F)C(=O)N1c1ccc(-c2cccnc2P(C)(C)=O)c(F)c1F] | 551.2 | Method C, RT = 1.592 min, 92.5% | ¹H NMR (400 MHz, DMSO-d$_6$) δ = 8.85 (d, J = 4.2 Hz, 1 H), 8.65 (s, 1 H), 8.15 (t, J = 8.9 Hz, 1 H), 7.90 (m, 1 H), 7.68 (m, 1 H), 7.42 (dd, J = 11.1, 2.3 Hz, 1 H), 7.36-7.31 (m, 2 H), 7.22-7.14 (m, 2 H), 4.70-4.59 (m, 1 H), 4.34-4.26 (m, 1 H), 2.37-2.27 (m, 2 H), 1.62 (d, J = 13.5 Hz, 6 H), 1.12 (d, J = 6.1 Hz, 3H). |

| Ex | Structure | LCMS (M + H)+ | HPLC Method, RT (min.) & Purity | ¹H NMR |
|---|---|---|---|---|
| 123 | 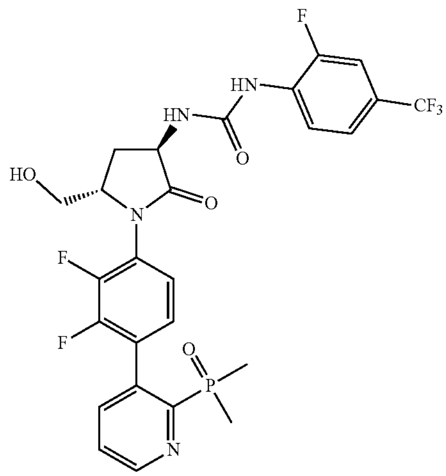 [SMILES: CP(C)(=O)c1ncccc1-c1ccc(N2C(=O)[C@H](NC(=O)Nc3ccc(C(F)(F)F)cc3F)C[C@H]2CO)c(F)c1F] | 618.2 (M + NH₄)⁺ | Method C, RT = 1.502 min, 100% | ¹H NMR (400 MHz, DMSO-d₆) δ = 8.91 (d, J = 2.7 Hz, 1H), 8.85 (d, J = 4.6 Hz, 1H), 8.41 (t, J = 8.6 Hz, 1H), 7.89 (dd, J = 7.5, 4.0 Hz, 1H), 7.70-7.63 (m, 2H), 7.51 (br. d., J = 8.6 Hz, 1H), 7.34 (t, J = 6.4 Hz, 2H), 7.25 (d, J = 7.3 Hz, 1H), 5.12 (t, J = 4.9 Hz, 1H), 4.77-4.66 (m, 1H), 4.19 (br. d., J = 8.3 Hz, 1H), 3.49-3.43 (m, 2H), 2.62-2.53 (m, 1H), 2.33-2.22 (m, 1H), 1.63 (d, J = 13.4 Hz, 3H), 1.62 (d, J = 13.4 Hz, 3H). |
| 124 | 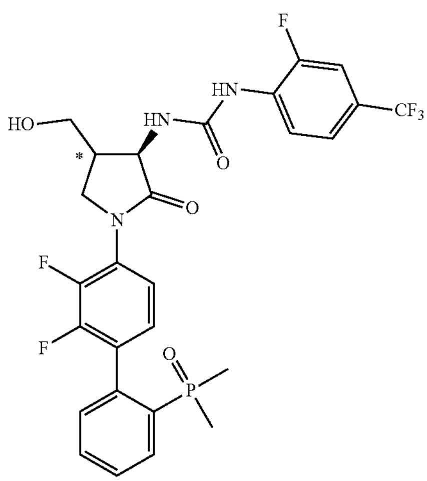 [SMILES: CP(C)(=O)c1ccccc1-c1ccc(N2CC(CO)[C@@H](NC(=O)Nc3ccc(C(F)(F)F)cc3F)C2=O)c(F)c1F] | 600.2 | Method C, RT = 1.577 min, 100% | ¹H NMR (400 MHz, DMSO-d₆) δ = 9.19 (br. s., 1H), 8.45 (t, J = 8.4 Hz, 1H), 7.96-7.86 (m, 1H), 7.70-7.58 (m, 3H), 7.52 (d, J = 8.4 Hz, 1H), 7.42-7.33 (m, 2H), 7.31-7.22 (m, 2H), 4.87 (t, J = 8.1 Hz, 1H), 4.18-4.07 (m, 1H), 3.71 (br. d., J = 8.8 Hz, 1H), 3.64-3.58 (m, 1H), 3.4-3.2 (m, 2H), 2.85-2.72 (m, 1H), 1.52 (br. d., J = 13.2 Hz, 6H). |
| 125 | 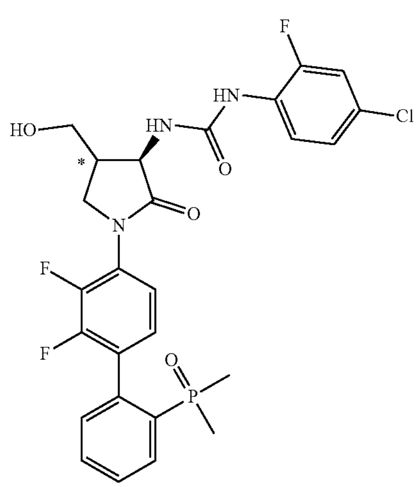 [SMILES: CP(C)(=O)c1ccccc1-c1ccc(N2CC(CO)[C@@H](NC(=O)Nc3ccc(Cl)cc3F)C2=O)c(F)c1F] | 583.2 (M + NH₄)⁺ | Method D, RT = 1.442 min, 100% | ¹H NMR (400 MHz, DMSO-d₆) δ = 8.70-8.63 (m, 1H), 8.13 (t, J = 8.6 Hz, 1H), 7.97-7.86 (m, 1H), 7.71-7.58 (m, 2H), 7.45-7.35 (m, 3H), 7.29-7.17 (m, 3H), 4.37 (dd, J = 10.0, 8.3 Hz, 1H), 3.88-3.81 (m, 1H), 3.76-3.66 (m, 1H), 3.61 (dd, J = 11.0, 6.6 Hz, 2H), 2.66-2.56 (m, 1H), 1.53 (br. d., J = 13.2 Hz, 6H). |

-continued

| Ex | Structure | LCMS (M + H)+ | HPLC Method, RT (min.) & Purity | ¹H NMR |
|---|---|---|---|---|
| 126 | 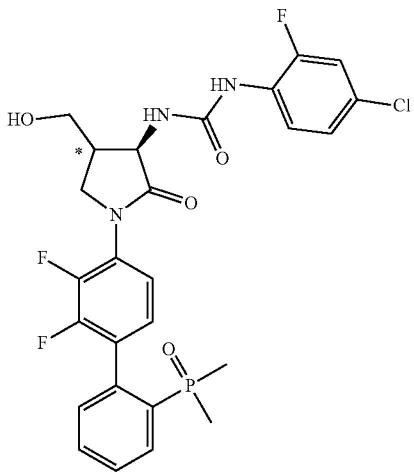 [SMILES: CP(C)(=O)c1ccccc1-c1ccc(N2CC(CO)[C@@H](NC(=O)Nc3ccc(Cl)cc3F)C2=O)c(F)c1F] | 583.2 (M + NH₄)⁺ | Method D, RT = 1.482 min, 94.5% | ¹H NMR (400 MHz, DMSO-d₆) δ = 8.90 (s, 1H), 8.19 (t, J = 8.9 Hz, 1H), 7.98-7.86 (m, 1H), 7.69-7.59 (m, 2H), 7.43 (dd, J = 11.2, 2.4 Hz, 1H), 7.40-7.34 (m, 2H), 7.30-7.24 (m, 1H), 7.23-7.18 (m, 1H), 7.12 (d, J = 7.8 Hz, 1H), 4.85 (t, J = 8.1 Hz, 1H), 4.17-4.07 (m, 1H), 3.71 (br. d., J = 9.5 Hz, 1H), 3.60 (br. dd., J = 9.5, 3.2 Hz, 2H), 2.76-2.70 (m, 1H), 1.52 (br. d., J = 13.2 Hz, 6H). |
| 127 | 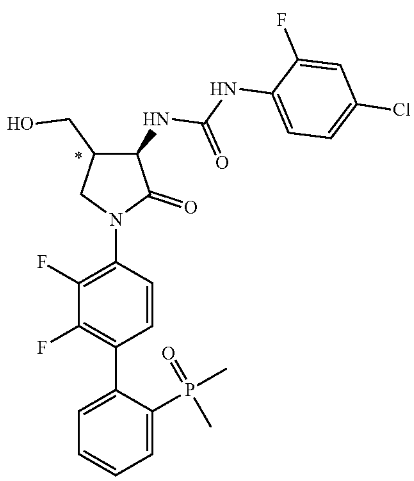 [SMILES: CP(C)(=O)c1ccccc1-c1ccc(N2CC(CO)[C@@H](NC(=O)Nc3ccc(Cl)cc3F)C2=O)c(F)c1F] | 583.2 (M + NH₄)⁺ | Method D, RT = 1.490 min, 96.5% | ¹H NMR (400 MHz, DMSO-d₆) δ = 8.91 (s, 1H), 8.20 (t, J = 9.1 Hz, 1H), 7.98-7.86 (m, 1H), 7.71-7.61 (m, 2H), 7.43 (dd, J = 11.0, 2.5 Hz, 1H), 7.40-7.34 (m, 2H), 7.30-7.24 (m, 1H), 7.21-7.16 (m, 1H), 7.13 (d, J = 8.0 Hz, 1H), 4.86 (t, J = 8.2 Hz, 1H), 4.16-4.08 (m, 1H), 3.72 (br. d., J = 9.3 Hz, 1H), 3.60 (br. dd., J = 9.3, 3.2 Hz, 2H), 2.76-2.71 (m, 1H), 1.53 (br. d., J = 13.2 Hz, 6H). |
| 128 | 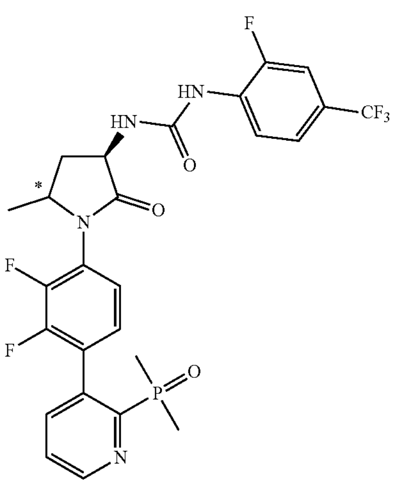 [SMILES: CC1C[C@@H](NC(=O)Nc2ccc(C(F)(F)F)cc2F)C(=O)N1c1ccc(-c2cccnc2P(C)(C)=O)c(F)c1F] | 585.0 | Method E, RT = 2.571 min, 99.7% | ¹H NMR (400 MHz, DMSO-d₆) δ = 8.93 (br. s., 1H), 8.84 (d, J = 3.9 Hz, 1H), 8.41 (t, J = 8.1 Hz, 1H), 7.93-7.88 (m, 1H), 7.74-7.61 (m, 2H), 7.51 (br. d., J = 8.3 Hz, 1H), 7.44-7.21 (m, 3H), 4.70-4.52 (m, 1H), 4.22 (br. d., J = 9.5 Hz, 1H), 2.85-2.78 (m, 1H), 2.57-2.52 (m, 1H), 1.63 (d, J = 13.4 Hz, 3H), 1.61 (d, J = 13.4 Hz, 3H), 1.13 (d, J = 6.4 Hz, 3H). |

| Ex | Structure | LCMS (M + H)+ | HPLC Method, RT (min.) & Purity | ¹H NMR |
|---|---|---|---|---|
| 129 | 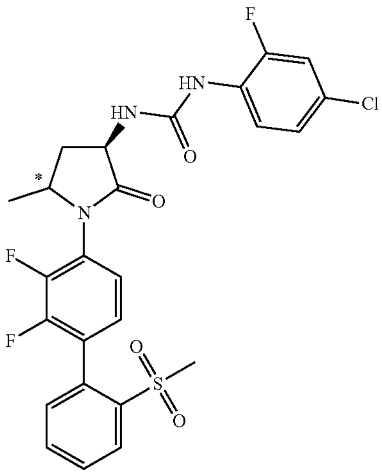 [SMILES: CC1C[C@@H](NC(=O)Nc2ccc(Cl)cc2F)C(=O)N1c1ccc(-c2ccccc2S(C)(=O)=O)c(F)c1F] | 552.1 | Method D, RT = 1.831 min, 100% | ¹H NMR (400 MHz, DMSO-d₆) δ = 8.71-8.55 (m, 1H), 8.21-8.09 (m, 2H), 7.91-7.73 (m, 2H), 7.61-7.50 (m, 1H), 7.42 (dd, J = 11.2, 2.0 Hz, 1H), 7.37-7.24 (m, 2H), 7.24-7.11 (m, 2H), 4.70-4.52 (m, 1H), 4.39-4.13 (m, 1H), 3.06 (s, 3H), 2.38-2.23 (m, 2H), 1.12 (d, J = 6.1 Hz, 3H). |
| 130 | 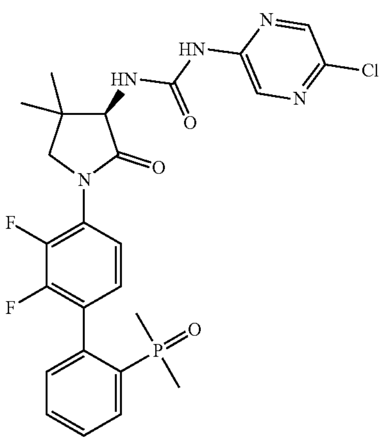 [SMILES: CC1(C)CN(c2ccc(-c3ccccc3P(C)(C)=O)c(F)c2F)C(=O)[C@@H]1NC(=O)Nc1cnc(Cl)cn1] | 548.2 | Method C, RT = 1.578 min, 99.6% | ¹H NMR (400 MHz, DMSO-d₆) δ = 9.73-9.50 (m, 1H), 8.95 (d, J = 1.2 Hz, 1H), 8.44 (d, J = 1.5 Hz, 1H), 7.97-7.85 (m, 1H), 7.71-7.56 (m, 2H), 7.43-7.31 (m, 3H), 7.30-7.21 (m, 1H), 4.67 (d, J = 9.0 Hz, 1H), 3.89-3.82 (m, 1H), 3.47 (br. d., J = 9.5 Hz, 1H), 1.53 (d, J = 13.2 Hz, 6H), 1.23 (s, 3H), 1.07 (s, 3H). |
| 131 | 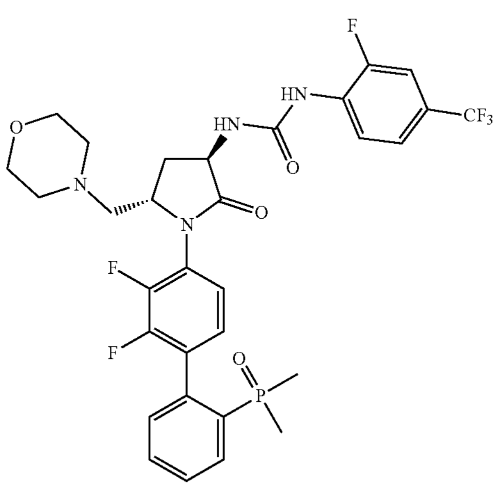 [SMILES: CP(C)(=O)c1ccccc1-c1ccc(N2C(=O)[C@H](NC(=O)Nc3ccc(C(F)(F)F)cc3F)C[C@H]2CN2CCOCC2)c(F)c1F] | 669.4 | Method D, RT = 1.764 min, 100% | 1H NMR (400 MHz, DMSO-d₆) δ = 8.93 (d, J = 2.0 Hz, 1H), 8.40 (t, J = 8.6 Hz, 1H), 7.94 (dd, J = 12.6, 7.5 Hz, 1H), 7.73-7.57 (m, 3H), 7.50 (br. d., J = 8.6 Hz, 1H), 7.41-7.17 (m, 4H), 4.78-4.66 (m, 1H), 4.47-4.28 (m, 1H), 3.32-3.20 (m, 2H), 3.29-3.07 (m, 2H), 2.56-2.48 (m, 2H), 2.46-2.17 (m, 6H), 1.51 (br. d., J = 13.2 Hz, 6H). |

| Ex | Structure | LCMS (M + H)+ | HPLC Method, RT (min.) & Purity | ¹H NMR |
|---|---|---|---|---|
| 132 | 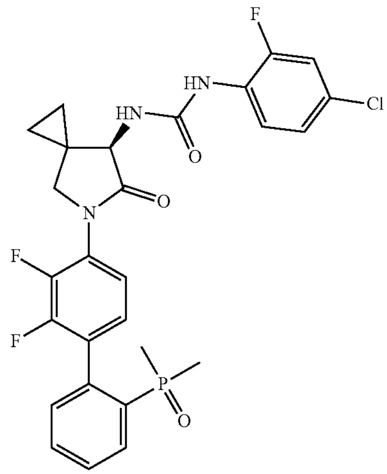 [SMILES: CP(C)(=O)c1ccccc1-c1ccc(N2CC3(CC3)[C@@H](NC(=O)Nc3ccc(Cl)cc3F)C2=O)c(F)c1F] | 579.2 (M + NH₄)⁺ | Method D, RT = 1.736 min, 100% | ¹H NMR (400 MHz, DMSO-d₆) δ = 8.61-8.54 (m, 1H), 8.14 (t, J = 8.8 Hz, 1H), 7.96-7.88 (m, 1H), 7.68-7.59 (m, 2H), 7.44 (dd, J = 11.1, 2.6 Hz, 1H), 7.41-7.35 (m, 2H), 7.30-7.24 (m, 1H), 7.22-7.18 (m, 1H), 7.09-7.01 (m, 1H), 4.78-4.76 (m, 1H), 4.16-4.05 (m, 1H), 3.62-3.53 (m, 1H), 1.52 (br. d., J = 13.2 Hz, 6H), 0.90-0.71 (m, 4H). |
| 133 | 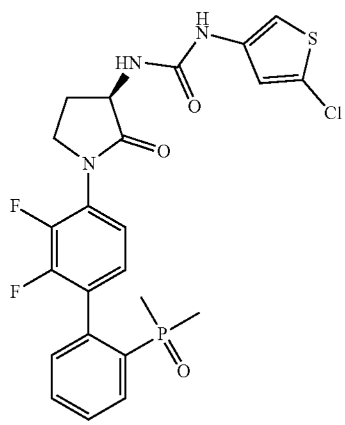 [SMILES: CP(C)(=O)c1ccccc1-c1ccc(N2CC[C@@H](NC(=O)Nc3csc(Cl)c3)C2=O)c(F)c1F] | 524.1 | Method E, RT = 1.518 min, 98.9% | 1H NMR (400 MHz, DMSO-d6) δ = 8.99 (s, 1H), 7.92 (m, 1H), 7.52-7.72 (m, 2H), 7.33-7.41 (m, 2H), 7.21-7.29 (m, 1H), 7.04 (m, 2H), 6.73 (d, J = 7.5 Hz, 1H), 4.53 (m, 1H), 3.83-3.95 (m, 1H), 3.71-3.81 (m, 1H), 2.60-2.54 (m, 1H), 2.04-2.19 (m, 1H), 1.52 (br. d., J = 13.2 Hz, 6H). |
| 134 | 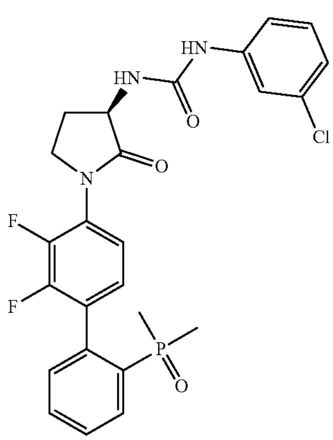 [SMILES: CP(C)(=O)c1ccccc1-c1ccc(N2CC[C@@H](NC(=O)Nc3cccc(Cl)c3)C2=O)c(F)c1F] | 518.1 | Method D, RT = 1.511 min, 99.1% | |

-continued

| Ex | Structure | LCMS (M + H)+ | HPLC Method, RT (min.) & Purity | ¹H NMR |
|---|---|---|---|---|
| 135 | 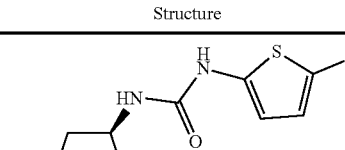 | 524.1 | Method D, RT = 1.496 min, 95.0% | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A method for treating a heart disease comprising administering a therapeutically effective amount of a compound to a patient in need thereof, wherein the compound is

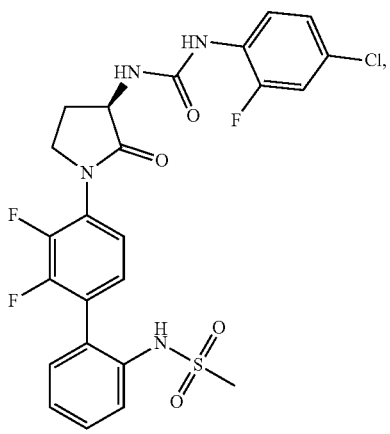 [SMILES: CS(=O)(=O)Nc1ccccc1-c1ccc(N2CC[C@@H](NC(=O)Nc3ccc(Cl)cc3F)C2=O)c(F)c1F]

or a pharmaceutically acceptable salt.

2. The method of claim 1 wherein the heart disease is selected from the group consisting of angina pectoris, unstable angina, myocardial infarction, heart failure, acute coronary disease, acute heart failure, chronic heart failure, and cardiac iatrogenic damage.

3. The method of claim 2 wherein the heart failure is selected from the group consisting of congestive heart failure, systolic heart failure, diastolic heart failure, heart failure with reduced ejection fraction (HF$_R$EF), heart failure with preserved ejection fraction (HF$_P$EF), acute heart failure, chronic heart failure of ischemic and non-ischemic origin.

4. A method for treating a heart disease comprising administering a therapeutically effective amount of a compound to a patient in need thereof, wherein the compound is

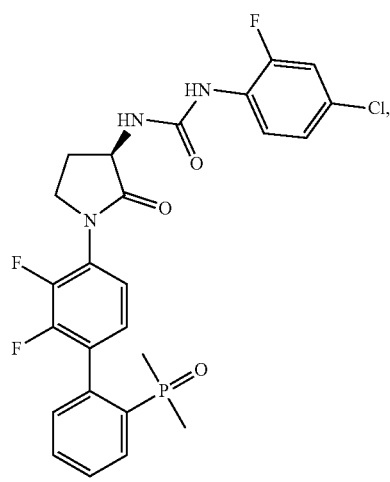 [SMILES: CP(C)(=O)c1ccccc1-c1ccc(N2CC[C@@H](NC(=O)Nc3ccc(Cl)cc3F)C2=O)c(F)c1F]

or a pharmaceutically acceptable salt.

5. The method of claim 4 wherein the heart disease is selected from the group consisting of angina pectoris, unstable angina, myocardial infarction, heart failure, acute coronary disease, acute heart failure, chronic heart failure, and cardiac iatrogenic damage.

6. The method of claim 5 wherein the heart failure is selected from the group consisting of congestive heart failure, systolic heart failure, diastolic heart failure, heart failure with reduced ejection fraction (HF$_R$EF), heart failure with preserved ejection fraction (HF$_P$EF), acute heart failure, chronic heart failure of ischemic and non-ischemic origin.

7. A method for treating a heart disease comprising administering a therapeutically effective amount of a compound to a patient in need thereof, wherein the compound is

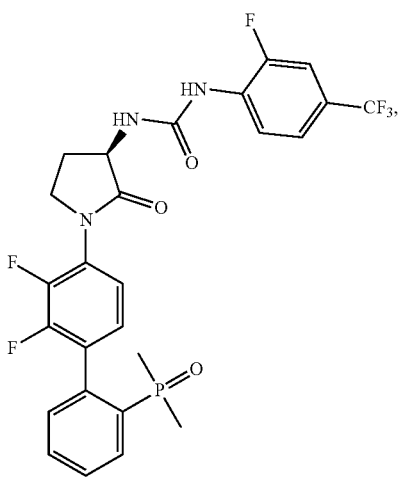 [SMILES: CP(C)(=O)c1ccccc1-c1ccc(N2CC[C@@H](NC(=O)Nc3ccc(C(F)(F)F)cc3F)C2=O)c(F)c1F]

or a pharmaceutically acceptable salt.

8. The method of claim 7 wherein the heart disease is selected from the group consisting of angina pectoris, unstable angina, myocardial infarction, heart failure, acute coronary disease, acute heart failure, chronic heart failure, and cardiac iatrogenic damage.

9. The method of claim 8 wherein the heart failure is selected from the group consisting of congestive heart failure, systolic heart failure, diastolic heart failure, heart failure with reduced ejection fraction ($HF_REF$), heart failure with preserved ejection fraction ($HF_PEF$), acute heart failure, chronic heart failure of ischemic and non-ischemic origin.

10. A method for treating a heart disease comprising administering a therapeutically effective amount of a compound to a patient in need thereof, wherein the compound is or a pharmaceutically acceptable salt.

11. The method of claim 10 wherein the heart disease is selected from the group consisting of angina pectoris, unstable angina, myocardial infarction, heart failure, acute coronary disease, acute heart failure, chronic heart failure, and cardiac iatrogenic damage.

12. The method of claim 11 wherein the heart failure is selected from the group consisting of congestive heart failure, systolic heart failure, diastolic heart failure, heart failure with reduced ejection fraction ($HF_REF$), heart failure with preserved ejection fraction ($HF_PEF$), acute heart failure, chronic heart failure of ischemic and non-ischemic origin.

13. A method for treating a heart disease comprising administering a therapeutically effective amount of a compound to a patient in need thereof, wherein the compound is

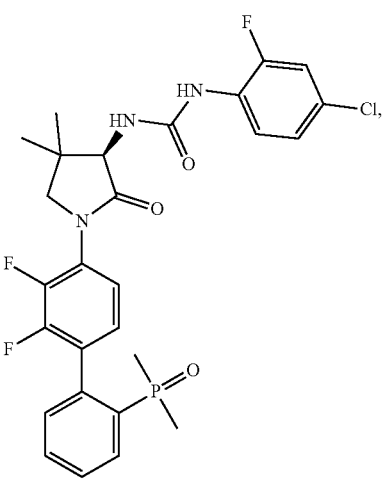 [SMILES: CC1(C)CN(c2ccc(-c3ccccc3P(C)(C)=O)c(F)c2F)C(=O)[C@@H]1NC(=O)Nc1ccc(Cl)cc1F]

or a pharmaceutically acceptable salt.

14. The method of claim 13 wherein the heart disease is selected from the group consisting of angina pectoris, unstable angina, myocardial infarction, heart failure, acute coronary disease, acute heart failure, chronic heart failure, and cardiac iatrogenic damage.

15. The method of claim 14 wherein the heart failure is selected from the group consisting of congestive heart failure, systolic heart failure, diastolic heart failure, heart failure with reduced ejection fraction ($HF_REF$), heart failure with preserved ejection fraction ($HF_PEF$), acute heart failure, chronic heart failure of ischemic and non-ischemic origin.

* * * * *